(12) United States Patent
Kim et al.

(10) Patent No.: US 11,278,341 B2
(45) Date of Patent: Mar. 22, 2022

(54) METHOD OF SAFELY USING CONTROLLED COOLING SYSTEMS AND DEVICES

(71) Applicants: RECENSMEDICAL, INC., Ulsan (KR); Ulsan National Institute of Science and Technology, Ulsan (KR)

(72) Inventors: Gun-Ho Kim, Ulsan (KR); Jae Bum Cho, Seoul (KR); Dae Hyun Kim, Hwaseong (KR); Chul Ho Lee, Yongin (KR)

(73) Assignees: RECENSMEDICAL, INC., Ulsan (KR); Ulsan National Institute of Science and Technology, Ulsan (KR)

( * ) Notice: Subject to any disclaimer, the term of this patent is extended or adjusted under 35 U.S.C. 154(b) by 0 days.

(21) Appl. No.: 17/373,237

(22) Filed: Jul. 12, 2021

(65) Prior Publication Data
US 2022/0015817 A1 Jan. 20, 2022

(51) Int. Cl.
*A61B 18/02* (2006.01)
*A61B 18/00* (2006.01)

(52) U.S. Cl.
CPC .......... *A61B 18/0218* (2013.01); *A61B 2018/00315* (2013.01); *A61B 2018/00714* (2013.01); *A61B 2018/00898* (2013.01); *A61B 2018/00922* (2013.01); *A61B 2018/00952* (2013.01); *A61B 2018/0231* (2013.01); *A61B 2562/0247* (2013.01); *A61B 2562/0271* (2013.01)

(58) Field of Classification Search
CPC ..... A61F 2007/0057; A61F 2007/0058; A61B 18/0218
See application file for complete search history.

(56) References Cited

U.S. PATENT DOCUMENTS

| | | | |
|---|---|---|---|
| 2,004,823 | A | 6/1935 | Meyer |
| 2,044,823 | A | 6/1936 | Whiteside |
| 4,646,735 | A | 3/1987 | Seney |
| 5,976,123 | A | 11/1999 | Baumgardner et al. |
| 6,099,521 | A | 8/2000 | Shadduck |
| 6,141,985 | A | 11/2000 | Cluzeau et al. |
| 6,632,219 | B1 | 10/2003 | Baranov et al. |
| 6,669,688 | B2 | 12/2003 | Svaasand et al. |
| 7,037,326 | B2 | 5/2006 | Lee |
| 7,780,656 | B2 | 8/2010 | Tankovich |
| 7,963,959 | B2 | 6/2011 | Da Silva et al. |
| 8,083,734 | B2 | 12/2011 | Steinfatt et al. |

(Continued)

FOREIGN PATENT DOCUMENTS

| | | |
|---|---|---|
| EP | 1030611 B1 | 9/2004 |
| EP | 1401347 B1 | 8/2011 |
| EP | 2010087 B1 | 11/2014 |
| EP | 2910276 A1 | 8/2015 |

(Continued)

OTHER PUBLICATIONS

PCT/KR2017/012935 International Search Report and Written Opinion dated Jun. 4, 2018.

(Continued)

*Primary Examiner* — Ronald Hupczey, Jr.
(74) *Attorney, Agent, or Firm* — Wilson Sonsini Goodrich & Rosati

(57) ABSTRACT

Present disclosure provides a cooling device with safety features and methods for controlling temperature of the cooling device for safe cooling of target surface.

20 Claims, 24 Drawing Sheets

(56) References Cited

U.S. PATENT DOCUMENTS

| | | |
|---|---|---|
| 8,177,827 B2 | 5/2012 | Shapiro |
| 8,256,233 B2 | 9/2012 | Boyden et al. |
| 8,652,131 B2 | 2/2014 | Muller et al. |
| 8,672,879 B2 | 3/2014 | Grant et al. |
| 8,788,060 B2 | 7/2014 | Nebrigic et al. |
| 8,858,583 B2 | 10/2014 | Shtram et al. |
| 9,017,318 B2 | 4/2015 | Fourkas et al. |
| 9,039,688 B2 | 5/2015 | Palmer, III et al. |
| 9,066,712 B2 | 6/2015 | Fourkas et al. |
| 9,113,855 B2 | 8/2015 | Burger et al. |
| 9,398,975 B2 | 7/2016 | Muller et al. |
| 9,522,031 B2 | 12/2016 | Anderson et al. |
| 9,549,773 B2 | 1/2017 | Anderson et al. |
| 9,642,741 B2 | 5/2017 | Feng et al. |
| 9,801,677 B2 | 10/2017 | Anderson et al. |
| 9,855,166 B2 | 1/2018 | Anderson et al. |
| 9,956,355 B2 * | 5/2018 | Besirli .................... A61F 7/007 |
| 9,974,684 B2 | 5/2018 | Anderson et al. |
| 10,085,881 B2 | 10/2018 | Karnik et al. |
| 10,154,870 B2 | 12/2018 | Ottanelli |
| 10,188,444 B2 | 1/2019 | Fourkas et al. |
| 10,213,244 B2 | 2/2019 | Fourkas et al. |
| 10,322,248 B2 | 6/2019 | Besirli et al. |
| 10,363,080 B2 | 7/2019 | Elkins et al. |
| 10,543,032 B2 | 1/2020 | Babkin |
| 2002/0120315 A1 | 8/2002 | Furuno et al. |
| 2004/0102768 A1 | 5/2004 | Cluzeau et al. |
| 2004/0111087 A1 | 6/2004 | Stern et al. |
| 2005/0059940 A1 | 3/2005 | Weber et al. |
| 2006/0200117 A1 | 9/2006 | Hermans |
| 2006/0213509 A1 | 9/2006 | Marin et al. |
| 2007/0005048 A1 | 1/2007 | Niedbala et al. |
| 2007/0239236 A1 | 10/2007 | Manstein |
| 2008/0164296 A1 | 7/2008 | Shelton et al. |
| 2008/0221561 A1 | 9/2008 | Geiger et al. |
| 2009/0036846 A1 | 2/2009 | Dacquay et al. |
| 2009/0062751 A1 | 3/2009 | Newman, Jr. |
| 2009/0163902 A1 | 6/2009 | DeLonzor et al. |
| 2010/0010480 A1 | 1/2010 | Mehta et al. |
| 2010/0087805 A1 | 4/2010 | Citterio et al. |
| 2010/0196343 A1 | 8/2010 | O'Neil et al. |
| 2010/0198207 A1 | 8/2010 | Elkins et al. |
| 2011/0072834 A1 | 3/2011 | Ishikura et al. |
| 2011/0098791 A1 | 4/2011 | Kim |
| 2011/0137268 A1 | 6/2011 | Thomason et al. |
| 2011/0152850 A1 | 6/2011 | Niedbala et al. |
| 2011/0177474 A1 | 7/2011 | Jamnia et al. |
| 2011/0224761 A1 | 9/2011 | Manstein |
| 2012/0130458 A1 | 5/2012 | Ryba et al. |
| 2012/0191166 A1 | 7/2012 | Callister et al. |
| 2012/0232549 A1 | 9/2012 | Willyard et al. |
| 2012/0265278 A1 | 10/2012 | Fourkas et al. |
| 2013/0116719 A1 | 5/2013 | Shtram et al. |
| 2013/0296811 A1 | 11/2013 | Bangera et al. |
| 2013/0315924 A1 | 11/2013 | Hsu et al. |
| 2014/0012226 A1 | 1/2014 | Hochman |
| 2014/0200511 A1 | 7/2014 | Boyden et al. |
| 2014/0277023 A1 | 9/2014 | Sekino et al. |
| 2015/0051545 A1 | 2/2015 | Henderson et al. |
| 2016/0058488 A1 | 3/2016 | Fourkas et al. |
| 2016/0183996 A1 | 6/2016 | Burger et al. |
| 2016/0242956 A1 | 8/2016 | Pilby Gomez |
| 2016/0262820 A1 | 9/2016 | Allison et al. |
| 2016/0279350 A1 | 9/2016 | Besirli et al. |
| 2017/0014174 A1 | 1/2017 | Levine et al. |
| 2017/0062793 A1 | 3/2017 | Zakharyan et al. |
| 2017/0224935 A1 | 8/2017 | Hoffmann et al. |
| 2017/0231816 A1 | 8/2017 | Ryan |
| 2017/0232243 A1 | 8/2017 | Herweijer |
| 2017/0304558 A1 | 10/2017 | Besirli et al. |
| 2017/0348143 A1 * | 12/2017 | Rosen .................... A61F 7/007 |
| 2017/0354451 A1 | 12/2017 | Marin et al. |
| 2018/0116705 A1 | 5/2018 | Lee et al. |
| 2018/0235805 A1 | 8/2018 | Burger et al. |
| 2018/0310979 A1 | 11/2018 | Peled et al. |
| 2019/0000524 A1 | 1/2019 | Rosen et al. |
| 2019/0015146 A1 | 1/2019 | DuBois |
| 2019/0015602 A1 | 1/2019 | Besirli et al. |
| 2019/0038459 A1 | 2/2019 | Karnik et al. |
| 2019/0175394 A1 | 6/2019 | Kim |
| 2019/0175395 A1 | 6/2019 | Kim |
| 2019/0175396 A1 * | 6/2019 | Kim ......................... A61F 7/12 |
| 2019/0254866 A1 | 8/2019 | Whiteley et al. |
| 2019/0290881 A1 | 9/2019 | Kim |
| 2020/0054483 A1 | 2/2020 | Kim |
| 2020/0206025 A1 | 7/2020 | Chalberg, Jr. et al. |
| 2021/0113365 A1 | 4/2021 | Kim |

FOREIGN PATENT DOCUMENTS

| | | |
|---|---|---|
| EP | 2759272 B1 | 11/2018 |
| JP | H0492663 A | 3/1992 |
| JP | H0686818 A | 3/1994 |
| JP | H10230435 A | 9/1998 |
| JP | 2002505155 A | 2/2002 |
| JP | 2004515270 A | 5/2004 |
| JP | 2005080832 A | 3/2005 |
| JP | 4049358 B2 | 2/2008 |
| JP | 2008212638 A | 9/2008 |
| JP | 2008545462 A | 12/2008 |
| JP | 2009034273 A | 2/2009 |
| JP | 2009056320 A | 3/2009 |
| JP | 2011077314 A | 4/2011 |
| JP | 2012143279 A | 8/2012 |
| JP | 2013142410 A | 7/2013 |
| JP | 2014028130 A | 2/2014 |
| JP | 2014198238 A | 10/2014 |
| JP | 2015510802 A | 4/2015 |
| JP | 2017113635 A | 6/2017 |
| KR | 980005117 U | 3/1998 |
| KR | 100200669 B1 | 6/1999 |
| KR | 20030068633 A | 8/2003 |
| KR | 20040093706 A | 11/2004 |
| KR | 20040094508 A | 11/2004 |
| KR | 100786539 B1 | 12/2007 |
| KR | 100790758 B1 | 1/2008 |
| KR | 20080045022 A | 5/2008 |
| KR | 100851274 B1 | 8/2008 |
| KR | 20100041207 A | 4/2010 |
| KR | 20100060222 A | 6/2010 |
| KR | 20100135863 A | 12/2010 |
| KR | 101053835 B1 | 8/2011 |
| KR | 20110119640 A | 11/2011 |
| KR | 20120115703 A | 10/2012 |
| KR | 20130087770 A | 8/2013 |
| KR | 101366126 B1 | 2/2014 |
| KR | 101386137 B1 | 4/2014 |
| KR | 20140052667 A | 5/2014 |
| KR | 20140069431 A | 6/2014 |
| KR | 20150030264 A | 3/2015 |
| KR | 20150062492 A | 6/2015 |
| KR | 20160048425 A | 5/2016 |
| KR | 101707659 B1 | 2/2017 |
| KR | 101719459 B1 | 3/2017 |
| KR | 20170041776 A | 4/2017 |
| KR | 20170083399 A | 7/2017 |
| KR | 20170089842 A | 8/2017 |
| KR | 20170130470 A | 11/2017 |
| KR | 101813652 B1 | 12/2017 |
| KR | 101819204 B1 | 1/2018 |
| KR | 101840346 B1 | 5/2018 |
| KR | 101862127 B1 | 5/2018 |
| KR | 20180054247 A | 5/2018 |
| KR | 20180109828 A | 10/2018 |
| KR | 101936890 B1 | 1/2019 |
| WO | WO-2016154399 A1 | 9/2016 |
| WO | WO-2018231868 A1 | 12/2018 |
| WO | WO-2020022858 A1 | 1/2020 |

OTHER PUBLICATIONS

PCT/KR2017/013901 International Search Report and written opinion dated Aug. 8, 2018.

(56) References Cited

OTHER PUBLICATIONS

PCT/KR2018/003773 International Search Report and Written Opinion dated Jul. 6, 2018.
PCT/KR2018/006169 International Search Report and Written Opinion dated Nov. 7, 2018.
PCT/KR2018/016491 International Search Report and Written Opinion dated May 30, 2019.
PCT/KR2019/005105 International Search Report and Written Opinion dated Aug. 14, 2019.
PCT/KR2019009411 International Search Report and Written Opinion dated Nov. 15, 2019.
PCT/KR2019/017328 International Search Report and Written Opinion dated Mar. 27, 2020.
Sarifakioglu et al., Evaluating the effects of ice application on the pain felt during botulinum toxin type-a injections: a prospective, randomized, single-blind controlled trial. Ann Plast Surg 53:543-546 (2004).
Smith. Ice anesthesia for injection of dermal fillers. Dermatologic Surgery 36:812-814 (2010).
U.S. Appl. No. 15/828,449 Office Action dated Oct. 2, 2019.
U.S. Appl. No. 16/412,296 Office Action dated Oct. 28, 2020.
PCT/KR2021/009072 International Search Report and Written Opinion dated Nov. 22, 2021.

\* cited by examiner

METHOD OF SAFELY USING CONTROLLED COOLING SYSTEMS AND DEVICES

CROSS-REFERENCE

This application claims the benefit of Korean Patent Application No. KR10-2020-0087100 filed Jul. 14, 2020, and Korean Patent Application No. KR10-2020-0130588 filed Oct. 8, 2020, each of which is incorporated herein by reference in its entirety.

FIELD OF THE INVENTION

The present disclosure relates to a cooling system and a cooling control system using the same. It refers, in some embodiments, to a cooling system that uses a detachable cooling tip to safely cool down a target and a cooling control system and method for performing safe cooling.

BACKGROUND OF THE DISCLOSURE

Retinal diseases that cause blindness such as macular degeneration, diabetic retinopathy or glaucoma have been increasing rapidly as the elderly population increases and the number of people suffering from diabetes increases. Accordingly, studies and research on eye surgery to treat retinal diseases have increased.

Intravitreal injections, also called IVT, are widely used. IVT involves injecting into the eyes of the patient a drug that has been produced for and proven to be effective on various retinal diseases. IVT must be performed with eye anesthesia prior to the injection of the drug.

In traditional retinal surgeries, as eye anesthesia is performed using anesthetic drugs, the reaction between the anesthetic drugs and injected drug should be taken into consideration. Waiting is required until an anesthetic effect is seen, which affects the entire duration of surgery and puts an emotional burden on patients. In this respect, the method of rapidly cooling the eyes using cooling energy for rapid anesthetic effect has been focused.

The safety of the cooling method above remains to be solved, and a more specific structure of a cooling device and a cooling control method for safety are required. Also, enhancing user comfort when using the cooling device and user confidence that the cooling device is safely and properly used should be taken into consideration in the future.

SUMMARY OF THE DISCLOSURE

Disclosed herein, in certain embodiments, includes methods of controlling temperature of a handheld cooling device to safely cool a target surface. In certain embodiments, the method comprises a step of i) providing the handheld cooling device, wherein the handheld cooling device comprises (a) a cooling medium; (b) a target surface contact element; (c) a target surface contact detection module configured to detect contact of the target surface contact element with the target surface; (d) an input element; (e) an input element detection module configured to detect actuation of the input element; and (f) a control module configured to receive a standby temperature, a standby contact time, a standby trigger time; and a target temperature. The method further comprises steps of ii) receiving, by the control module, the standby temperature, the standby contact time, the standby trigger time; and the target temperature, iii) cooling the cooling medium to reach the standby temperature, iv) detecting, by the target surface contact detection module, a contact of the target surface contact element with the target surface within the standby contact time, v) detecting, by the input element detection module, an actuation of the input element within the standby trigger time, wherein the detection of the contact is detected before the detection of the actuation of the input element, and vi) cooling the cooling medium to the target temperature when the contact is detected within the standby contact time and the actuation is detected within the standby trigger time, wherein the target temperature is lower than the standby temperature. In some embodiments, the standby trigger time begins when the contact of the target surface contact element is detected. In some embodiments, the standby contact time begins when the cooling medium reaches the standby temperature.

In certain embodiments, the target surface contact detection module comprises a temperature sensor, a pressure sensor, or a capacitive sensor. In some embodiments, the target surface contact detection module comprises the temperature sensor, and the detection of the contact comprises detecting, by the temperature sensor, an instantaneous rate of change of temperature (dT/dt) of the cooling medium being more than or equal to a predetermined threshold. In some embodiments, the device further comprises a second temperature sensor, and the detection of the contact further comprises detecting, by the second temperature sensor, an instantaneous rate of change of temperature (dT/dt) of the cooling medium. In some embodiments, the temperature sensor is disposed proximal to the target surface contact element, and the second temperature sensor is disposed distal to the target surface contact element. In some embodiments, the predetermined threshold comprises at least 1° C./sec. In some embodiments, the standby contact time comprises less than or equal to 60 seconds. In some embodiments, the standby trigger time comprises less than or equal to 20 seconds.

In some embodiments, the actuation of the input element comprises pressing a button, turning a knob, or flipping a switch. In some embodiments, the target surface contact element comprises a tip member.

In some embodiments, the handheld cooling device further comprises a notification module, and the method further comprises sending a notification, by the notification module, when the contact is detected within the standby contact time or when the actuation is detected within the standby trigger time. In certain embodiments, the notification comprises an audio alert, a visual alert, or any combination thereof.

In some embodiments, the control module is further configured to receive a target temperature time, the method further comprising maintaining the cooling medium at the target temperature for the target temperature time. In some embodiments, the target temperature time is 60 seconds or less. In some embodiments, the method further comprises stopping the cooling of the cooling medium when the target temperature time is reached. In some embodiments, the target surface is an ocular region. In other embodiments, the target surface is a region of the ocular surface without the retina underneath. In some embodiments, the cooling anesthetic site on the target surface is about 7 mm in diameter (10 mm, 9 mm, 8 mm, 7 mm, 6 mm, 5 mm, 4 mm, 3 mm, 2 mm, 1 mm, less than 15 mm, etc.). In some embodiments, the center of the cooling tip, when engaging the target surface of the ocular region, is about 3.5 mm away from the edge of cornea limbus (about 4 mm away, about 4.5 mm away, about 5 mm away, 5.5 mm, away, etc.) In some embodiments, the target surface is not the cornea limbus. In some embodiments, the shape of the cooling anesthetic site or the portion of the cooling tip that engages the target surface can be in any suitable shape (e.g., circular, square, rectangular, oval, triangular, quadrilateral, triangle, linear, etc.). In some embodiments, the standby temperature is selected from 0° C. to −20° C. In some embodiments, the target temperature is selected from −5° C. to −60° C.

The above objects, features, and advantages of the present application shall become more apparent through the following detailed description related to the drawings. However, in the present specifications, various changes may be made, and various embodiments may be provided. Hereinafter, specific embodiments are illustrated in the drawings and described in detail.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

DETAILED DESCRIPTION OF THE DISCLOSURE

Figure 1:
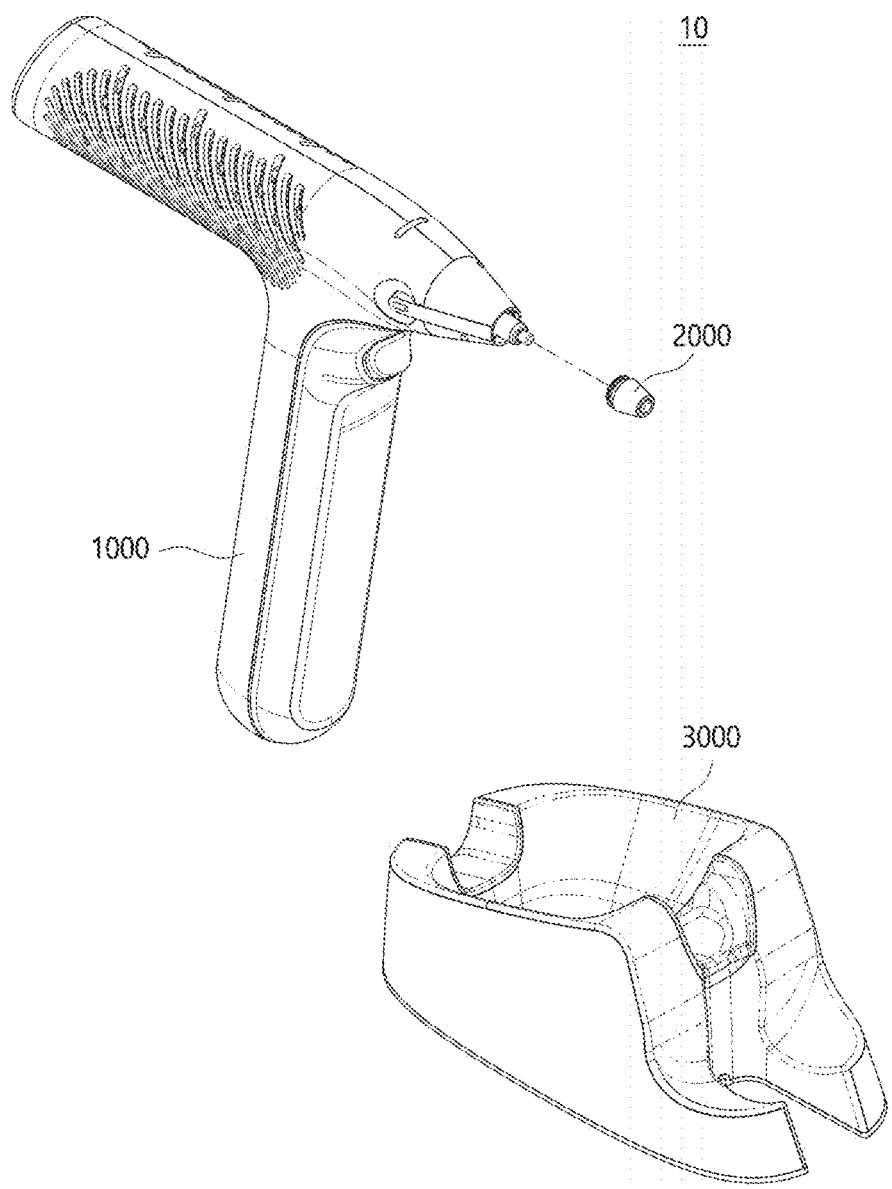
FIG. 1 shows a cooling system according to an exemplary embodiment of the present disclosure.

In some embodiments, the present disclosure provides a cooling device that has a cooling tip detachable therein. In other embodiments, the present disclosure also provides a cooling tip which delivers cooling energy by being installed in a cooling device. In some embodiments, the cooling tip includes substances that has different thermal conductivity respectively.

In some embodiments, the cooling device includes a structure that enables the attachment and detachment of the cooling tip. In some embodiments, the cooling device further includes a space for alleviating impact between any component of the external body of the cooling device and any component located inside the external body cooling device.

In some embodiments, the cooling device includes a sensor module positioned near the cooling tip of a cooling device. In further embodiments, the sensor module is operably coupled to the sensor, which detects the contact of a target. In some embodiments, the target comprises an ocular surface, skin, mucous cells, mucous producing cells or tissues, or cutaneous cells. In some embodiments, the sensor comprises resistive sensors, thermistors, thermocouples, or infrared (IR) sensors.

In some embodiments, the present disclosure provides a controlled cooling method. In some embodiments, the controlled cooling method cools a target at a particular temperature (e.g., target temperature) only if one or more safety conditions are satisfied. These safety conditions may include a component of a cooling device (e.g., cooling tip, tip member, cooling medium, etc.) reaching a standby temperature, maintaining a standby temperature for a given amount of time (e.g., standby contact time), contacting the component of a cooling device (e.g., cooling tip, tip member, cooling medium, etc.) at the target, detecting the contact within a given amount of time (e.g., standby contact time), detecting the contact for a given amount of time, detecting the contact by measuring a temperature of the cooled component reaching a certain threshold (e.g., increasing 1° C./sec from the standby temperature), a user actuating an element on the cooling device (e.g., button, trigger, etc.), detecting the actuation of the element (e.g., button, trigger, etc.) within a given amount of time (standby trigger time), detecting the actuation of the element (e.g., button, trigger, etc.) for a certain amount of time, or any combination thereof. In some embodiments, the standby contact time must be satisfied before the standby trigger time. In some embodiments, the standby trigger time must be satisfied before the standby contact time. In some embodiments, the safety condition further comprises that the detection of the contact (e.g., for a given amount of time and/or within a given time) and the actuation (e.g., for a given amount of time and/or within a given amount of time) must both be completed before a given amount of time. In some embodiments, failure to satisfy one or more safety conditions results in the stoppage of any cooling of the cooling element and allowing the cooling element to warm to a desired temperature (e.g., room temperature). In other embodiments, satisfaction of one or more of these safety conditions results in further cooling the component to the target temperature for a given amount of time (e.g., target temperature time). In further embodiments, once the cooling element has been cooled at the target temperature for the given amount of time, the maintaining of the target temperature automatically stops, which results in the cooled component going to a warmer temperature.

In some embodiments, the standby temperature is reached when the cooling device is not in contact with the target. In some embodiments, the standby temperature varies room temperature. In some embodiments, the standby temperature is determined as a time for reaching to the standby temperature from the room temperature. In some embodiments, the standby temperature comprises between 0° C. and −15° C. In some embodiments, the standby temperature comprises between −10° C. and −15° C. In some embodiments, the standby trigger time is selected a time between 2 seconds and 10 seconds. In some embodiments, the standby trigger time is about 5 seconds. In some embodiments, the standby trigger time is about 10 seconds or less. In some embodiments, the standby trigger time is no longer than 10 seconds. In some embodiments, the target temperature comprises between −10° C. to −20° C. In some embodiments, the target temperature is about −15° C. In some embodiments, the target temperature time comprises between about 5 seconds to about 20 seconds. In some embodiments, the target temperature time is between about 7 seconds to about 15 seconds. In some embodiments, the target temperature time is about 10 seconds. In further embodiments, any one or more of the standby temperature time, the standby temperature, the standby trigger time, the target temperature, the target temperature time may be pre-set for a given range of time, a range of temperatures, or any combination thereof.

In another embodiment of the present disclosure, a tip storage kit or unit configured to store one or more cooling tips is provided. In another embodiment of the present disclosure, a support for holding the cooling device is also provided.

According to one embodiment of the present disclosure, provided is a detachable cooling tip for cooling a target by being installed in a cooling device that has a cooling medium comprising: 1) a tip body that defines the inner space to which the cooling medium is inserted and includes a connecting part for connecting the cooling device and 2) a contacting member that may be detachable from the tip body and has a higher thermal conductivity than that of the tip body so as to deliver the cooling energy received from the cooling medium to the target. This involves the contacting member being pressed by the cooling medium in the direction of the central axis of the tip body while the contacting member is disposed in the tip body, an engaging portion of the contact member being in close contact with the tip body, and at least a part of the contact member being fixed on the tip body by protruding from the tip body.

According to another embodiment of the present disclosure, provided is a cooling device for cooling a target, comprising: 1) a body in which transmitting cooling energy by contacting a surface of the target is mounted and separated from; 2) a cooling module that includes a cooling medium for cooling the target and a temperature control member for controlling a temperature of the cooling medium by thermally coupling with the cooling medium; and 3) at least one elastic member of which one end is connected to the body and the other end is connected to the cooling module, wherein when the cooling tip is mounted on the body in the initial direction and the cooling tip presses the cooling module in the first direction, the elastic member increases and the cooling module moves from the first position to a second position. When the elastic member is contracted, the cooling module moves from the second position to the first position so that the cooling tip is separated from the body in the second direction, which is opposite to the first direction.

According to another embodiment of the present disclosure, provided is a cooling device for cooling a target, comprising: a body; a cooling module disposed inside the main body, comprising: a cooling medium that provides cooling energy to the target and a temperature control member that is thermally coupled with the cooling medium to provide cooling energy; a trigger button that generates a trigger signal according to the user's input; and a control module for controlling the temperature of the cooling medium by controlling the temperature control member, wherein the control module controls, before the temperature of the cooling medium reaches a target temperature, the temperature of the cooling medium to reach an standby temperature different from the target temperature, and maintains the temperature of the cooling medium at the standby temperature during the standby time, increases the temperature of the cooling medium when the standby time elapses without satisfying the cooling performance condition, and determines whether the cooling performance condition is satisfied based on the received trigger signal.

In some embodiments, a cooling tip that has been mounted may be replaced each time a target is cooled to prevent contamination of the cooling tip.

In some embodiments, an additional tip disinfection process may be omitted by using a new cooling tip whenever a target is cooled.

Another technical advantage of the disclosure includes, in some embodiments, the cooling tip having separate components that have different thermal conductivity so that the cooling energy may be efficiently transmitted to the target. Another technical advantage of the disclosure includes, in some embodiments, a configuration of the detachable cooling tip and the cooling device that allows for the cooling tip to be easily mounted to and detached from the cooling device.

Another technical advantage of the disclosure includes, in some embodiments, that a target is cooled when one or more safety conditions is satisfied, which increases the cooling safety. Another technical advantage of the disclosure includes that the cooling device operates to perform cooling mainly when it contacts a target so that the safety of cooling performance may be improved. Another technical advantage of the disclosure includes, in some embodiments, that excessive cooling of a target may be prevented by cooling one or more components of the cooling device first at a standby temperature (which in some embodiments is at a temperature lower than the target temperature) for a standby temperature time, then after this condition is met is the one or more components cooled to a target temperature for a target temperature time.

Another technical advantage of the disclosure includes, in some embodiments, that a cooling tip is sealed and stored in the tip storage to prevent contamination.

Another technical advantage of the disclosure includes, in some embodiments, that a support corresponding to the shape of the cooling device is provided so that the components of the cooling device are safely protected and the cooling device can be held on the support.

The effect by the present disclosure is not limited to those described above. Those not listed above should be clearly understood by a person skilled in the art to which the present disclosure belongs from the included present specifications and drawings.

Terms and Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising.".

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of" or "consisting of" The phrase "consisting essentially of" is used herein to require the specified feature(s) as well as those which do not materially affect the character or function of the claimed disclosure. As used herein, the term "consisting" is used to indicate the presence of the recited feature alone. As used herein, the term "and/or" includes any and all combinations of one or more of the associated listed items.

In the drawings, the thicknesses of layers and regions are exaggerated for clarity, and elements or layers are referred to as "on" or "on" the other elements or layers includes not only cases where they are directly above the other components or layers, but also cases where there are other layers or other components interposed in the middle. The same reference numerals throughout these specifications refer to the same elements unless indicated otherwise. In addition, components that have the same functions within the scope of the same idea shown in the drawings of each embodiment are described using the same reference numerals, and redundant descriptions thereof are omitted.

The numbers (e.g., first, second, etc.) used in the description of the present disclosure are merely identification symbols for distinguishing one component from other components.

Unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Thus, the term "thermally coupled" refers any relationship between two materials or objects where the heat is transferred by direct or indirect contact (e.g., via vapor, air, liquid, mechanical forces, etc.).

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The terms "determining," "measuring," "evaluating," are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

In some embodiments, the term 'target' refers to an object that is cooled by using a cooling system. For example, in some embodiments, the target is a target intended to be put into an anesthetic state or a painless state in order to receive a medical procedure. Specifically, the target comprises a part of a body including nerves, such as eyes, skin, or gum with disease. In another example, the target comprises a target for skin cosmetic treatment using cooling. Specifically, the target can comprise a part of a body including a point that may be removed by cooling a local area, warts, callus, etc., or a part of a body requiring local anesthesia during laser treatment such as hair removal, peeling, and Botox treatment. In some embodiments, the target can include cells or tissues for scientific experiments (e.g., cell culture, tissue culture, cultured cells, cultured tissue). Alternatively and/or additionally, the target can include any containers (e.g., glass vial, glass substrate, petri dish, etc.) containing cells or tissues.

As used herein, the term 'cooling' refers to reducing the temperature of a target to be cooled. In some embodiments, the cooling is accomplished by applying cooling energy to the target to be cooled and absorbing the heat energy of the target to be cooled. In some embodiments, the cooling energy may refer to the escaping of heat by cooling and may be understood as a concept for expressing the decrease of thermal energy. For example, cooling can be conducted by applying cooling energy to the cooling medium, which in some embodiments may further cool a tip, or by applying cooling energy to the tip, and 'contacting' the cooling medium or a cooled tip to a target to be cooled so that the cooling energy can be transmitted or applied to the target. In another example, cooling can be conducted by 'injecting' or jetting a coolant or air gas to apply cooling energy to the target to be cooled. In other words, it should be understood as a comprehensive concept including various methods of applying cooling energy to an object to be cooled. Hereinafter, for convenience of description, cooling a target through a contacting method is described as a main embodiment, but the technical idea of the present specifications is not limited thereto.

In the drawings, components may be exaggerated or reduced in size for convenience of description. For example, the size and thickness of each component shown in the drawings are arbitrarily shown for convenience of description, and the present disclosure is not necessarily limited to what the drawings show.

When a certain embodiment may be implemented differently, a specific process order may be performed differently from the described order. For example, two processes described in succession may be performed simultaneously or performed in an order opposite to the described order.

The section headings used herein are for organizational purposes only and are not to be construed as limiting the subject matter described.

Cooling Tip

Present disclosure provided herein includes a detachable cooling tip for cooling a target, where the detachable cooling tip is installed in a cooling device having a cooling medium. In certain embodiment, the cooling tip comprises 1) a tip body comprising an inner space configured to receive a cooling medium and ii) includes a connecting part for connecting the cooling device; and 2) a contacting member that is detachable from the tip body and has a higher thermal conductivity than that of the tip body so as to deliver the cooling energy received from the cooling medium to the target. In some embodiments, when the contacting member is pressed by the cooling medium in the direction of the central axis of the tip body while the contacting member is disposed in the tip body, an engaging portion of the contact member contacts closely with the tip body, and the contact member is fixed in the tip body while at least a part of the contact member is protruded from the tip body.

In the following embodiments, when a film, region, component, etc. are connected, not only are the film, region, and components directly connected, but other films, regions, and components are interposed between the film, region, and components. This includes cases that are connected indirectly. For example, in the present disclosure, when a film, region, component, etc. are electrically connected, this includes cases where the film, region, component, etc. are directly electrically connected and cases where other films, regions, components, etc. are interposed therebetween.

In some embodiments, the tip body includes an engaging protrusion portion, and the engaging portion of the contact member contacts closely with the engaging protrusion portion of the tip body upon being pressed by the cooling medium.

In some embodiments, one side of the contact member contacting the surface of the target may be larger than the cross section of one end of the cooling medium contacting the contact member.

In some embodiments, the inner diameter of an opening of the tip body corresponds to (e.g., matches to, substantially similar) the outer diameter of the cooling medium receiving member of the cooling device that supports the cooling medium so as to prevent the cooling medium from contacting the inner circumferential surface of the contact member. In some embodiments, the inner diameter of an opening of the tip body is slightly larger than the outer diameter of the cooling medium receiving member, in order to prevent wearing between them. In such embodiments, the difference between the inner diameter of an opening of the tip body and the outer diameter of the cooling medium is minimized or small enough to maximize the heat transfer (radiation, convection, not by contact).

In some embodiments, the length of the contact member in the central axis direction may be shorter than the length of the portion of the cooling medium protruding from the cooling medium receiving member in the central axis direction.

In some embodiments, the heat capacity of the contact member may be smaller than the heat capacity of a portion of the cooling medium corresponding to a predetermined length from a portion providing the cooling energy to the contact member. In some embodiments, the mass of the contact member may be 1 g or less.

In some embodiments, an end of the tip body includes a shape that at least a portion of the tip body protrudes to display an indentation by contacting the surface of the target as the target is cooled, wherein the indentation may be represented by at least one of a ring, a dot and a line.

Cooling Device

Also disclosed herein includes a cooling device for cooling a target. In some embodiments, the cooling device comprises i) a main body on which a cooling tip contacting a surface of the target and transmitting cooling energy to the target is mounted and separated from; ii) a cooling module including a cooling medium for cooling the target and a temperature control member for controlling a temperature of the cooling medium by thermally coupling with the cooling medium; and/or iii) at least one elastic member of which one end is connected to the main body and the other end is connected to the cooling module. In some embodiments, when the cooling tip is mounted on the main body in the first direction and the cooling tip presses the cooling module in the first direction, the elastic member stretches and the cooling module moves from the first position to a second position. In some embodiments, when the elastic member contracts, cooling module moves from the second position to the first position so that the cooling tip is separated from the main body in the second direction opposite to the first direction.

In some embodiments, a pressure exerted by the elastic member between the cooling medium and the cooling tip can be 0.2 MPa or higher. In some embodiments, a pressure exerted by the elastic member between the cooling medium and the cooling tip is between 0.5 to 5 Mpa. In some embodiments, a pressure exerted by the elastic member between the cooling medium and the cooling tip is between 2 to 4 Mpa.

In some embodiments, a coating member that has a hardness that is suitable or sufficient to deform the coating during insertion, complying with any surface roughness at the interface, thereby removing air gaps between the tip and cooling medium. Such coating improves the heat transfer between the tip and cooling medium. In some embodiments, a coating member that has a hardness of no more than 2 Mohs of hardness can be disposed between the cooling medium and the cooling tip.

In some embodiments, the main body includes a coupling module comprising at least one latch, and the cooling tip may be mounted on and separated from the coupling module through the latch.

In some embodiments, the latch comprises a first latch and a second latch that are symmetrically disposed in the coupling module, and when the first latch rotates in a first rotation direction while the cooling tip is mounted on the housing, and the second latch rotates in a second rotation direction opposite to the first rotation direction, the cooling module moves from the second position to the first position as the elastic member contracts so that the cooling tip can be separated from the main body.

In some embodiments, the coupling module comprises a fixing pin inserted in a first insertion direction to fix one end of the elastic member, and a latch pin inserted in a second insertion direction different from the first insertion direction to fix (e.g., substantially immobilize, stabilize, etc) the latch.

In some embodiments, the cooling module comprises a heat radiating member thermally coupled to the temperature control member.

In some embodiments, the main body comprises a body part having shape corresponding to the cooling module so that the cooling module is disposed within the body part, and a grip part to be gripped by the user. In some embodiments, the grip part is disposed on a plane or axis different (e.g., perpendicular) to the body part. In some embodiments, the grip part being disposed on a different plane or axis to the body part allows a user to simultaneously grip the device, utilize the device, and maximize the surface area of the fan that dissipates any heat (allowing the device to function optimally and improve heat dissipation and efficient cooling). In some embodiments, the body part comprises an anti-collision area for preventing collision between the cooling module and one end of the body part. In some embodiments, a distance in the direction of the central axis of the anti-collision area may be set longer than a distance between the first position and the second position.

In some embodiments, the cooling tip comprises i) a contact member that makes contact with the target and ii) a tip body where the contact member is disposed. The tip body may be coupled with the main body mechanically, and the contact member may be coupled with the cooling medium of the cooling module thermally.

In some embodiments, the cooling device comprises a temperature sensor that obtains temperature information of the cooling module. In some embodiments, the temperature sensor may be inserted into the cooling medium.

In some embodiment, the temperature sensor may be disposed such that the center of the temperature sensor is located at a predetermined distance in the second direction from the center of the cooling medium.

In some embodiments, the cooling medium comprises a first part between the temperature sensor and one end of the cooling medium, and a second part between the temperature sensor and the other end of the cooling medium. The first part may have a smaller heat capacity than the second part.

In some embodiments, the cooling device comprises a touch sensor that detects whether the cooling tip contacts or touches the surface of the target.

In some embodiments, the touch sensor is electrically connected to the cooling medium to obtain an electrical characteristic value of the cooling medium. The cooling device may detect whether the cooling tip has contacted the surface of the target based on the electrical characteristic value (e.g., changes in voltage, capacity, or small electrical current flow). In such embodiments, the cooling device comprises the touch sensor that includes voltage/current measuring element and/or the electrical characteristic means voltage or current.

In some embodiments, the cooling device comprises a sensor that detects whether the cooling tip is mounted on the body based on detecting at least one of whether the elastic member is stretched or whether a position of the cooling medium is changed.

In some embodiments, one end of the elastic member connected to the body may be positioned closer to the cooling tip than the other end of the elastic member connected to the cooling module.

Also disclosed herein includes a cooling system for cooling a target. In certain embodiments, the cooling system comprises i) a cooling device including a temperature control member for generating cooling energy, and a cooling medium receiving the cooling energy from the temperature control member; ii) a cooling tip thermally coupled to the cooling medium and configured to transfer the cooling energy obtained from the cooling medium to the target by contacting a surface of the target; and iii) a support on which the cooling device is held, mounted, or placed. In some embodiments, the cooling device comprises a body part in which the temperature control member and the cooling medium are disposed, and a grip part to be gripped by the user. In some embodiments, the support comprises a seating part that has a support groove on which the grip part is mounted, and a wing part protruding from the seating part and surrounding the body part to protect the cooling tip mounted on the cooling device against an external impact.

In some embodiments, the cooling system includes a tester for determining whether the cooling device operates normally. In some embodiments, the tester includes an insertion part thermally coupled to the cooling medium of the cooling device, and a control part that determines whether the cooling device is operating normally based on temperature information at or obtained from the insertion part. In some embodiments, the seating part of the support comprises a storage space in which the tester is accommodated, stored or, placed in.

Also disclosed herein includes a cooling device for cooling a target. In certain embodiments, the cooling device comprises a body; a cooling module including a cooling medium providing cooling energy to the target, and a temperature control member thermally coupled to the cooling medium to provide the cooling energy, by being disposed inside the body; a trigger button that generates a trigger signal according to the user's input; and a control module for controlling the temperature of the cooling medium by controlling the temperature control member. In some embodiments, the control module controls, before the temperature of the cooling medium reaches a target temperature, the temperature of the cooling medium to reach an standby temperature different from the target temperature, and maintains the temperature of the cooling medium at the standby temperature during the standby time, increases the temperature of the cooling medium when the standby time elapses without satisfying the cooling performance condition, and determines whether the cooling performance condition is satisfied based on the received trigger signal.

In some embodiments, the cooling device includes a temperature sensor that is thermally coupled to the cooling medium, and the cooling performance condition comprises a contact condition wherein the cooling medium is thermally coupled to the surface of the target, and the control module may determine whether the contact condition is satisfied based on the temperature value measured by the temperature sensor.

In some embodiments, the control module may ignore the received trigger signal if the contact condition is not satisfied.

In some embodiments, the control module controls the temperature of the cooling medium to become a target temperature different from the standby temperature when the cooling performance condition is satisfied, but if the contact condition is not satisfied, the control module may not control temperature of the cooling medium to reach the target temperature.

Controlled Cooling Methods

Also disclosed herein includes a method of controlling temperature of a handheld cooling device to safely cool a target surface. In some embodiments, the method comprises:

Also disclosed herein includes a cooling control method for controlling a temperature of a cooling medium included in a cooling device when cooling a target using a cooling device. In certain embodiments, the method includes the steps of: controlling the temperature of the cooling medium included in the cooling device to reach a standby temperature; operating a standby contact timer that is set to a standby contact time, and controlling the temperature of the cooling medium to be maintained at the standby temperature during the standby contact time; operating a standby trigger timer set to a standby trigger time when one or more contact conditions is satisfied (e.g., when a cooling tip contacts a surface of the target, when a cooling tip contacts a target surface before a standby contact timer ends, and when a cooling tip contacts a target surface and delivers cooling energy to the target, or any combination thereof); controlling the temperature of the cooling medium to be maintained at a target temperature different from the standby temperature when a condition for receiving a trigger signal is satisfied by the cooling device before the end of the standby trigger timer; and increasing the temperature of the cooling medium if the contact condition is not satisfied before the end of the standby contact timer or the condition for receiving is not satisfied before the end of the standby trigger timer.

Also disclosed herein includes a cooling control method for controlling a temperature of a cooling medium included in the cooling device in cooling a target surface to a target temperature to cool a target using a cooling device. In certain embodiments, the method comprises the following steps: controlling a temperature of the cooling medium to reach an standby temperature different from the target temperature before cooling the target surface to the target temperature by using the cooling device; controlling the temperature of the cooling medium to be maintained at the standby temperature during the standby time; controlling the temperature of the cooling medium to be maintained at the target temperature during the cooling time if the cooling performance condition is satisfied before the standby time elapses; increasing the temperature of the cooling medium when the standby time elapses without the cooling performance condition satisfied, wherein the standby time is set within a range of safety time so as to prevent excessive cooling of the target. In some embodiments, the range of safety time comprises 60 seconds or less, 70 seconds or less, 80 seconds or less, or 90 seconds or less.

In some embodiments, the cooling performance condition comprises a reception condition wherein the cooling device receives a trigger signal instructing a timer operation.

In some embodiments, the cooling performance condition comprises a contact condition wherein a cooling tip connected to the cooling device contacts the surface of the target to transmit cooling energy to the target.

In some embodiments, the cooling performance condition comprises a contact condition wherein a cooling tip connected to the cooling device to transmit cooling energy to the target contacts a surface of the target; and/or a reception condition wherein the cooling device receives a trigger signal.

In some embodiments, whether or not the contact condition is satisfied can be determined by using a temperature sensor thermally coupled to the cooling medium.

In some embodiments, the contact condition may be satisfied when the amount of temperature value change over time measured by the temperature sensor is on or above a predetermined value. In some embodiments, the predetermined value comprises at least 0.5° C./sec, at least 0.6° C./sec, at least 0.7° C./sec, at least 0.8° C./sec, at least 0.9° C./sec, at least 1.0° C./sec, at least 1.1° C./sec, at least 1.2° C./sec, at least 1.3° C./sec, at least 1.4° C./sec, or at least 1.5° C./sec.

In some embodiments, the temperature sensor comprises a first temperature sensor and a second temperature sensor for measuring temperatures of different parts of the cooling medium, and the contact condition may be satisfied based on the amount of temperature value change measured over time by the first temperature sensor and the second temperature sensor. In some embodiments, the cooling medium, which extends in the length direction of the device, has two sensors, a first temperature sensor (S1) and a second temperature sensor (S2). S1 and S2 measure the temperature of inner surface of the colling medium at different position. In such embodiments, S1 is installed close to or proximal to the one end of the cooling medium—close to the cooling tip —, so that its reading changes upon the temperature change at the cooling tip. S2 is installed distal from the cooling tip. Alternatively and/or additionally, S2 is installed close to the Peltier module, so that its reading is delayed due to the heat capacitance of the cooling medium. Such two temperature sensors are operated by feedback mechanism, i.e., when $dT\_s1/dt$ is positive, Peltier power increases, rendering $dT\_s2/dt$ negative. At the moment of touching the target surface, in which $dT\_s1/dt$ is positive, $dT\_s2/dt$ is turned negative.

In some embodiments, the cooling control method may further include a step that involves increasing the temperature of the cooling temperature if the standby time includes a standby contact time and the contact condition is not satisfied within the standby contact time after the temperature of the cooling medium reaches the standby temperature. In some embodiments, the temperature of the cooling temperature is increased in a passive manner, e.g., by turning the Peltier module power off. In some embodiments, the temperature of the cooling temperature is increased in an active manner to modulating the temperature of the cooling medium to a predetermined temperature, or a temperature higher than the standby temperature.

In some embodiments, the method further comprises a step that involves increasing the temperature of the cooling medium if the standby time includes a standby trigger time and the reception condition is not satisfied within the standby trigger time after the contact condition is satisfied within the standby contact time.

In some embodiments, the standby trigger time may be set shorter than the standby contact time. In some embodiments, the standby trigger time comprises 3-10 seconds. In some embodiments, the standby trigger time is about 5 seconds. In some embodiments, the standby trigger time is less than 10 seconds.

In some embodiments, the standby trigger time may be set to 10 seconds or less, 20 seconds or less, 30 seconds or less, 40 seconds or less, 50 seconds or less, or 60 seconds or less.

In some embodiments, the cooling control method comprises a step that involves controlling the temperature of the cooling medium to reach a safe temperature after the cooling time elapses when the cooling performance condition is satisfied.

In some embodiments, the target temperature may be set lower than the standby temperature, and the safety temperature may be set higher than the standby temperature and the target temperature.

In some embodiments, the safety time range may be 90 seconds or less, 80 seconds or less, 70 seconds or less, 60 seconds or less, 50 seconds or less, 40 seconds or less, 30 seconds or less, 20 seconds or less, 10 seconds or less. In some embodiments, the standby trigger time may be set to 10 seconds or less, 20 seconds or less, 30 seconds or less, 40 seconds or less, 50 seconds or less, or 60 seconds or less. In some embodiments, the sum of the standby time and the cooling time may be within 90 seconds, 80 seconds, 70 seconds, 60 seconds, 50 seconds, 40 seconds, 30 seconds, 20 seconds, or 10 seconds.

In some embodiments, the cooling control method provides a notification for instructing the user to perform cooling on the target when the cooling performance condition is satisfied. In some embodiments, the notification comprises a mechanical notification (e.g., vibration), an audio notification (e.g., beep), a visual notification (e.g., light flashing), or any combination thereof.

In some embodiments, the cooling control method provides a notification that instructs the user to start control before providing cooling energy to the cooling medium. In some embodiments the cooling control method provides a notification instructing the user to complete cooling preparation when the temperature of the cooling medium reaches the standby temperature. In some embodiments the cooling control method provides a notification to the user indicating that cooling is being performed between the first time point when the cooling performance condition is satisfied and a second point when the cooling time elapses from the first time point. In some embodiments, the cooling control method provides a notification for instructing the user to install a cooling tip before transmitting the cooling energy from the cooling device to the target in the cooling device or before providing the cooling energy to the cooling medium to the standby temperature. In some embodiments the cooling control method provide a combination of notifications described herein.

In some embodiments, the cooling control method comprises a user mounting a cooling tip (e.g., detachable) to the cooling device before providing the cooling energy to the cooling medium.

In some embodiments, the cooling control method determining whether a cooling tip is properly mounted on the cooling device. In some embodiments, the cooling control method further comprises determining whether a particular tip has already been used before cooling energy is transmitted to the target or the cooling medium. In some embodiments, the method comprises providing a notification to the user when the cooling tip has already been used.

Also disclosed herein includes a cooling control method of controlling a temperature of a cooling medium included in the cooling device using a cooling device, when cooling a target using a cooling device. In certain embodiments, the method comprises determining whether the cooling medium is thermally coupled to the surface of the target; if the cooling medium is thermally coupled to the surface of the target, determining whether a trigger instructing to operate a timer within a time set in advance is received; and when the trigger signal is received within the preset time, maintaining the temperature of the cooling medium at a target temperature below the standby temperature during a cooling time so as to cool the target.

Cooling Tip Storage

Also disclosed herein includes a tip capsule for storing a replaceable cooling tip. In certain embodiments, the tip capsule comprises a tip body mounted on and detachable from a cooling device and a contact part that contacts the target surface and cools the target using cooling energy provided from the cooling device. In some embodiments, a storage hole comprises includes a storage space that has a shape corresponding to the shape of the cooling tip and a protection space extending from the storage space to an end of the storage hole. In some embodiments, the depth of the protection space is set to be larger than the length of the contact part protruding from the tip body to prevent the contact part from reaching the end of the storage hole.

In some embodiments, the storage hole may include a stepped part that distinguishes or separates the storage space and the protection space and supports the tip body of the cooling tip.

In some embodiments, when the cooling tip is inserted into the storage hole, the stepped part may not contact the contact part of the cooling tip.

In some embodiments, the storage space may have a tapered shape whose width becomes narrower in the direction in which the cooling tip is inserted.

In some embodiments, an inclination of an inner wall defining at least a portion of the storage space may be equal to or less than an inclination of a side surface of the tip body.

In some embodiments, the storage space and the protection space have a tapered shape that narrows in a direction in which the cooling tip is inserted, and a slope of the storage space may be greater than that of the protection space.

In some embodiments, the tip capsule includes a sealing member for packing the cooling tip into the storage hole, and the sealing member may be made of a material softer than that of the storage hole.

In some embodiments, the contact part may contact the target surface to transmit the cooling energy obtained from the cooling device.

In some embodiments, the tip body includes an engaging protrusion therein, the contact part includes an engaging part, and the engaging protrusion of the tip body and the engaging part of the contact part are coupled by force fitting so that at least a part of the contact portion may be fixed to the tip body while protruding from the tip body.

Also disclosed herein includes a tip storage for storing a replaceable cooling tip including a tip body mounted on and detachable from a cooling device, and a contact part that contacts a surface of a target and cools the target by using cooling energy provided from the cooling device. In certain embodiment, the tip storage comprises a case; a storage hole disposed inside the case and into which the cooling tip is inserted. In some embodiments, each storage hole includes a storage space that has a shape corresponding to the shape of the cooling tip and a protection space extending from the storage space to an end of the storage hole. In some embodiments, the depth of the protection space is set to be larger than the length of the contact part protruding from the tip body to prevent the contact part from reaching the end of the storage hole.

In some embodiments, the different storage holes may be separable from each other. In some embodiments, the different storage holes may be distinguished from each other by markings.

System for Controlled Cooling

The present disclosure provides a cooling system and a cooling control system using the same, and more specifically, to the cooling system using a detachable cooling tip to safely cool down a target and the cooling control system for performing safe cooling.

It is contemplated that, prior to cosmetic or medical treatment on a target, the target may be cooled by using a cooling system to make the target anesthesia or painless, and at this time, a control method may be used to prevent any damage to the target by excessive cooling, etc.

The anesthesia state or the painless state means that the nerve of a target is temporarily paralyzed or nerve transmission is blocked prior to a procedure on the target. For example, a cooling system provides cooling energy by contacting a target surface, and the provided cooling energy makes the temperature of the nerve distributed below the target surface below the temperature at which the nerve is temporarily paralyzed or at which nerve transmission is blocked. In this way, the target may be in an anesthetic state or a painless state. In some embodiments, the cooling system may cool the target surface and the inside of the target to an appropriate temperature range to generate such an anesthetic or painless state for a certain period of time. In some embodiments, the cooling system may cool the target to directly destroy at least a portion of the target. For example, if the target is a part of the body including the skin spots (e.g., skin moles), warts, callus, etc., described above, the cooling system provides cooling energy to the target through the target surface, and the tissue in the target becomes necrotic or killed by the provided cooling energy. For another example, the cooling system may be used for treatment purposes such as inflammation relief, pigmented lesions, vascular lesions, and fat removal. Hereinafter, for convenience of explanation, a case in which the target is the eyeball and the cooling device, or the cooling tip contacts the eyeball surface in the cooling system to deliver cooling energy is described as a main embodiment, but the technical idea of the present specifications is not limited thereto, and it may be applied to any body part, including nerves.

Hereinafter, a cooling system (10) according to an embodiment of the present disclosure is described with reference to FIG. 1 and FIG. 2.

FIG. 1 shows a cooling system (10) according to an exemplary embodiment of the present disclosure. Referring to FIG. 1, the cooling system (10) includes a cooling device (1000), a cooling tip (2000), and a holder (3000).

The cooling device (1000) may cool a target by providing cooling energy to the target. Specifically, the cooling device (1000) may cool a target by generating cooling energy and providing it to the target as described later.

The cooling device (1000) may be associated with a cooling tip (2000) to cool a target.

The cooling device (1000) may be mounted on a holder (3000) before, after, or during use. For example, the cooling device (1000) may be mounted on the holder (3000) in an off state. For another example, the cooling device (1000) may be mounted on the holder (3000) for the user's convenience while power is supplied. In another embodiment, the cooling device (1000) may be mounted on the holder (3000) while reaching a desired standby temperature. In other embodiments, the cooling device (1000) may also reach a desired standby temperature without being mounted on the holder (3000).

The cooling device (1000) may be implemented as a portable device so that the user may easily carry it, or may be implemented in the form of a handpiece of a large device.

The cooling tip (2000) may receive cooling energy from the cooling device (1000) and transmit it to a target. Specifically, cooling energy generated by the cooling device (1000) may be transmitted to a target by the cooling tip (2000) contacting the target surface while the cooling tip (2000) is mounted on the cooling device (1000).

The cooling tip (2000) may be designed to be mounted and detached from the cooling device (1000). For example, when cooling different targets by using the cooling system (10), the cooling tip (2000) may be provided in a disposable or replaceable type so that the diseases or contaminants of one target are not transmitted or transferred to another target. For this purpose, the cooling tip (2000) may be mounted and detached from the cooling device (1000).

The cooling tip (2000) may be designed in a structure to prevent damage to the cooling device (1000) that may occur while being mounted on or detachable from the cooling device (1000) as described later.

The cooling device (1000) may be mounted on the holder (3000). Specifically, the holder (3000) is designed in a structure corresponding to the cooling device (1000) so that the user may mount the cooling device (1000) on the holder (3000) before, during, or after use of the cooling device (1000).

The holder (3000) may include a tester for checking the performance of the cooling device (1000) or the cooling tip (2000), as described later, and a shape for protecting the cooling device (1000) from external shocks. The shape of the holder (3000) will be described in detail later.

In the cooling system (10), the holder (3000) may be omitted (e.g., not included).

Figure 2:
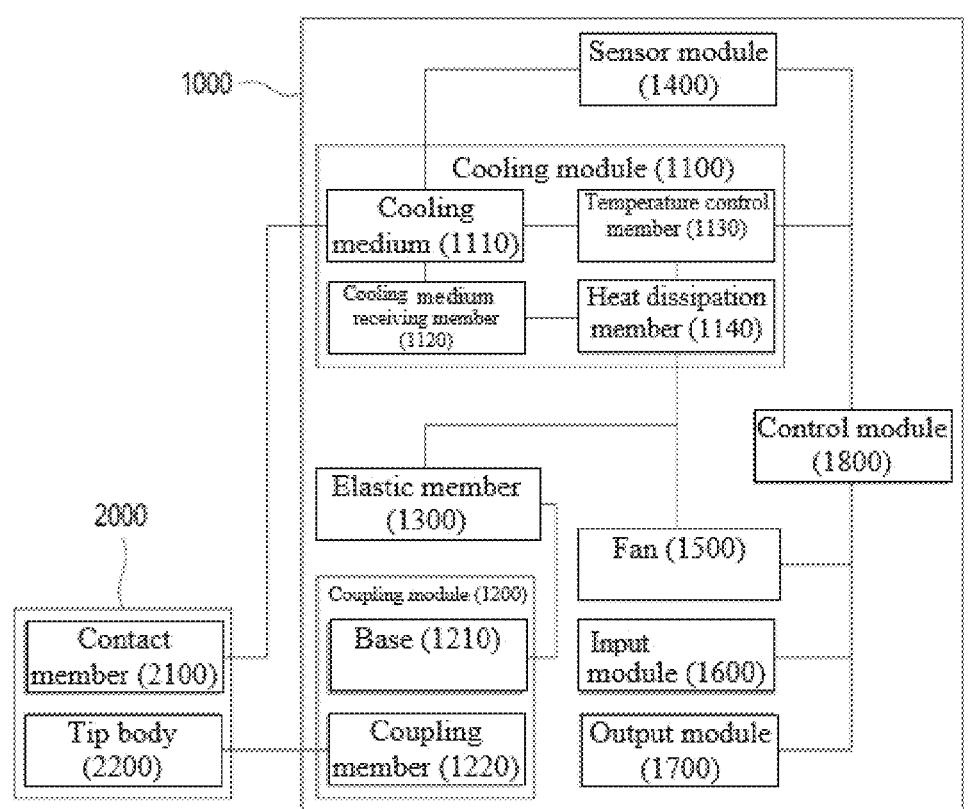
FIG. 2 shows a configuration of a cooling device and a cooling tip according to an exemplary embodiment of the present disclosure.

FIG. 2 shows a configuration of a cooling device (1000) and a cooling tip (2000) of an exemplary embodiment of the present disclosure.

Referring to FIG. 2, the cooling device (1000) includes a cooling module (1100), a coupling module (1200), an elastic member (1300), a sensor module (1400), a fan (1500), an input module (1600), an output module (1700) and a control module (1800).

In the following, each configuration of the exemplary embodiment will be described in detail.

The cooling module (1100) may generate and provide cooling energy transmitted to a target. Referring to FIG. 2, the cooling module (1100) may include a cooling medium (1110), a cooling medium receiving member (1120), a temperature control member (1130), and a heat dissipation member (1140). The cooling module (1100) may control the temperature of the cooling medium (1110) by using the temperature control member (1130) and provide cooling energy to the cooling tip (2000) through the cooling medium (1110).

The cooling medium (1110) may be thermally coupled to the cooling tip (2000) to provide cooling energy. Specifically, the cooling medium (1110) may provide cooling energy by making surface contact with the contact member (2100) of the cooling tip (2000). The cooling medium (1110) may be made of a material that has high thermal conductivity in order to efficiently transfer cooling energy. For example, the cooling medium (1110) may be made of gold (Ag), silver (Au), copper (Cu), aluminum (Al), or a combination thereof.

The cooling medium receiving member (1120) may receive the cooling medium (1110). For example, the cooling medium receiving member (1120) may surround the cooling medium (1110) and support the cooling medium (1110) in the cooling device (1000).

In addition, the cooling medium receiving member (1120) may be physically coupled with the tip body (2200) of the cooling tip (2000) so that the cooling medium (1110) is thermally coupled with the contact member (2100) of the cooling tip (2000).

The cooling medium receiving member (1120) may be made of a material that has a low thermal conductivity in order to prevent dispersion of cooling energy received by the cooling medium or the cooling energy of the cooling medium (1110). For example, the cooling medium receiving member (1120) may comprise a material such as plastic to prevent cooling loss of the cooling medium (1110).

The cooling medium receiving member (1120) may be in close contact with the cooling medium (1110) to prevent the cooling medium (1110) from contacting the air, thereby minimizing the amount of moisture condensed in the cooling medium upon cooling (1110).

The temperature control member (1130) may control the temperature of the cooling medium (1110). For example, the temperature control member (1130) may receive a control signal from the control module (1800) to be described herein to provide cooling energy or thermal energy to the cooling medium (1110).

The temperature control member (1130) may be implemented in various forms. For example, the temperature control member (1130) may include a thermoelectric element using a Peltier effect of receiving current and absorbing heat on one side and generates heat on the other side according to the applied current direction. In another example, the temperature control member (1130) may have a device or an element that uses a thermodynamic cycle such as a stirring cooler, a vapor compression refrigeration cycle, or Houle-Thomson method using expanding gas. In another example, the temperature control member (1130) may generate or provide cooling energy by using a coolant such as carbon dioxide or liquid nitrogen.

The temperature control member (1130) may be thermally coupled to the cooling medium (1110). For example, the temperature control member (1130) may provide cooling energy or thermal energy by making surface contact with at least a portion of the cooling medium (1110). Hereinafter, for ease of description, the majority of the descriptions feature cases is on the embodiment in which the temperature control member (1130) is a thermoelectric element using the Peltier effect, but the technical idea of the present invention is not limited thereto.

The heat dissipation member (1140) may discharge heat generated from or by the operation of the cooling module (1100) to the outside. For example, the heat dissipation member (1140) may receive heat generated as the temperature control member (1130) generates cooling energy and discharge it to the outside of the cooling device (1000).

The heat dissipation member (1140) may be thermally coupled with the temperature control member (1130) to receive heat energy. For example, the heat dissipation member (1140) may physically contact at least a portion of the temperature control member (1130) to receive heat energy generated from the temperature control member (1130). Specifically, when the temperature control member (1130) is a thermoelectric element, the heat dissipation member (1140) may make a surface contact with the surface of the temperature control member (1130) where heat is generated to receive heat from the temperature control member (1130) to discharge it to the outside.

The heat dissipation member (1140) may be made of a thermally conductive material such as metal in order to efficiently discharge heat. In some embodiments, the heat dissipation member (1140) comprises cylindrical shaped arrangement of fins. In some embodiments, a diameter of the fin ranges from 20 mm to 100 mm. In some embodiments, the length of the fin ranges from 40 mm to 200 mm. In some embodiments, the spacing between fins ranges from 1 mm to 5 mm.

The exemplary shape or coupling of the components included in the cooling module (1100) is described in detail herein.

The coupling module (1200) may refer to an element for the cooling tip (2000) of the cooling device (1000) to be coupled. For example, the cooling tip (2000) may be mounted on or detachable from the cooling device (1000) through the coupling module (1200).

The coupling module (1200) may support the internal configuration of the cooling device (1000). For example, the cooling medium (1110) of the cooling module (1100) and the cooling medium receiving member (1120) are inserted into the coupling module (1200) so that the cooling module (1100) may be disposed inside the cooling device (1000).

Furthermore, the coupling module (1200) may be connected to the cooling module (1100). For example, the cooling module (1100) may be physically mounted on, fixed, or coupled to the coupling module (1200). Specifically, the cooling module (1100) may be coupled to the coupling module (1200) through an elastic member (1300) to be described herein.

Referring back to FIG. 2, the coupling module (1200) may include a base (1210) and a coupling member (1220).

A base (1210) may refer to a body of the coupling module (1200). For example, the base (1210) may include a part which the cooling medium receiving member (1120) of the cooling module (1100) is inserted into and the cooling tip (2000) is mounted on. In addition, a coupling member (1220) for mounting and detaching the cooling tip (2000) may be fixed to the base (1210).

The base (1210) may refer to a means for physically connecting the elastic member (1300) to the coupling module (1200). For example, one end of the elastic member (1300) may be fixed to the base (1210) through at least one fixing pin.

The coupling member (1220) may refer to a means for attaching or detaching the cooling tip (2000) from the coupling module (1200). For example, the cooling tip (2000) may be mounted on the cooling device (1000) or separated from the cooling device (1000) according to the operation of the coupling member (1220). Specifically, the coupling member (1220) may include screw coupling, mechanical latch coupling, magnetic coupling, force fitting, etc.

The coupling module (1200) may include a plurality of fixing pins for coupling the elastic member (1300) and the coupling member (1220) to the base (1210).

The elastic member (1300) may connect the cooling module (1100) to the coupling module (1200). For example, one end of the elastic member (1300) may be connected to the coupling module (1200) and the other end may be connected to the cooling module (1100).

The elastic member (1300) may provide elastic force. For example, the elastic member (1300) may provide an elastic force in a direction opposite to the direction in which the cooling tip (2000) is mounted on the cooling device (1000) so that the cooling module (1100) may press the cooling tip (2000). For another example, the elastic member (1300) may provide an elastic force in the direction of the central axis of the cooling module (1100) so that the cooling module (1100) may be positioned within the cooling device (1000).

The elastic member (1300) may be replaced or omitted (e.g., removed or not present). For example, the cooling module (1100) may be physically coupled to the cooling device (1000) and fixed at a specific position in the cooling device (1000). Specifically, the cooling module (1100) may be fixed by a plurality of ribs provided in a body part of the cooling device (1000). Alternatively, the cooling module (1100) may be disposed inside the coupling module (1200) by being inserted into the coupling module (1200) and being fixed through screwing or the like.

The sensor module (1400) may detect physical characteristics of the cooling device (1000). Specifically, the sensor module (1400) may detect the temperature or electrical characteristics of the cooling medium (1110). For example, the sensor module (1400) may be directly or indirectly coupled to the cooling medium (1110) to measure the current, voltage, or temperature of the cooling medium (1110).

The sensor module (1400) may include a contact-type temperature sensor such as thermocouples, a resistance temperature detector (RTD), a thermistor, an IC temperature sensor, or non-contact type temperature sensor using an infrared ray or the like. Alternatively, the sensor module (1400) may include an analog or electronic circuit for measuring electrical characteristics such as current or voltage.

In addition, the sensor module (1400) may include a touch sensor or a pressure sensor to determine whether the cooling tip (2000) or the cooling device (1000) has contacted or is in contact with the target surface.

The sensor module (1400) may detect whether the cooling tip (2000) is mounted on or detached from the cooling device (1000). Alternatively and/or additionally, the sensor module (1400) may measure a pressure applied by the cooling device (1000) or the cooling tip (2000) to the target or the target surface. To this end, the sensor module (1400) may include a pressure sensor or a strain gauge. Alternatively and/or additionally, the sensor module (1400) may measure the distance between the device and the target or the target surface. In such embodiments the sensor module (1400) may include an sensor that can detect the distance, e.g., an infrared (IR) sensor, a proximity sensor, a distance sensor, etc.

The sensor module (1400) may provide the sensed physical characteristics of the cooling device (1000) to the control module (1800). For example, the sensor module (1400) may provide the control module (1800) with a signal which indicates (or reflects) a real-time temperature value, a voltage/current value of the cooling medium (1110), or a signal indicating whether the cooling tip (2000) is mounted on or detached from the cooling device (1000).

A fan (1500) may induce the flow of air in the cooling device (1000). For example, the fan (1500) receives a control signal from the control module (1800) to discharge internal heat generated from the cooling device (1000) as it produces cooling energy to the outside of the cooling device (1000).

The fan (1500) may be disposed adjacent to the heat dissipation member (1140). For example, the heat dissipation member (1140) may include a radiating fin to dissipate heat to the outside, and the fan (1500) may be disposed near the radiating fin to move air which is in contact with the radiating fin to the outside. In some embodiments, the cooling device (1000) includes a plurality of fans (1500) along the length of the cooling device (1000). In some embodiments, the plurality of fans (1500) increases the fin total area without increasing device diameter. In some embodiments, the heat dissipation member (1140) can be arranged at both sides of the fan(s).

An input module (1600) may receive the user input from the user. User input may be in various forms, including button input, key input, touch input, and voice input. For example, the input module (1600) is a comprehensive concept including an input means such as a button that the user may press, a touch sensor that detects the user's touch, a microphone that receives the user's voice input, and various types of input that detects or receives various types of user input.

An output module (1700) may output various types of information and provide it to the user. The output module (1700) is a comprehensive concept including a display that outputs an image, a speaker that outputs sound, a haptic device that generates vibration, and other various types of output means.

The control module (1800) may control the overall operation of the cooling device (1000). For example, the control module (1800) may load and execute a program for the operation of the cooling module (1100). In another example, the control module (1800) controls the fan (1500) to perform a heat dissipation function or controls the input module (1600) and the output module (1700) to generate and transmit a control signal according to the user input or provide specific information to the user.

In this example, the control module (1800) may be implemented as a device such as a central processing unit (CPU), a microprocessor, a processor core, a multiprocessor, or an ASIC according to hardware or software or a combination thereof. The control module (1800) may be provided in the form of an electronic circuit that performs a control function by processing electrical signals by hardware and may be provided in the form of a program or code for driving a hardware circuit using software.

In some embodiments, the cooling device (1000) may further include: a memory in which a control program loaded or executed at the control module (1800) is stored; and a power supply part for supplying power required for the operation of the cooling device (1000).

Referring back to FIG. 2, the cooling tip (2000) may include a contact member (2100) and a tip body (2000).

The contact member (2100) may receive cooling energy from the cooling device (1000). For example, the contact member (2100) may surface-contact the cooling medium (1110) of the cooling device (1000) to receive cooling energy.

The contact member (2100) may deliver cooling energy by contacting the target surface. For example, the contact member (2100) may contact the target surface to transmit cooling energy provided by the cooling device (1000).

The contact member (2100) may be made of a material that has high thermal conductivity in order to efficiently transfer cooling energy. For example, contact member (2100) may be made of gold (Ag), silver (Au), copper (Cu), aluminum (Al), or a combination thereof.

The contact member (2100) may be manufactured by using various processing methods. For example, the contact member (2100) may be manufactured through press processing. Specifically, the contact member (2100) may be manufactured by using shear processing, bending processing, deep drawing processing, or stretch expand processing for metal, and in this case, thin metal film such as 0.3 mm thick copper film (Cu) may be used. Accordingly, such processing methods enables facilitation of manufacturing of the contact member (2100) and allows and cooling energy to be transmitted more efficiently.

The contact member (2100) may be mounted on or detached from the cooling device (1000) through the tip body (2200). For example, the contact member (2100) may contact the target surface while being inserted into the tip body (2200) that is mounted and detached from the cooling device (1000).

The tip body (2200) may be mounted or detached from the cooling device (1000). For example, the tip body (2200) may include a connection portion at its end and may be mounted or detached from the coupling module (1200) of the cooling device (1000).

The tip body (2200) may be made of a material that has a low thermal conductivity so that cooling energy transmitted from the cooling device (1000) to the contact member (2100) is not dispersed. For example, the tip body (2200) may include a material such as plastic to prevent cooling loss of the contact member (2100).

The tip body (2200) may be made of a material that has specific properties. For example, the tip body (2200) may be made of a material that is not deformed at about 130° C. or higher to enable sterilization through a process such as autoclave. For another example, the tip body (2200) may be made to be deformed during the above-described sterilization process for the purpose of being used as a one-time use. Specifically, the tip body (2200) may include a material that is deformed at the above-described autoclave process temperature of 130° C.*so that it is not reused by sterilization, and preferably, the tip body (2200) may be made of polyethylene terephthalate (PET) material.]

Hereinafter, an exemplary process through which the cooling system (10) cools a target is described in detail with reference to FIG. 3.

Figure 3:
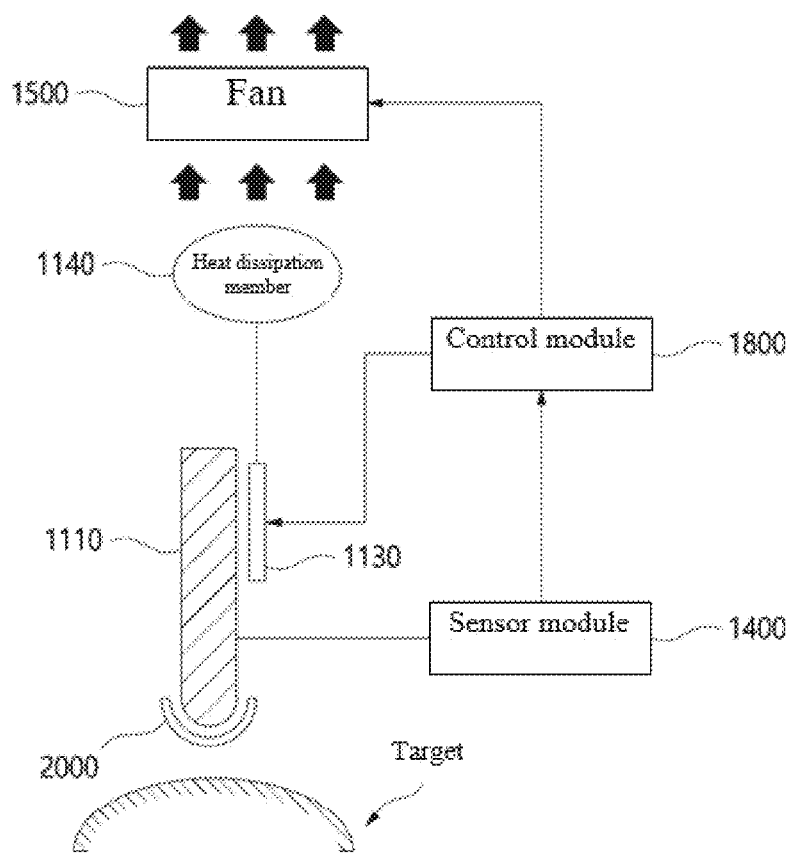
FIG. 3 shows the process of cooling a target in a cooling system according to an exemplary embodiment of the present disclosure.

FIG. 3 shows an exemplary process of cooling a target in the cooling system (10) according to an exemplary embodiment of the present invention.

Referring to FIG. 3, the control module (1800) controls the temperature of the cooling medium (1110) by controlling the temperature control member (1130) and the fan (1500), and the cooling medium (1110) may cool a target by providing cooling energy to the target surface through the cooling tip (2000). Hereinafter, the process in which the cooling function is performed will be described in detail.

The control module (1800) may control the temperature control member (1130) to provide cooling energy to the cooling medium (1110) so as to adjust the temperature of the cooling medium (1110) to a preset (or predetermined) temperature. For example, the control module (1800) may control the temperature of the cooling medium (1110) at a temperature for cooling by controlling an output of the temperature control member (1130) to increase or decrease the temperature of the cooling medium (1110). An exemplary method of controlling the temperature of the cooling medium (1110) by the control module (1800) is described below.

The sensor module (1400) may obtain temperature information by measuring the temperature of the cooling medium (1110) that changes as cooling energy is delivered to the cooling medium (1110) and provide the obtained temperature information to the control module (1800). The temperature information obtained by the sensor module (1400) may refer to temperature information relating to the cooling tip (2000) that is thermally coupled to the cooling medium (1110). The temperature information acquired by the sensor module (1400) may include information about the temperature of a component inside the cooling device (1000) or information about the standby temperature of the cooling device (1000). In this case, the sensor module (1400) may include a plurality of sensors for obtaining various temperature information.

The control module (1800) may generate a control signal for controlling the temperature control member (1130) based on temperature information obtained from the sensor module (1400).

For example, a control module (1800) may use feedback control to control the power applied to a temperature control member (1130) by using temperature information pertaining to a cooling medium (1110) obtained from a sensor module (1400). Specifically, the control module (1800) may control the temperature of the cooling medium (1110) by using the following PID (Proportional Integral Differential) control equation as shown below.

$$P(t) = C_p error(t) + C_i \int_0^t error(t)dt + C_d \frac{d(error(t))}{dt}$$

Here, P(t) means an output value or a control value of a signal that the control module (1800) uses to control the temperature control member (1130), and error(t) refers to the difference between the temperature of the cooling medium (1110) that the control module (1800) will control and the temperature of the cooling medium (1110) measured by the sensor module (1400), and Cp, Ci, and Cd refer to a gain value or gain selected in the tuning process. On the other hand, it goes without saying that P, PI, and PD control can be used since each term is omitted from the above control equation.

For another example, the control module (1800) may provide to the control temperature control member (1130) the electric power corresponding to particular temperature of the cooling medium (1110) in consideration of the thermal conductivity of the cooling tip (2000), the contact area between the cooling tip (2000) and the target surface, the contact area between the temperature control member (1130) and the cooling medium (1110), etc. For example, the control module (1800) may have a time difference in providing power to the temperature control member (1130) in order to compensate for a time delay due to the heat capacitance of the cooling medium (1110).

The control module (1800) may perform an auxiliary function in cooling a target based on the temperature information obtained from the sensor module (1400). For example, the control module (1800) may control a preliminary cooling time (or a standby contact time), the user input standby time (or a standby trigger time), and a cooling execution time (or a cooling time), etc. by using temperature information of the cooling medium (1110) obtained from the sensor module (1400). For another example, the control module (1800) may operate or stop the cooling device (1000) in order to prevent excessive cooling of the target by using the temperature information obtained from the sensor module (1400) or by detecting whether the cooling device (1000) is operating abnormally. An exemplary cooling method for a target will be described in detail later.

The cooling medium (1110) may contact target surface through the cooling tip (2000). The cooling tip (2000) is for replacement and is replaced every time a procedure such as cooling anesthesia is performed to prevent contaminants or harmful substances from penetrating into a target so that the target may be hygienically sterilized.

The heat dissipation member (1140) and the fan (1500) may discharge heat generated from the temperature control member (1130) to the outside. For example, the heat dissipation member (1140) may make contact with one surface of the temperature control member (1130) to absorb heat generated by the temperature control member (1130) providing cooling energy to the cooling medium (1110), and the fan (1500) may discharge heat absorbed by the heat dissipating member (1140) to the outside of the cooling device (1000) by allowing outside air or internal air to pass by the heat dissipating member (1140) in one direction. In this case, the heat dissipation member (1140) may include a plurality of radiating fins that has a relatively large contact area with air in order to increase heat dissipation efficiency, and the fan (1500) is disposed adjacent to the heat dissipation fins so that heat is mainly discharged from the radiating fins.

Here, heat dissipation from the heat dissipation member (1140) may be performed in a region spaced apart from the cooling medium (1110). For example, the heat dissipation member (1140) may include a heat pipe that has a predetermined length and thermally coupling the radiating fins and the temperature control member (1130). As a result, the cooling medium (1110) is less affected by the heat absorbed by the heat dissipating member (1140) from the temperature control member (1130), thereby enabling efficient cooling.

Hereinafter, the structure of an exemplary cooling device (1000) is described with reference to FIGS. 4 to 6.

Figure 4:
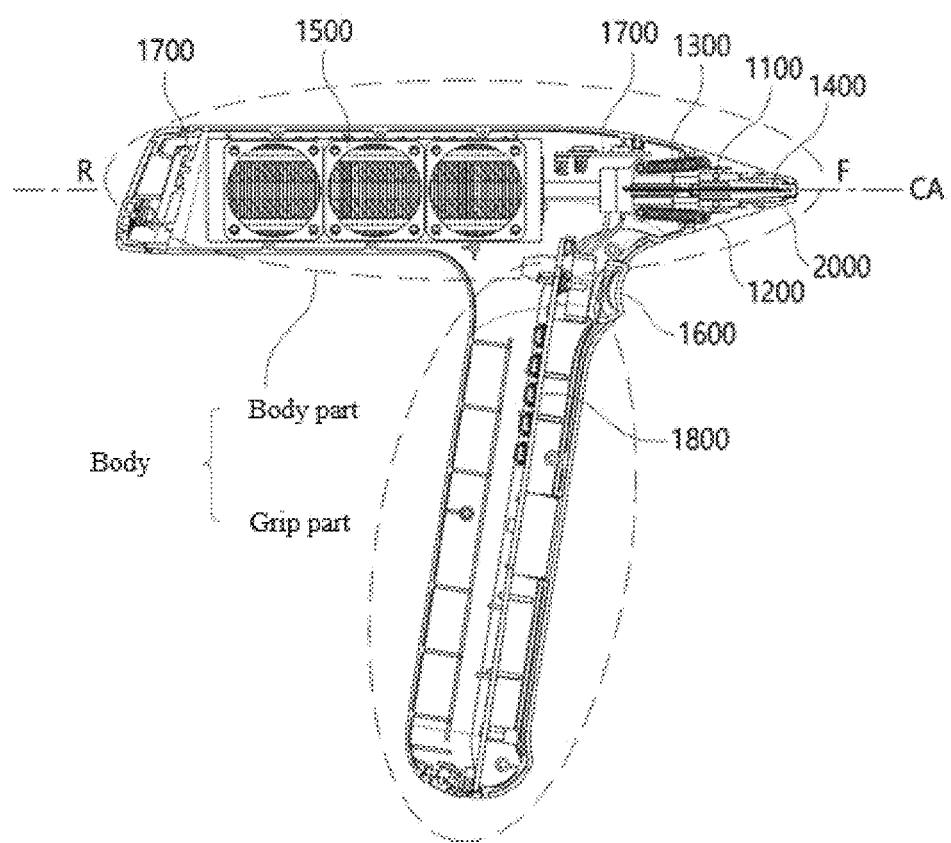
FIG. 4 shows an internal configuration of a cooling device according to an exemplary embodiment of the present disclosure.

FIG. 4 shows an internal configuration of the cooling device (1000) according to an embodiment of the present disclosure. Referring to FIG. 4, the cooling device (1000) may include a body comprising a body part and a grip part, and components of the cooling device (1000) described above may be disposed in the body part or the grip part.

The body of the cooling device (1000) may be divided into a body part and a grip part. For example, the body of the cooling device (1000) may include a body part on which the cooling tip (2000) is mounted and a grip part that may be gripped by the user. Here, the body part and the grip part may be implemented integrally (e.g., an all-in-one embodiment) or may be physically separated but combined through assembly to form the cooling device (1000).

A cooling module (1100), a coupling module (1200), an elastic member (1300), a sensor module (1400), a fan (1500), and an output module (1700) may be disposed inside the body part. Specifically, referring to FIG. 4 again, a cooling module (1100), a coupling module (1200), an elastic member (1300), a sensor module (1400), a fan (1500), and an output module (1700) may be disposed inside the body part along the central axis (CA). For example, the cooling module (1100), the coupling module (1200), the elastic member (1300), and the sensor module (1400) are disposed close to the front end (F) of the body part, and the fan (1500) is disposed close to a rear end (R) of the body part. The output module (1700) includes a plurality of output devices and may be disposed close to the front end (F) or the rear end (R) of the body, respectively.

In this example, the central axis (CA) may refer to an axis formed in a longitudinal direction passing through the center of the body part or an axis parallel thereto.

In this example, the coupling module (1200) may constitute at least a part of the body. For example, the coupling module (1200) may be formed in the front end (F) of the body part of the cooling device (1000). Alternatively, the coupling module (1200) may be implemented in a form of being coupled to the body part.

In this example, the cooling tip (2000) may be mounted on the body. For example, the cooling tip (1400) may be mounted or detached from the cooling device (1000) at the front end (F) of the body part. Specifically, the cooling tip (1400) may be mounted on the cooling device (1000) or detached from the cooling device (1000) through the coupling module (1200) formed at the front end (F) of the body part.

The control module (1800) may be disposed inside the grip part. Alternatively, the input module (1600) may be disposed inside (e.g., within) or outside (e.g., on the exterior of) the grip part. For example, referring again to FIG. 4, the control module (1800) may be disposed in the grip part along the lengthwise direction of the grip part. In addition, an input module (1600), such as a button for a timer operation, may be disposed at a portion where the user's finger is located according to the user's grip. Accordingly, the user may easily control the operation of the cooling device (1000) by pressing the button while gripping the cooling device (1000) to operate the timer. In addition, in some embodiments, the grip part may include a power supply part and a charging port for supplying electric power to the cooling device (1000).

The arrangement of the components of the cooling device (1000) in the body part and the grip part of the cooling device (1000) is not limited to the description above.

Figure 5:
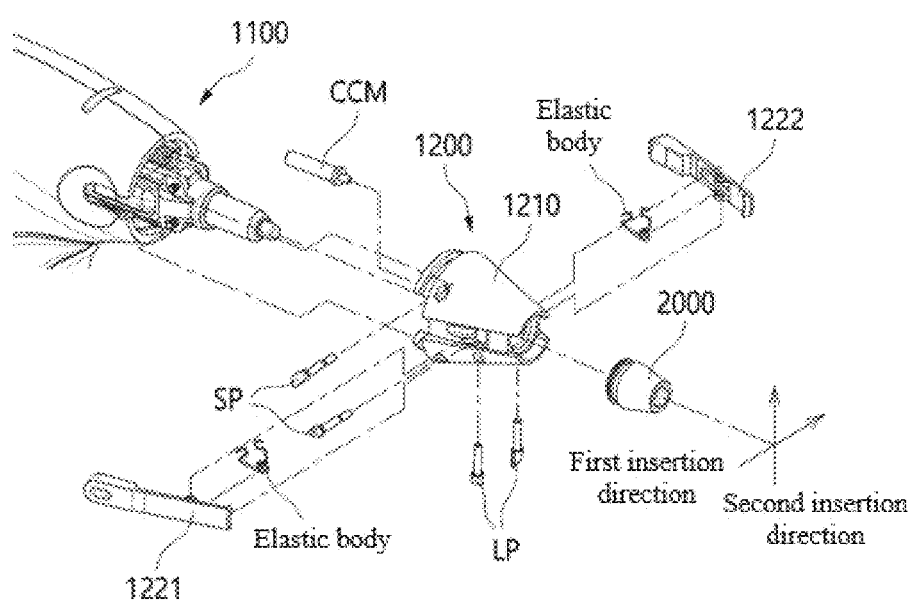
FIG. 5 shows a coupling module according to an exemplary embodiment of the present disclosure.

FIG. 5 shows a coupling module (1200) according to an exemplary embodiment of the present disclosure.

Referring to FIG. 5, the coupling module (1200) may include a base (1210), a coupling member (1220), a coupling member fixing pin (LP), an elastic member fixing pin (SP), and a mounting confirmation member (CCM). The cooling tip (2000) is mounted on and detached from the coupling module (1200) through the coupling member (1220), which includes a first coupling member (1221) and a second coupling member (1222), and one end of the elastic member (1300) may be fixed to the coupling module (1200) through the elastic member fixing pin (SP).

At least a portion of the cooling module (1100) may be inserted into the base (1210). For example, the base (1210) includes a hollow corresponding to the cooling module (1100) therein, and the cooling module (1100) is inserted into a hollow of the base (1210) and passes through the base (1210), thereby the cooling medium (1110) may be thermally coupled to the contact member (2100) of the cooling tip (2000). In this example, a hollow of the base (1210) may have a shape and size corresponding to those of the cooling medium receiving member (1120) in order to be inserted into the cooling module (1100).

The base (1210) may include a space in which at least a portion of the coupling member (1220) or a portion of the elastic member (1300) are disposed. For example, the base (1210) may include a space in which the coupling member (1220) is disposed outside thereof and a space in which the elastic member (1300) is disposed inside thereof. In this example, since the elastic member (1300) may be physically connected to the cooling module (1100), the space in which the elastic member (1300) is disposed may be implemented in an expanded form from the hollow of the base (1210) into which the cooling module (1100) is inserted.

The base (1210) may include an insertion hole into which fixing pins for fixing one end of the coupling member (1220) or the elastic member (1300) are inserted. For example, referring again to FIG. 5, the base (1210) may include a plurality of insertion holes into which the coupling member fixing pins (LP) and the elastic member fixing pins (SP) are inserted.

Specifically, the base (1210) may include: the initial insertion hole into which the elastic member fixing pin (SP) is inserted in the initial insertion direction perpendicular to the central axis (CA); and a second insertion hole into which the coupling member fixing pin (LP) is inserted in a second insertion direction different from the first insertion direction.

In this example, the first insertion hole into which the elastic member fixing pin (SP) is inserted and the second insertion hole into which the coupling member fixing pin (LP) is inserted may be disposed so that they don't overlap each other in the base (1210). For example, the first insertion hole may be formed closer to a front end (F) or further to a rear end (R) of the base (1210) than the second insertion hole.

The elastic member fixing pin (SP) and the coupling member fixing pin (LP) may be inserted into the base (1210) in a direction different from the described first and second insertion directions, respectively, and the number of the elastic member fixing pin (SP) and the coupling member fixing pin (LP) may vary depending on the number of the coupling member (1220) and the elastic member (1300). Also, the elastic member fixing pin (SP) and the coupling member fixing pin (LP) may be implemented in various forms such as a parallel pin, taper pin, split pin, spring pin, screw, etc.

The coupling member (1220) may be coupled to the base (1210) to mount the cooling tip (2000) on the cooling device (1000) or detach the mounted cooling tip (2000) from the cooling device (1000). For example, the coupling member (1220) may include a latch part, and the cooling tip (2000) may be mounted on the cooling device (1000) by the latch part hooked to a groove included in the cooling tip (2000). In addition, when the latch of the coupling member (1220) is separated from the groove of the cooling tip (2000) while the cooling tip (2000) is mounted on the cooling device (1000), the cooling tip (2000) may be detached from the cooling device (1000). For the operation pertaining to the coupling member (1220), the coupling module (1200) may further include an elastic body (e.g., a spring). For another example, when the coupling member (1220) is fixed to the base (1210) together with an elastic body, one end of the coupling member (1220) is applied with an external force via the user input or the like, resulting in the coupling member (1220) being rotated in one direction and the external force being eliminated. When this happens, the coupling member (1220) may rotate to its original state by the elastic body. The operation of the exemplary coupling member (1220) is described in detail below.

The coupling member (1220) may be implemented in plural. For example, referring again to FIG. 5, the base (1210) includes the first coupling member (1221) and a second coupling member (1222), and the cooling tip (2000) may be mounted on or detached from the coupling module (1200) through the first coupling member (1221) and the second coupling member (1222).

The coupling member (1220) may be fixed (e.g., substantially immobilized) to the base (1210) through the coupling member fixing pin (LP). For example, the coupling member (1220) which is disposed on an outer side of the base (1210) may be fixed in the base (1210) when the coupling member (1220) is inserted into the base (1210) as the coupling member fixing pin (LP) penetrates the coupling member (1220).

One end of the elastic member (1300) may be fixed to the base (1210) through an elastic member fixing pin (SP). For example, in a state in which one end of the elastic member (1300) is disposed inside the base (1210), the elastic member fixing pin (SP) penetrates the one end of the elastic member (1300) and is inserted into the base (1210), thereby fixing one end of the 1300 to the base (1210).

It has been described that the coupling member (1220) and the elastic member (1300) are fixed to the base (1210) by using the coupling member fixing pin (LP) and the elastic member fixing pin (SP), respectively, but the technical idea of the present disclosure is not limited thereto. The coupling member (1220) and the elastic member (1300) may be fixed or coupled to the base (1210) by using force fitting, screwing, latching, or magnetic coupling.

A mounting confirmation member (CCM) may detect whether the cooling tip (2000) is mounted on the coupling module (1200). For example, as shown in FIG. 5, the mounting confirmation member (CCM) is disposed inside the coupling module (1200) to detect that the cooling tip (2000) is mounted on the coupling module (1200) and provide information regarding the mounting of the cooling tip (2000) to the control module (1800). The mounting confirmation member (CCM) may be comprising a switch operated by an external force, a pressure sensor, a touch sensor, or a combination thereof to detect whether the cooling tip (2000) is mounted. The mounting confirmation member (CCM) may be attached to the member receiving the cooling medium (1120).

As described above, the coupling module (1200) may include a coupling member (1220) to allow the cooling tip (2000) to be detachable and be connected to the module (1100) to allow the cooling to be disposed and move inside the cooling device (1000). As such, the coupling module (1200) performs various roles, thereby optimizing the arrangement of the elements of the cooling device (1000), and further improving the assembling of the cooling device (1000). In addition, the coupling module (1200) allows the user to easily and quickly detach the cooling tip (2000) from the cooling device (1000) so that the cooling of a target may be immediately stopped in an emergency.

Figure 6:
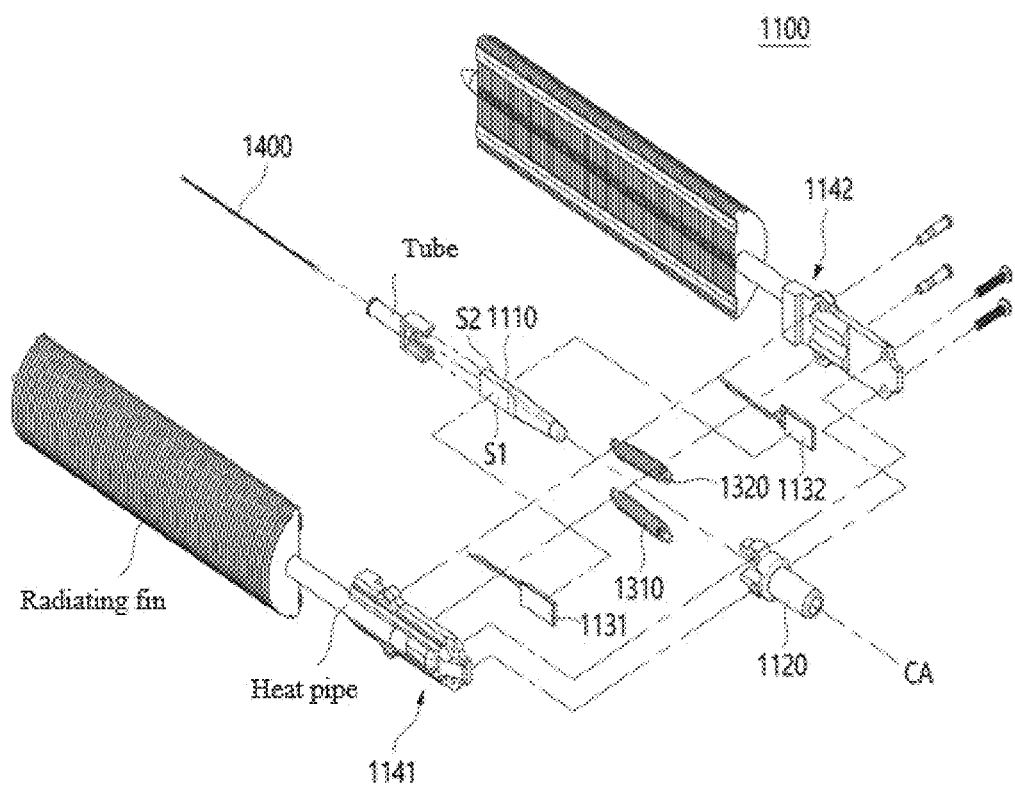
FIG. 6 is a cooling module according to an exemplary embodiment of the present disclosure.

FIG. 6 shows a cooling module (1100) according to an exemplary embodiment of the present disclosure.

Referring to FIG. 6, the cooling module (1100) may include a cooling medium (1110), a cooling medium receiving member (1120), a temperature control member (1130), a heat dissipation member (1140), which, in some embodiments, comprises a first heat dissipation member (1141) and a second heat dissipation member (1142), and a tube.

The cooling medium (1110) may be thermally coupled to the temperature control member (1130). For example, referring to FIG. 6 again, the cooling medium (1110) may include the first surface (S1) in contact with one surface of the first temperature control member (1131) and a second surface (S2) in contact with one surface of the second temperature control member (1132). The cooling medium (1110) may receive cooling energy from the first and second temperature control members (1131, 1132) through the first surface (S1) and the second surface (S2).

In this case, the cooling medium (1110) and the temperature control member (1130) may be implemented in a shape for efficiently exchanging cooling energy or thermal energy. For example, at least a portion of the cooling medium (1110) and the temperature control member (1130) may be implemented in a rectangular parallelepiped shape for surface contact. The shapes of the cooling medium (1110) and the temperature control member (1130) are not limited to the described rectangular parallelepiped and may be implemented in various shapes for surface contact.

The cooling medium receiving member (1120) may receive the cooling medium (1110). For example, at least a portion of the cooling medium (1110) may be inserted into the cooling medium receiving member (1120) to penetrate the cooling medium receiving member (1120). In this case, when the cooling medium (1110) penetrates in close contact with the cooling medium receiving member (1120) or passes through the cooling medium (1110), a sealing member may be used in order to minimize moisture formed when the cooling medium (1110) is cooled below the dew point. In addition, moisture condensation may be minimized by applying a hydrophobic coating on the surface of the cooling medium (1110).

The cooling medium receiving member (1120) may include a coupling hole for coupling with the heat dissipation member (1140). For example, the cooling medium receiving member (1120) may include at least one coupling hole corresponding to at least one screw hole formed in the heat dissipation member (1140) to be described later to mechanically couple with the heat dissipation member (1140).

The temperature control member (1130) may be fixed in a thermally coupled state with the cooling medium (1110) and the heat dissipation member (1140). For example, referring again to FIG. 6, when the first temperature control member (1131) is disposed between the cooling medium (1110) and the first heat dissipation member (1141), and when the second temperature control member (1132) is disposed between the cooling medium (1110) and the second heat dissipation member (1142), the first heat dissipation member (1141) and the second heat dissipation member (1142) may be combined to press the first and second temperature control members (1131, 1132), thereby fixing the first temperature control member (1131) and the second temperature control member (1132) to the cooling medium (1110) through surface contact.

In this case, when the temperature control member (1130) includes one surface and another surface that absorbs heat or dissipates heat according to the direction of the applied current, one surface of the temperature control member 1130 may contact the cooling medium (1110) and the other surface of the temperature control member (1130) may contact the heat dissipation member (1140). In this case, the temperature control member (1130) may transmit cooling energy to the cooling medium (1110) through one surface, and the heat energy generated as a response to the generation of cooling energy may be transmitted to the heat dissipation member (1140) through the other surface of the temperature control member (1130).

As described above, the cooling medium (1110) receives cooling energy according to the operation of the temperature control member (1130), and the heat dissipation member (1140) receives thermal energy corresponding to the cooling energy and discharges it to the outside of the cooling device (1000). Thus, the cooling efficiency of the cooling device (1000) may be increased, and durability of the cooling device (1000) may be improved.

When the temperature control member (1130) stops or cancels its operation, the heat dissipation member (1140) may have different physical properties from those of the cooling medium (1110) in order to increase the lowered temperature of the cooling medium (1110). For example, the heat dissipation member (1140) may have a larger heat capacity than that of the cooling medium (1110), which is preferably twice or more than the cooling medium (1110). Specifically, the heat dissipation member (1140) may be made of the same material as that of the cooling medium (1110) but may be implemented to have a large mass. Alternatively, the heat dissipation member (1140) may be formed of a material that has a greater specific heat than that of the cooling medium (1110). Accordingly, when the operation of the cooling device (1000) is stopped, heat transfer from the cooling medium (1110) to the heat dissipating member (1140) is accelerated so that the temperature of the target thermally coupled through the cooling medium (1110) and the cooling tip (2000) may rise quickly and safely.

The heat dissipation member (1140) may be connected to the cooling medium receiving member (1120). For example, referring to FIG. 6 again, the cooling medium receiving member 1120 is disposed between the first heat dissipation member (1141) and the second heat dissipation member (1142). A coupling means such as a fixing pin or a screw is then inserted into a screw hole of the first and second heat dissipation members (1141, 1142) and a coupling hole of the cooling medium receiving member (1120), thereby coupling the heat dissipation member (1140) and a cooling medium receiving member (1120).

The heat dissipation member (1140) may include a heat pipe and a plurality of radiating pins to dissipate the heat energy provided from the temperature control member (1130) to a location spaced apart from the cooling medium (1110) at a certain distance.

As described above, the heat dissipation member (1140) may be divided into a coupling part coupled to the cooling medium receiving member (1120), a heat pipe for moving received heat energy, and a heat dissipation part including a plurality of radiating fins. The heat dissipation member (1140) receives heat energy from the coupling part, moves the heat energy received through the heat pipe, and discharges heat to the outside through the heat dissipation part. In this case, the coupling part, the heat pipe, and the heat dissipation part may be integrated in a way that makes them not physically separated. It also may be physically separated to form the heat dissipation member (1140) by assembling.

The heat dissipation member (1140) may receive a tube, which will be described later. For example, when the first and second heat dissipation members (1141, 1142) are coupled, the first heat dissipation member (1141) and the second heat dissipation member (1142) respectively include a groove that corresponds to the tube so that a hollow space into which the tube is inserted is formed.

The other end of the elastic member (1300) may be fixed to the heat dissipation member (1140). For example, referring to FIG. 6 again, the first heat dissipation member (1141) and the second heat dissipation member (1142) may be coupled through a plurality of coupling pins or coupling screws, the other end of the first elastic member (1310) and the other end of the second elastic member (1320) may be fixed to the coupling pins or coupling screws. As a result, one end of the elastic member (1300) is connected to the body, and the other end of the elastic member (1300) is connected to the cooling module (1100). Thus, the cooling module (1100) may move in the body due to the elasticity of the elastic member (1300).

The other end of the elastic member (1300) may be fixed to other components of the cooling module (1100) in addition to the heat dissipation member (1140). However, when the other end of the elastic member (1300) is fixed to the cooling medium (1110), cooling energy loss of the cooling medium (1110) may occur, and when the other end of the elastic member (1300) is connected to the heat dissipation member (1140), it may support heat radiation. As a result, the latter method is preferred.

The sensor module (1400) may be inserted into the cooling medium (1110). For example, the sensor module (1400) may be inserted into the cooling medium (1110 along the central axis (CA) to obtain temperature information of the cooling medium (1110) in real time. The sensor module (1400) may measure the temperature of the cooling medium (1110) by contacting or non-contacting the cooling medium (1110) without being inserted into the cooling medium (1110).

The cooling module (1100) may include a tube. This tube may let a power supply line needed for energy generation or a sensor module (1400) pass through. For example, a wire for supplying power to the temperature control member (1130) or a temperature sensor for measuring the temperature of the cooling medium (1110) may be disposed to pass through the tube. In this case, the tube may be made of a material such as plastic that has low thermal conductivity for the effective insulation of the cooling medium (1110).

In the description above, the cooling module (1100) is implemented as a plurality of temperature control members (1130) and a plurality of heat dissipation members (1140) are coupled symmetrically with respect to the central axis (CA) of the cooling module (1100). However, the technical idea of the present invention is not limited thereto. For example, a temperature control member (1130) and a heat dissipation member (1140) sequentially disposed on one surface of the cooling medium (1110) and the described cooling medium (1110) is inserted into the cooling medium receiving member (1120). Likewise, various structures in which the cooling module (1100) provides cooling energy to the cooling medium (1110) and discharges heat may be implemented.

Hereinafter, the process of mounting and detaching a cooling tip (2000) in the cooling device (1000) is described with reference to FIGS. 7 to 11.

Figure 7:
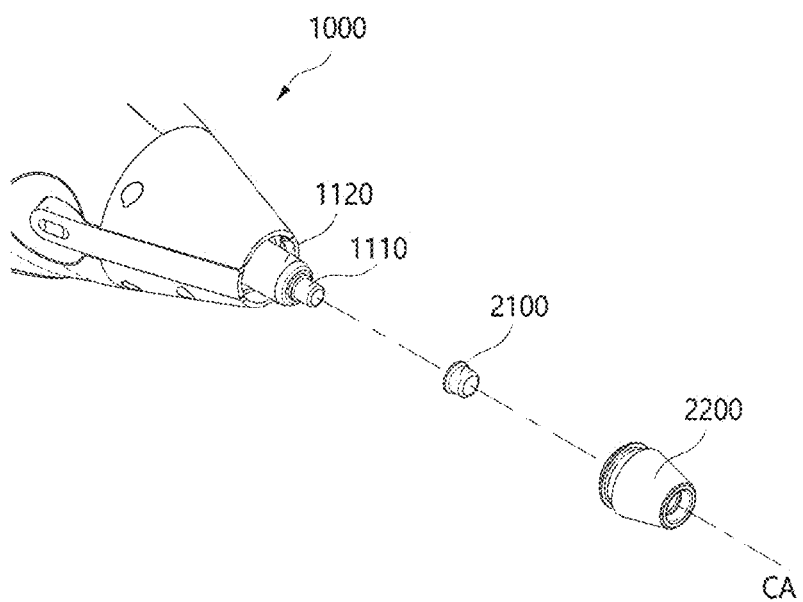
FIG. 7 shows a path of a cooling tip mounting on and being detached from a cooling device according to an exemplary embodiment of the present disclosure.

FIG. 7 shows a path of a cooling tip (200) mounting on and being detached from a cooling device (1000) according to an embodiment of the present disclosure.

Referring to FIG. 7, the cooling tip (2000) may be mounted on the cooling device (1000) or detached from the cooling device (1000). In this embodiments, the cooling tip (2000) includes the contact member (2100) and the tip body (2200). In addition, in the cooling tip (2000), the contact member (2100) may be mounted on the tip body (2200) or detached from the tip body (2200). For example, the cooling tip (2000) may be mounted on the cooling device (1000) along the central axis (CA). At this time, the cooling tip (2000) may be mounted on the cooling device (1000) or detached from the cooling device (1000) while the contact member (2100) is fitted or force fitted to the middle of the tip body (2200).

The cooling tip (2000) may be mounted on the cooling device (1000) to improve cooling energy transfer efficiency. For example, when the cooling tip (2000) is mounted on the cooling device (1000), the cooling medium (1110) physically contacts the contact member (2100) and may be connected with the tip body (2200) through the cooling medium receiving member (1120). In other words, the cooling medium (1110) may provide cooling energy intensively to the contact member (2100) of the cooling tip (2000).

Figure 8:
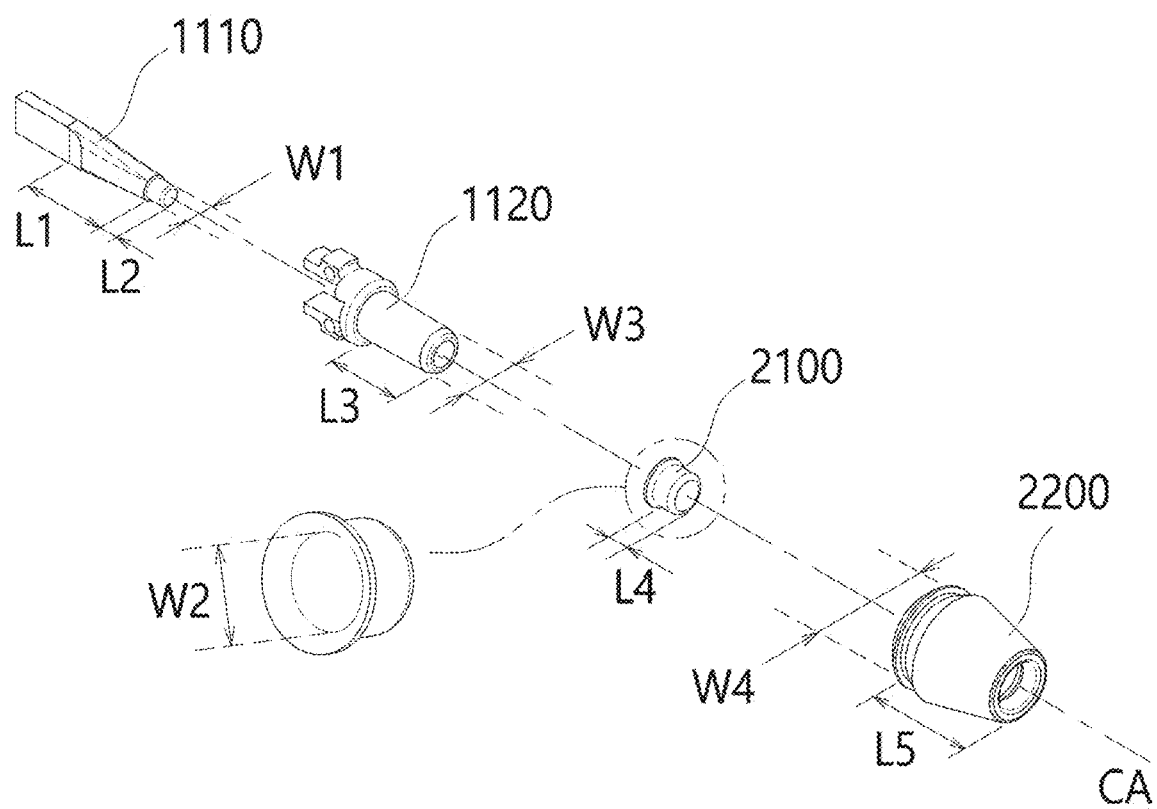
FIG. 8 shows a cooling tip being mounted on a cooling module according to an exemplary embodiment of the present disclosure.

FIG. 8 shows a cooling tip that is mounted on a cooling module (2000) according to an exemplary embodiment of the present disclosure.

Referring to FIG. 8, the tip body (2200) and the contact member (2100) may be detached from the cooling medium receiving member (1120) and the cooling medium (1110) along the central axis (CA). As described above, the cooling medium (1110), the cooling medium receiving member (1120), the contact member (2100), and the tip body (2200) may have shapes corresponding to each other in order to improve the cooling efficiency and durability of the cooling device (1000), The cooling medium (1110) may include an insertion part inserted into the cooling medium receiving member (1120) and a protruding part protruding from the cooling medium receiving member (1120). Referring back to FIG. 8, the cooling medium (1110) may include an insertion part that has the first length (L1) and a protruding part that has a second length (L2) and the first width (W1). In this case, the insertion part may be implemented in a tapered shape in which a cross section of one end is a square, a cross section of the other end is a circle, and the width becomes narrower from one end to the other end. The protruding part may be implemented in a cylindrical shape.

The cooling medium receiving member (1120) may include a receiving part through which the insertion part of the cooling medium (1110) passes. For example, the cooling medium receiving member (1120) may include a receiving part that has a third length (L3), a third width (W3) and a hollow therein. In this example, the third length (L3) corresponds to the first length (L1) of the insertion part of the cooling medium (1110) so that the protruding part of the cooling medium (1110) protrudes from the cooling medium receiving member (1120) by a predetermined length, and the hollow may have a shape that corresponds to the shape of the insertion part of the cooling medium (1110).

The contact member (2100) may have a shape that corresponds to the protruding part of the cooling medium (1110). For example, referring to FIG. 8 again, when the protruding part of the cooling medium (1110) has a cylindrical shape that has the initial width (W1) and a second length (L2), the contact member (2100) may have an inner space of a cylindrical shape that has a second width (W2) greater than or equal to the first width (W1) and a fourth length (L4) shorter than or equal to the second length (L2), in order to create a vertical pressure between the cooling medium (1110) and the contact member (2100). In this example, as the second length (L2) of the protruding part of the cooling medium (1110) is greater than or equal to the fourth length (L4) of the inner space of the contact member (2100), the cooling medium (1110) may press contact member 2100 to firmly fix it to the tip body (2200). In addition, since the first width (W1) of the protruding part of the cooling medium (1110) is less than or equal to the second width (W2) of the inner space of the contact member (2100), the cooling tip (2000) may be easily mounted on or detached from the cooling device 1000 and damage to the cooling medium (1110) may be prevented during installation and detachment. If the first width (W1) of the protruding part of the cooling medium (1110) is less than or equal to the second width (W2) of the inner space of the contact member (2100), one surface of the contact member (2100) contacting the target surface may have a larger area than one surface of the protruding part of the cooling medium (1110) in contact with the contact member (2100).

The tip body (2200) may have a shape that corresponds to the cooling medium receiving member (1120). For example, when the cooling medium accommodating member (1120) has a cylindrical shape that has a third length (L3) and a third width (W3), the tip body (2200) may have an inner space that has a fourth width (W4) greater than or equal to the third width (W3), and that has a fifth length (L5) that is shorter than the third length (L3). In this example, since the third width (W3) corresponds to the fourth width (W4), or the inner diameter of an opening of the tip body (2200) corresponds to the outer diameter of the cooling medium receiving member (1120), the cooling medium (1110) does not contact the inner circumferential surface of the contact member (2100) when the cooling tip (2000) is mounted on or detached from the cooling device (1000) in a state in which the central axis of the cooling medium (1110) and the central axis of the contact member (2100) correspond to each other. Thus, the cooling medium (1110) may be prevented from being worn or damaged. In addition, the fifth length (L5) may be configured so that the coupling force applied by the elastic member (1300) may be concentrated between the cooling medium (1110) and the contact member (2100) of the cooling tip (2000), and accordingly, the efficiency of heat transfer between the cooling medium (1110) and the contact member (2100) of the cooling tip (2000) may be increased.

In order to prevent damage to the cooling medium (1110) due to the mounting of the cooling tip (2000), the protruding part of the cooling medium (1110), contacting the contact member (2100) of the cooling tip (2000), may be coated with a wear-resistant material. For example, it may be coated with a metal such as nickel or chromium. Alternatively, a coating member may be included between the cooling tip (2000) and the cooling medium (1110). In this case, the coating member may be made of a softer material than that of the contact member (2100) of the cooling tip (2000). Specifically, the coating member may have a hardness of less than 2.5 Mohs of hardness, and preferably may have a hardness of 2 or less in Mohs of hardness.

In addition, the cooling medium (1110), the cooling medium receiving member (1120), the contact member (2100), and the tip body (2200) described above are not limited to the described shape or size. For example, the cross section of the protruding part of the cooling medium (1110) and the cross section of the contact member (2100) of the cooling tip (2000) may be implemented in various shapes such as polygons.

Figure 9:
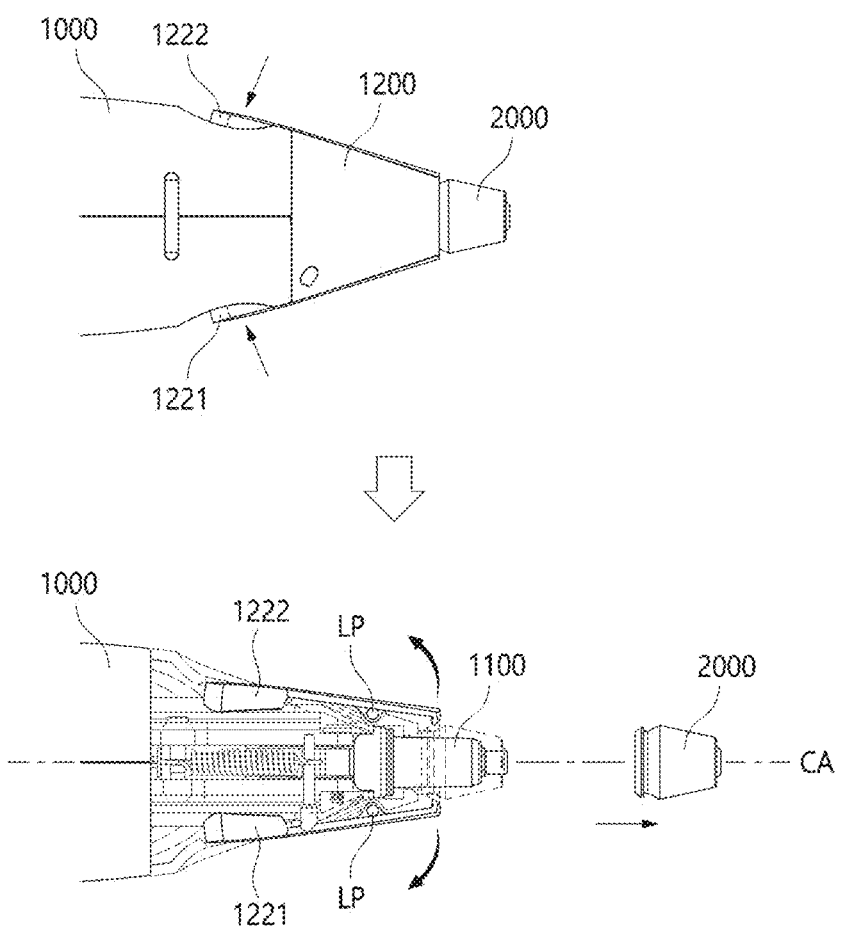
FIG. 9 shows a cooling tip being detached from a cooling device according to an exemplary embodiment of the present disclosure.

FIG. 9 shows a cooling tip (2000) being detached from a cooling device (1000) according to an exemplary embodiment of the present disclosure Referring to FIG. 9, the cooling tip (2000) may be detached from the cooling device (1000) according to the operation of the coupling member (1220) while the cooling tip (2000) is mounted on the cooling device (1000).

Hereinafter, for convenience of description, a case where the coupling member (1220) includes a latch part and the cooling tip (2000) includes a groove corresponding to the latch part is described, but the technical idea of the present disclosure is not limited thereto.

Referring back to FIG. 9, the cooling tip (2000) may be mounted on the cooling device (1000) by the coupling member (1220). Specifically, the latch parts of the first coupling member (1221) and the second coupling member (1222) which are arranged symmetrically with respect to the central axis (CA) are engaged with the grooves of the cooling tip (2000), thereby mounting the cooling tip (2000) on the cooling device (1000).

When pressure is applied to one end of the coupling member (1220), the cooling tip (2000) may be detached from the cooling device (1000). For example, referring to FIG. 9 again, when one end of the first coupling member (1221) and one end of the second coupling member (1222) are pressed by the user respectively, the first coupling member (1221) and the second coupling member (1222) rotate with respect to the coupling member fixing pin (LP), and thus each latch parts of the first and second coupling members are detached from the grooves of the cooling tip (2000) and the cooling tip (2000) may be detached from the cooling device (1000). In this example, in order to detach the cooling tip (2000) from the cooling device (1000), an elastic force via the elastic member (1300), as described later, may be applied in the direction of the central axis (CA).

As such, the cooling tip (2000) is easily detached from the cooling device (1000) in a simple manner, the user may immediately stop cooling in an emergent situation. At this time, the cooling tip remains attached to the target by ice adhesion, and the cooling tip (2000) may be light in weight. It may be specifically 2 g or less, or more specifically less than 1 g so as not to exert excessive force on the target by gravity.

Figure 10:
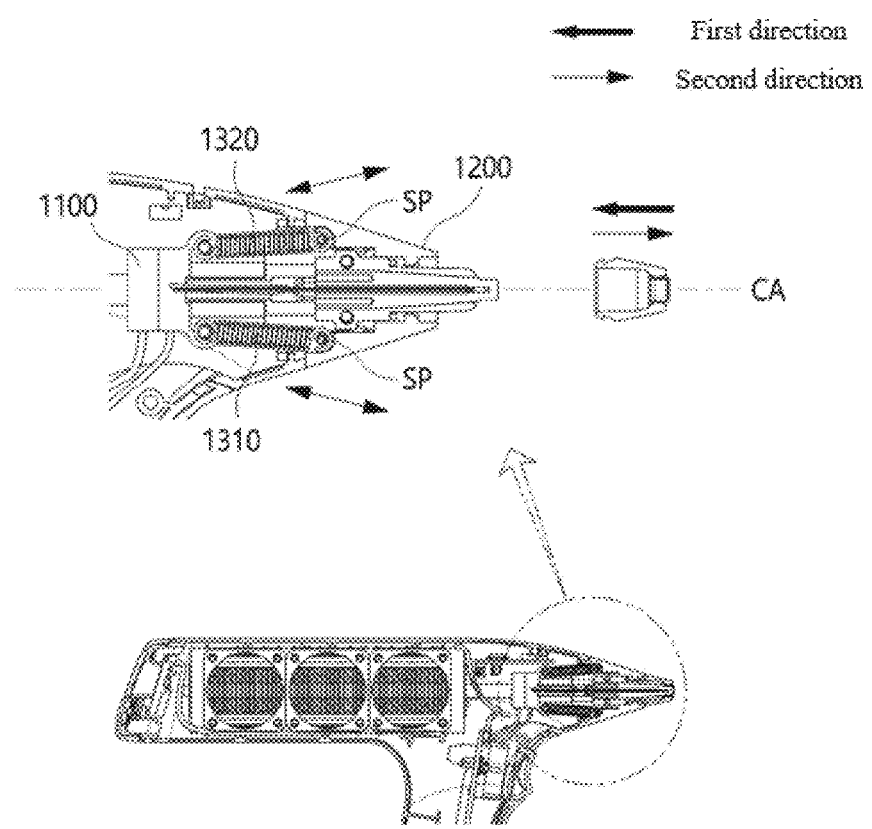
FIG. 10 shows an elastic member moving when a cooling tip is mounted on or detached from a cooling tip according to an exemplary embodiment of the present disclosure.

FIG. 10 shows movement of an elastic member (1300) when a cooling tip (2000) is mounted on or detached from a cooling device (1000) according to an exemplary embodiment of the present disclosure. The cooling tip (2000) may deform the elastic member (1300) while being mounted on the cooling device (1000), and the cooling tip (2000) may be detached from the cooling device (1000) by the restoring force or elastic force of the deformed elastic member (1300).

Hereinafter, the majority of the description features a case in which the elastic member (1300) comprises a tension spring and is mounted symmetrically with respect to the central axis (CA), but the technical idea of the present invention is not limited thereto, and a case in which one or more objects using restoring force such as compression springs and torsion spring are mounted may be applied in a similar manner.

The elastic member (1300) may be stretched or contracted as the cooling tip (2000) is mounted on or detached from the cooling device (1000).

For example, referring to FIG. 10, when a cooling tip (2000) is mounted on a cooling device (1000) in the first direction along the central axis (CA), the first elastic member (1310) and a second elastic member (1320) may be stretched. Specifically, when one end of the first elastic member (1310) and a second elastic member (1320) are fixed to a coupling module (1200) with the elastic member fixing pin (SP) and the cooling tip (2000) being mounted on the cooling device (1000), the cooling module (1100) to which the other ends of the first elastic member (1310) and the second elastic member (1320) are fixed moves in the first direction, thereby stretching the first elastic member (1310) and the second elastic member (1320).

For another example, referring to FIGS. 9 and 10, when the coupling member (1220) is detached from the cooling tip (2000), the first elastic member (1310) and the second elastic member (1320) may contract. Specifically, in a state in which the first elastic member (1310) and the second elastic member (1320) are stretched, when the latch parts of the first coupling member (1221) and the second coupling member (1222) are detached from the grooves of the cooling tip (2000). the first elastic member (1310) and the second elastic member (1320) may contract, and thus as cooling module (1100) moves in the second direction, the cooling tip (2000) may be detached from the cooling device (1000).

In this case, the first direction means a proximal direction from the front end (F) of the cooling device (1000) to the user or the inside of the cooling device (1000), and the second direction may refer to a distal direction from the user or the inside of the cooling device (1000) to the front end (F).

The elastic member (1300) may provide an elastic force so that the cooling medium (1110) presses the contact member (2100) while the cooling tip (2000) is mounted on the cooling device (1000). For example, as the cooling tip (2000) is mounted on the cooling device (1000), the elastic member (1300) increases as described above to provide an elastic force in the second direction, and the pressure of the elastic force may be applied to the cooling medium (1110) in surface contact with the contact member (2100) of the cooling tip (2000) fixed by the coupling member (1220). At this time, as the cooling medium (1110) presses the contact member (2100), interfacial thermal resistance or Kapitza resistance decreases, thereby increasing the cooling energy transfer efficiency from the cooling medium (1110) to the contact member (2100). In this case, the elastic force provided by the elastic member (1300) may be set to 0.1 MPa or more, 0.2 MPa or more, or 0.5 MPa or more in consideration of cooling efficiency.

In order to reduce the interfacial thermal resistance between the cooling medium (1110) and the contact member (2100) described above, a portion of the contact member (2100), contacting the cooling medium (1110), may include a soft metal coating such as a tin coating of 1-10 μm.

Figure 11:
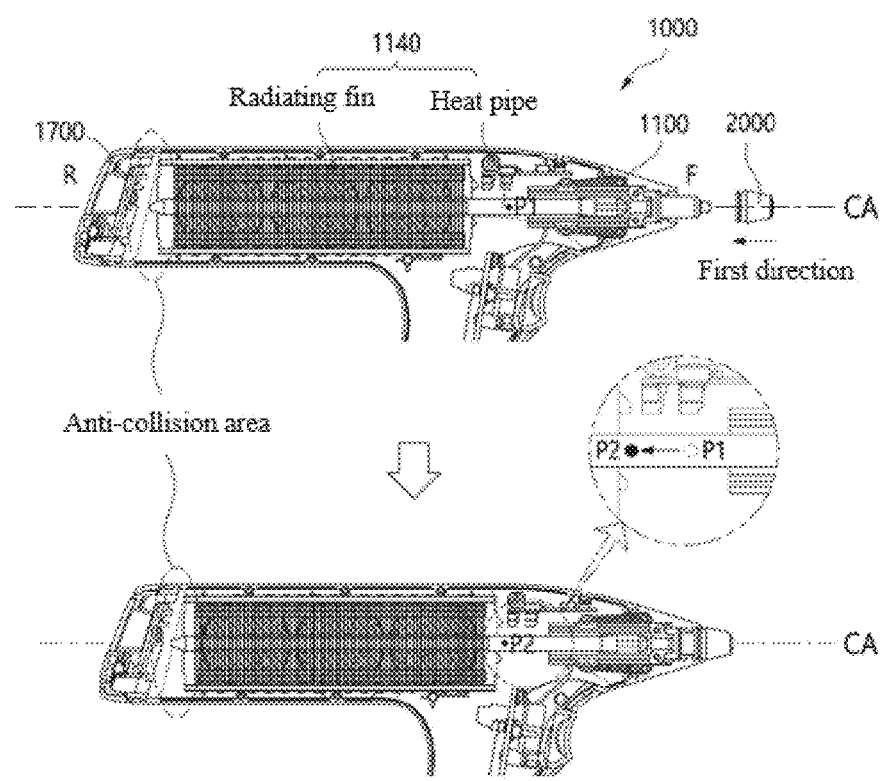
FIG. 11 shows a cooling module changing its position when a cooling tip is mounted on or detached from a cooling tip according to an exemplary embodiment of the present disclosure.

FIG. 11 shows a cooling module (1200) changing its position when a cooling tip (2000) is mounted on or detached from a cooling device (1000) according to an embodiment of the present disclosure The cooling module (1100) is movable within the cooling device (1000). For example, when the cooling tip (2000) is mounted on the cooling device (1000) in the first direction, the cooling module (1100) may also move in the first direction. Specifically, when the cooling tip (2000) is mounted on the cooling device (1000), the center, the center of gravity, or an arbitrary point of the cooling module (1100) may move from a first position (P1) on the central axis (CA) to a second position (P2) which is apart from the first position by a predetermined distance in the first distance. In this case, all the elements of the cooling module (1100), such as the heat dissipation member (1140) including the radiating fin and the heat pipe, may move, or only part of them may move. In addition, the distance between the first position (P1) and the second position (P2) may be determined based on the degree of stretch of the elastic member (1100) and the degree of protrusion of the cooling module (1100) from the cooling device (1000). For example, the distance between the first position (P1) and the second position (P2) may be determined within 1 to 5 mm.

In order for the cooling module (1100) to move as the cooling tip (2000) is mounted on or detached from the cooling device (1000), one end of the elastic member (1300), connected to the coupling module (1200), may be positioned closer to the front end (F) of the cooling device (1000) than the other end of the elastic member fixed to the cooling module (1100). In other words, when the cooling tip (2000) is mounted on the cooling device (1000) in the first direction, the other end of the elastic member (1300) fixed to the cooling module (1100) capable of moving in the cooling device (1000) may be positioned at a predetermined distance apart from one end of the elastic member (1300) fixed to the body of the cooling device (1000).

In addition, the cooling module (1100) may include a plurality of ribs so that the cooling module 1100 may move within the cooling device (1000). For example, those that contacts the temperature control member (1130) among the cooling medium (1100) of the distal part of the cooling module (1110), the cooling medium receiving member (1120), the temperature control member (1130), the tube and the heat dissipation member (1140) may be supported by the body part of the cooling device (1000) through the elastic member (1300), and the heat pipe and a radiating fin of the proximal part of the cooling module (1100) may be supported by a plurality of ribs installed in the body part of the cooling device (1000).

The cooling device (1000) may include an anti-collision area to prevent the cooling module (1100) from being damaged when the cooling module (1100) moves within the cooling device (1000).

In this case, the anti-collision area may refer to a region between the rear end (R) of the cooling device (1000) and the cooling module (1100) in a state in which the cooling tip (2000) is detached from the cooling device (1000). For example, referring to FIG. 11 again, the cooling device (1000) includes the output module (1700) at the rear end (R), and the anti-collision area may be a region between the output module (1700) and the cooling module (1100).

The anti-collision area may be interpreted as a space between the cooling module (1100) and the rear end (R) of the cooling device (1000). In addition, other components of the cooling device (1000) may not be disposed in the anti-collision area.

The anti-collision area may have a preset size. For example, when the cooling module (1100) moves from the first position (P1) to the second position (P2) as the cooling tip (2000) is mounted on the cooling device (1000), the length of the anti-collision area in the central axis direction (CA) may be greater than or equal to a distance between the first position (P1) and the second position (P2). More specifically, when the cooling module (1100) may be moved from the first position (P1) to the second position (P2), the cooling module (1100) may be disposed in the cooling device (1000) so that the heat pipe of the heat dissipation member (1140) is spaced apart from the output module (1700) of the rear end (R) of the cooling device (1000) by a distance between the first position (P1) and the second position (P2). At this time, when the cooling module (1100) moves about 3 mm, the length in the direction of the central axis (CA) of the anti-collision area may be greater than or equal to 3 mm.

The elastic member (1300) may provide elastic force in both directions. in order to protect the cooling module (1100) from external impact, For example, the elastic member (1300) may include a compressible tension spring or a tensionable compression spring. Specifically, when an impact is applied to the cooling device (1000) in the direction of the central axis (CA), the elastic member (1300) may be contracted or stretched to relieve the impact.

Hereinafter, the structure of an exemplary cooling tip (2000) is described with reference to FIGS. 12 and 13.

Figure 12:
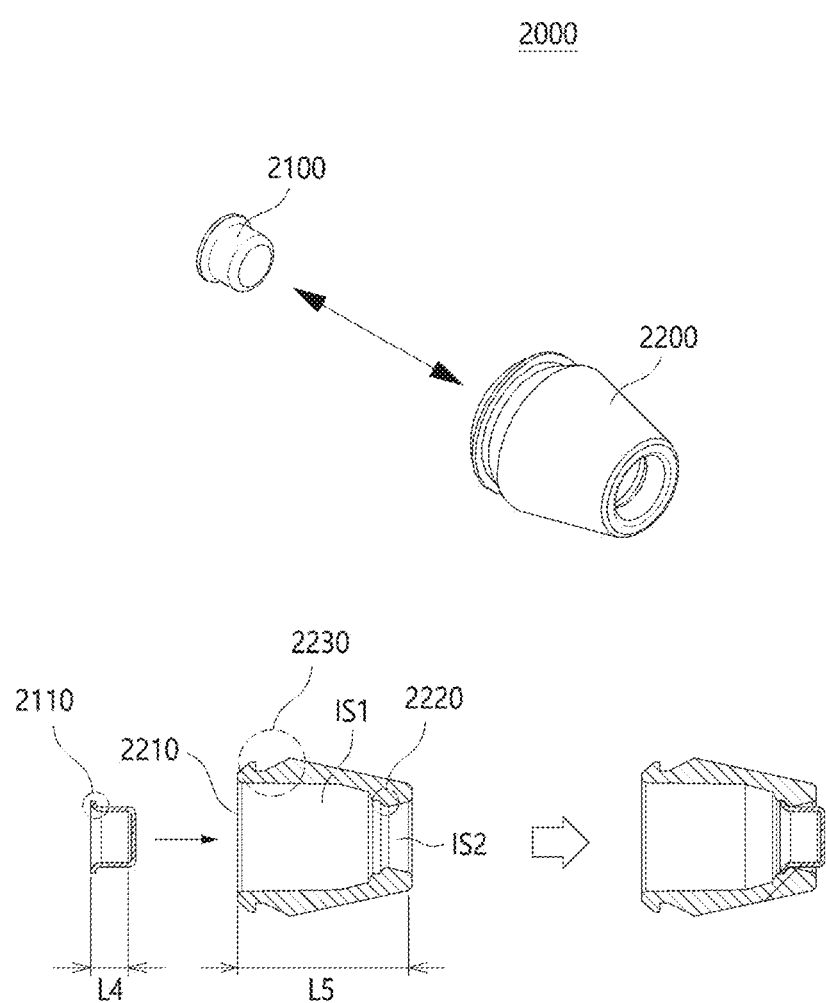
FIG. 12 shows a cooling tip and the internal configuration of the cooling tip according to an exemplary embodiment of the present disclosure.

FIG. 12 shows an internal structure of the cooling tip (2000) and the cooling tip (2000) according to an embodiment of the present disclosure.

Referring to FIG. 12, the cooling tip (2000) may include a contact member (2100) and a tip body (2200) on which the contact member (2100) is mounted.

The contact member (2100) may include an engaging portion (2110) to be mounted on the tip body (2200). For example, the contact member (2100) is inserted into the opening (2210) of the tip body (2200), and as the engaging portion (2110) of the contact member (2100) is in close contact with the engaging protrusion (2220) of the tip body (2200), which will be described later, the contact member (2100) and the tip body (2200) may be fixed to each other by force. At this time, the cooling medium (1110) presses the contact member (2100) by the elastic force of the elastic member (1300) so that the engaging portion (2110) of the contact member (2100) may tightly contact the engaging protrusion (2220) of the tip body (2200).

The engaging portion (2110) of the contact member (2100) may be implemented in a shape to be mounted on the tip body (2200). For example, the engaging portion (2110)

of the contact member (2100) may have a tapered shape that becomes narrower in the direction in which the contact member (2100) is inserted into the tip body (2200).

The tip body (2200) may include a groove (2230) for mounting on the cooling device (1000) and an engaging protrusion (2220) for mounting the contact member (2100). For example, referring to FIG. 12 again, the groove (2230) for engaging the coupling member (1220) of the cooling device (1000) is formed outside the tip body (2200), and the engaging protrusion (2220) to which the engaging portion (2110) of the contact member (2100) may be formed in the inside of the tip body (2200).

The description of the groove (2230) of the tip body (2200) used in the embodiment herein is described above.

The engaging protrusion (2220) may be formed at a position spaced apart from one end of the tip body (2200) by a preset distance. For example, the engaging projection (2220) may be formed to be spaced apart from one end of the tip body (2200) by a distance shorter than the fourth length (L4) of the contact member (2100) described above. In this case, the contact member (2100) may protrude from the tip body (2200) and be mounted and may contact a target surface prior to the tip body (2200) when cooling the target.

In the above, the description mainly features cases in which the contact member (2100) is coupled, fixed, or mounted on the tip body (2200) by force, but the technical idea of the present disclosure is not limited thereto, and the contact member (2100) and the tip body (2200) are coupled by other mechanical methods such as adhesive coupling or bonding, magnetic coupling or bonding, and pin coupling or bonding.

At least a portion of the cooling module (1100) and the contact member (2100) may be inserted into the tip body (2200). For example, referring to FIG. 12 again, the tip body (2200) may include the initial internal space (IS1) into which at least a part of the cooling medium receiving member (1120) is inserted, and a second internal space (IS2) to which at least portion of the contact member (2100) is inserted.

In this example, the first internal space (IS1) may be implemented in a shape corresponding to the shape of the cooling medium receiving member (1120). For example, when the cooling medium receiving member (1120) has a cylindrical shape that has a third length (L3) and a fourth width (W3), the first internal space (IS1) may be implemented in shape that has a length shorter than the third length (L3) and a width corresponding to the fourth width (W4).

In this example, the second internal space (IS2) may be implemented in a shape corresponding to the shape of the contact member (1120). For example, the second inner space (IS2) may be implemented in a shape whose width gradually increases in the direction in which the contact member (2100) protrudes from the engaging protrusion (2220). In this case, cooling efficiency may be increased because a side surface of the contact member (2100) does not contact other portions of the tip body (2200) except for the engaging projection (2220). In addition, an indentation mark formed on the target surface by the cooling tip (2000) may have a clear shape such as concentric circle.

The first internal space (IS1) and the second internal space (IS2) may be divided based on the engaging protrusion (2220), but the technical concept of the present invention is not limited thereto.

Figure 13:
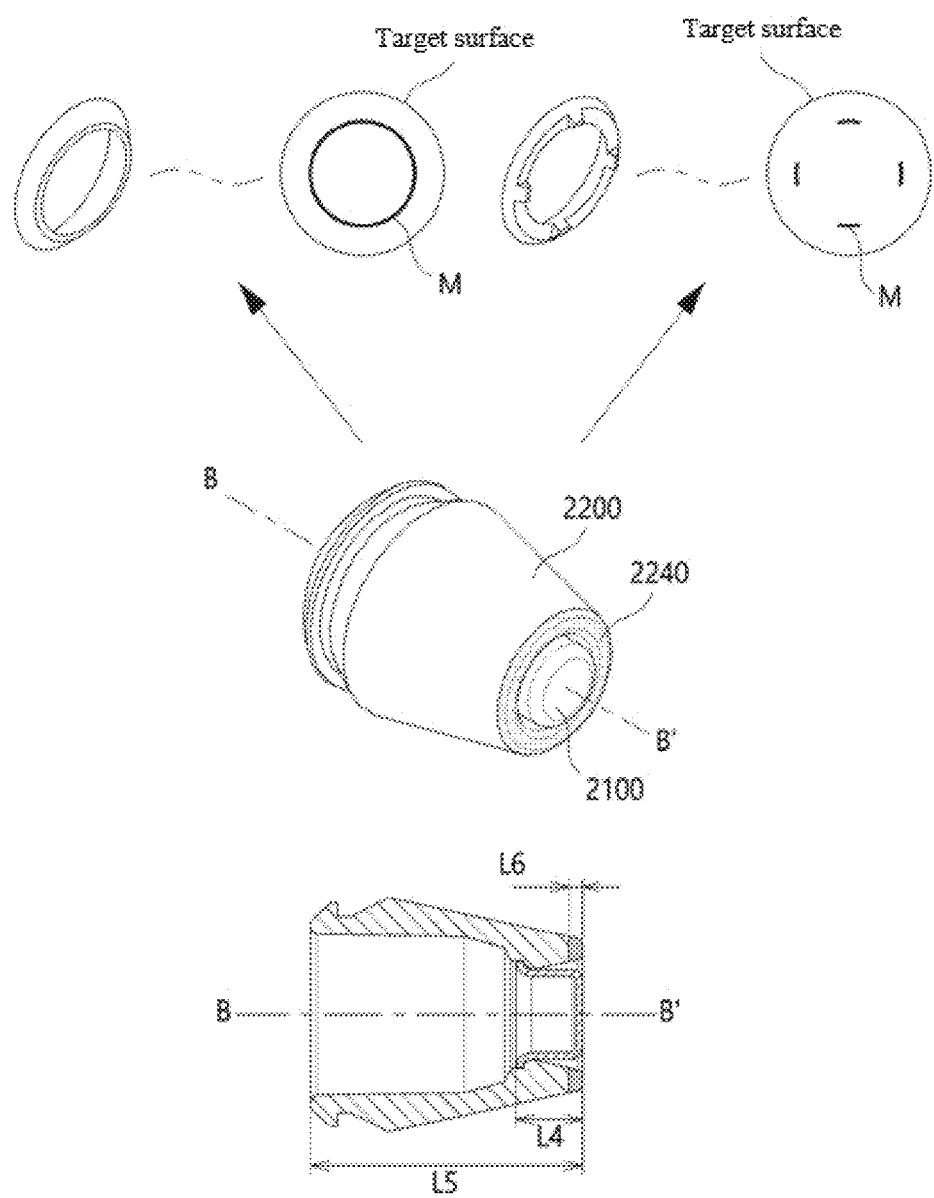
FIG. 13 shows an exemplary formation of a cooling tip in order to form a pressed mark on the surface of a target.

FIG. 13 shows a shape of the cooling tip (2000) for marking an indentation mark (M) on a target surface according to an embodiment of the present disclosure.

Referring to FIG. 13, at least a portion of the cooling tip (2000) may be implemented in a shape for forming a mark (M) on a surface of the target. In this case, the mark (M) is displayed on the target surface by pressure as the cooling tip (2000) physically contacts the target surface and may indicate the contact position of the cooling tip (2000) with respect to the target surface.

At least a portion of the tip body (2200) may have a protruding shape. For example, a tip body end (2240) may partially protrude to form a mark (M) on the target surface. Specifically, the tip body end (2240) may protrude in a ring shape or a dot shape to make a ring-shaped or dot-shaped mark (M) using pressure on the surface of the target. The protruding shape of the tip body end (2240) may be implemented in various ways, such as a line shape or a dotted line shape, in addition to the ring shape or dot shape described above.

The tip body end (2240) may generally be configured as a part of the tip body (2200). However, the tip body end (2240) may be configured to be detachable from the tip body (2200). In addition, the tip body end (2240) may be implemented with the same component or material as that of the tip body (2200) or may be implemented with a different component or material.

The tip body end (2240) may have a specific length for forming the mark (M) on the target surface. For example, as shown in FIG. 13, the tip body end (2240) may extend according to the sixth length (L6).

In this example, the sixth length (L6) may be set in consideration of the length of the contact member (2100), protruding from the tip body (2200). For example, the sixth length (L6) may be set such that when the contact member (2100) is inserted into the tip body (2200), the degree of protrusion is greater than or equal to the tip body end (2240). In this case, when the cooling tip (2000) immediately contacts the target surface, the contact member (2100) contacts the target surface before or at the same time as the tip body end (2240), thereby forming the mark (M) on the target surface while maintaining cooling efficiency. For another example, the sixth length (L6) may be set such that the degree of protruding of the contact member (2100) from the tip body (2200) is smaller than the tip body end (2240).

The mark (M) is displayed on the target surface so that the cooling area may be distinguished after cooling of the target since the cooling tip (2000) has a specific shape. In this way, the area where the cooling is performed on the target or the target surface is distinguished and thus a portion to be performed in next treatment may be clarified.

In the process of cooling the target using the cooling system (10), there may be cases in which the treatment is performed while the target is unstable due to the specific characteristics of the target or the user's carelessness, or in which the target is damaged. For example, when the cooling device (1000) performing main cooling for a specific time by triggering is driven before contacting a target surface through the cooling tip (2000) and sufficient cooling for the target is not achieved, treatment may be performed while the target is not anesthetized. For another example, if the cooling device (1000) is kept in contact with a target surface for an excessively long time, the target may be damaged by excessive cooling. For another example, when the cooling device (1000) does not contact a target with an appropriate pressure, sufficient cooling required for anesthesia may not be performed, and when too much pressure is applied to the target, the target may be damaged.

According to an embodiment of the present disclosure, a safer and more detailed cooling control method may be provided in order to prevent the described problem above. For example, a cooling control method may be provided including a step that involves determining whether or not cooling performance conditions necessary for cooling a target, such as whether or not the cooling device (1000) has made appropriate thermal or physical contact with a target surface through the cooling tip (2000), is satisfied. For this cooling control method, the time elapsed from the time when the thermal or physical contact between cooling tip (2000) and the target surface occurs may be measured, and through this, the cooling performance time for a target is limited to a specific time, and as a result, the target is not excessively cooled.

Hereinafter, a safe and detailed cooling control method using the cooling system (10) will be described with reference to FIG. 14 to FIG. 17.

Figure 14:
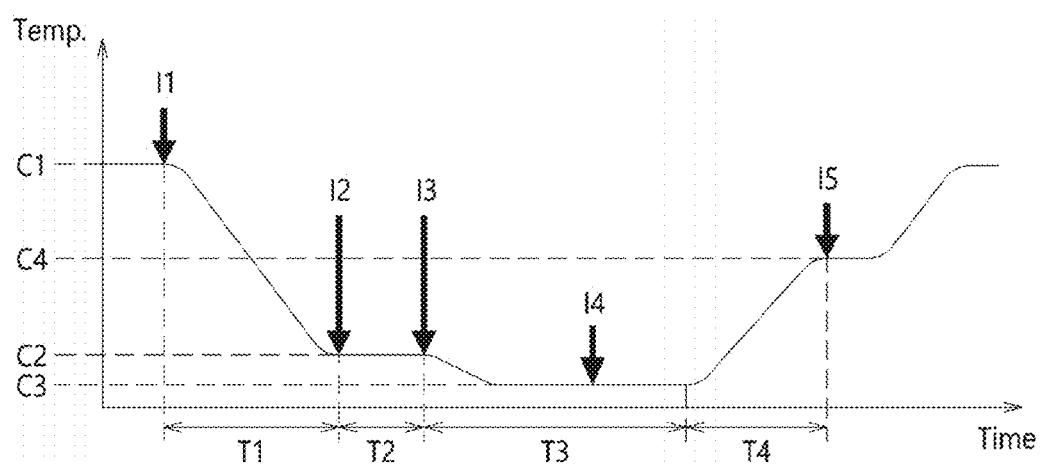
FIGS. 14 and 15 show exemplary temperatures detected by a sensor module as time elapses in the event that a target is cooled using a cooling control method according to an exemplary embodiment of the present disclosure.

FIG. 14 shows the temperature that a sensor module (1400) detects as time elapses in cases where a target is cooled using a cooling control method according to an embodiment of the present invention.

As shown in FIG. 14, the temperature sensed over time by the sensor module (1400) is, may refer to, or corresponds to a temperature related to a target. For example, the temperature is, may refer to, or corresponds to a temperature of the cooling medium (1110) of the cooling module (1100) to cool a target to a specific temperature. For another example, the temperature is, may refer to, or corresponds to the temperature of the contact member (2100) of the cooling tip (2000). For another example, the temperature is, may refer to, or corresponds to the temperature at which the inside of a target or a surface of a target should be cooled. Hereinafter, for convenience of explanation, the descriptions mainly feature cases where the temperature measured by the sensor module (1400) over time is the temperature of the cooling medium (1110), but the technical idea of the present invention is not limited thereto, and it may be similarly applied when the temperature measured by the sensor module (1400) is the temperature of the contact member (2100), the temperature inside a target, or the temperature of a target surface.

Referring to FIG. 14, the cooling system (10) may control the temperature of the cooling medium (1110) during the initial to fourth time periods (T1, T2, T3, T4). Each section will be described in detail below.

In the first time period (T1), the cooling system (10) may be prepared for cooling at the beginning. For example, the cooling device (1000) may control the temperature control member (1130) so that the cooling medium (1110) of the initial temperature (C1) reaches a second temperature (C2).

In this example, the first temperature (C1) may refer to the temperature of the cooling medium (1110) before the cooling system (10) operates. At this time, the length of the first time period (T1) may be determined according to the first temperature (C1). For example, the first temperature (C1) may be the same as the room temperature, and in this case, power may not be supplied to the temperature control member (1130). In another example, the first temperature (C1) is lower than the room temperature, and the cooling system (10) controls the temperature control member (1130) to adjust the temperature of the cooling medium (1110) before the first time period (T1) to temperature (C1). In this case, if the first temperature (C1) is lower than room temperature, the length of the first time period (T1) may be shortened. On the other hand, the first temperature (C1) may be maintained higher than the dew point, thereby preventing moisture from condensing on the cooling medium (1110), and as a result, the length of the first time period (T1) is shortened and the user convenience may be increased. Specifically, if the temperature of the room temperature is 25° C., when the first temperature (C1) is set to 20° C., the length of the first time period (T1) is shortened without moisture condensation on the cooling medium (1110), and the user's waiting time may be shortened.

In this case, a second temperature (C2) may refer to a standby temperature before the cooling system (10) performs cooling for the target. For example, the second temperature (C2) may be set at 0° C. to −20° C. The difference between the first temperature (C1) and the second temperature (C2) may be greater than the difference between the second temperature (C2) and a third temperature (C3) which is described below.

The cooling system (10) controls the temperature of the cooling medium (1110) to the second temperature (C2), which is a standby temperature, in the first time period (T1) so that time for the temperature of the cooling medium (1110) to be changed to a target temperature to be described below may be reduced according to the control of the cooling system (10). In such case, power consumption to lower the temperature to the target temperature in a given time would be reduced to save the power in a cooling device, which is beneficial for portable, wireless, and/or battery-operated handheld device. Also, when compared to the target temperature, it is possible to reduce the discomfort that a person receiving treatment may feel when a target surface is contacted for cooling.

In the second time period (T2), the cooling system (10) may determine whether cooling performance condition for a target is satisfied. For example, if the cooling performance condition for a target is satisfied while the cooling system (10) maintains the temperature of the cooling medium (1110) at the second temperature (C2), the cooling system (10) may cool the target during the third time period (T3) as described later.

The cooling performance condition may include a condition wherein the cooling device (1000) receives a trigger signal. For example, the cooling performance condition may include a condition wherein the cooling device (1000) receives a trigger signal from an input module (1600). More specifically, if the user operates a trigger disposed outside the cooling device (1000) and the control module (1800) of the cooling device (1000) receives the trigger signal, the control module (1800) may determine that the cooling performance condition is satisfied. In this case, the trigger signal may refer to a timer operation signal for instructing the operation of a timer by the user pressing a trigger button comprising a switch mounted on the cooling device 1000 or using a voice input. The timer may be used to set a cooling time to be described below and may be used to set a specific new time such as a standby time and a standby trigger time to be described below.

In addition, the cooling performance condition may include a condition wherein the cooling tip (2000) contacts a target surface. For example, the control module (1800) obtains temperature information indicating the temperature of the cooling medium (1110) from the sensor module (1400) and determines whether the cooling tip (2000) has contacted a target surface based on the obtained temperature information. If it is determined that the cooling tip (2000) has contacted the target surface, the control module (1800) may determine that the cooling performance condition is satisfied.

For another example, the control module (1800) may obtain or detect an electric signal related to the current or voltage of the cooling medium (1110) and determine whether a cooling performance condition is satisfied based on the obtained or detected electric signal. For another example, the control module (1800) may determine whether a cooling performance condition is satisfied by using a touch sensor or a pressure sensor disposed adjacent to the cooling module (1100). A method of determining whether the cooling tip (2000) or the cooling device (1000) equipped with the cooling tip (2000) in the cooling system (10) has contacted a target surface will be described in detail below.

The cooling performance condition may include a condition wherein the cooling medium (1110) of the cooling device (1000) and the target are thermally coupled to each other. For example, the control module (1800) obtains temperature information indicating the temperature of the cooling medium (1110) from the sensor module (1400) and determines whether the cooling tip (2000) has contacted a target surface based on the obtained temperature information. If it is determined that the cooling medium (1110) has contacted the target or target surface thermally, the control module (1800) may determine that the cooling performance condition is satisfied.

In some embodiments, the cooling performance condition comprises at least two or more of the described trigger signal reception condition, the contact condition of the cooling tip (2000) with the target surface, and the thermal coupling condition. For example, the cooling performance condition may include the contact condition of the cooling tip (2000) and the target surface, and the trigger signal reception condition. Specifically, if the contact condition is satisfied in the second time period (T2) and the trigger signal reception condition is satisfied within a preset time period, the cooling performance condition may be satisfied.

Figure 15:
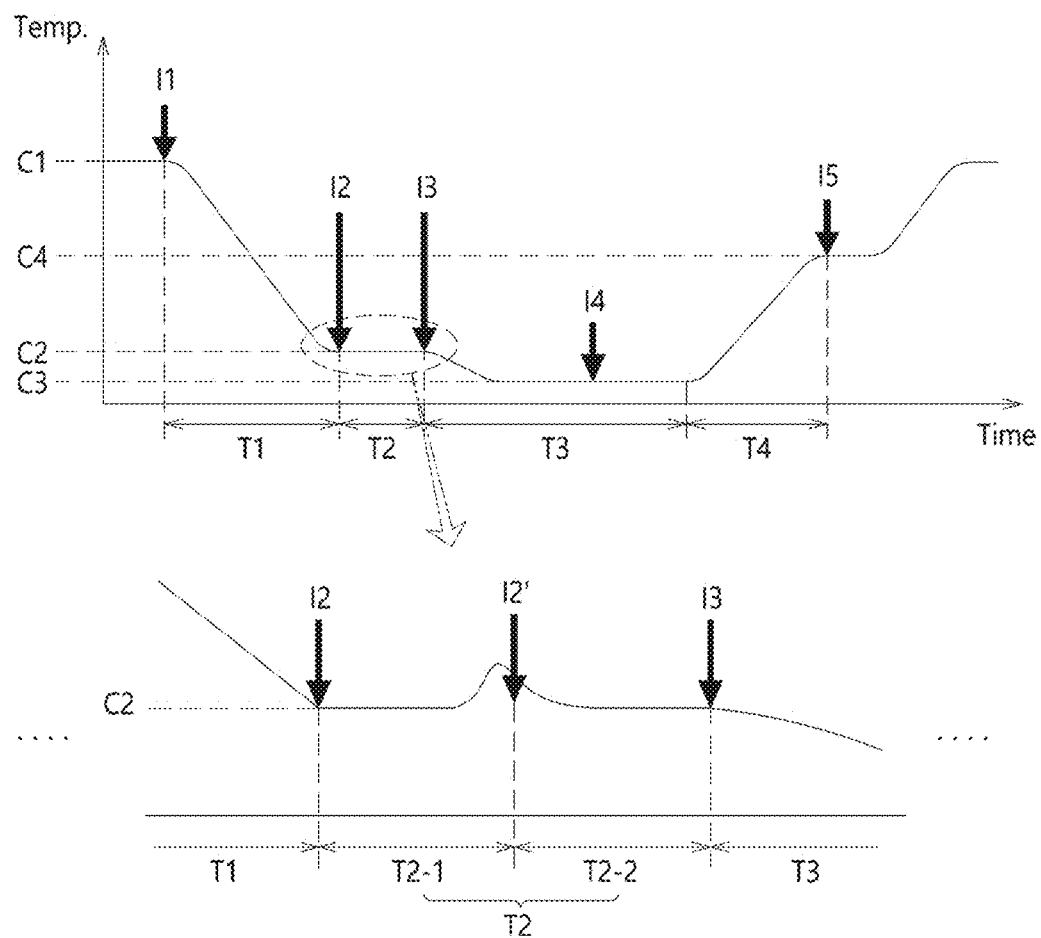

If the cooling performance condition is comprising a combination of different conditions, the second time period (T2) may be divided into a plurality of time periods. For example, as shown in FIG. 15, the second time period T2 may include a 2-1 time period (T2-1) and a 2-2 time period (T2-2). Specifically, the second time period T2 is divided into a 2-1 time period (T2-1) and a 2-2 time period (T2-2) wherein the 2-1 time period (T2-1) is from the point in time when the temperature of the cooling medium (1110) reaches the second temperature (C2) to the point in time when the contact condition between the cooling tip (2000) and the target surface is satisfied, and the 2-2 time period (T2-2) is from the point in time when the contact condition is satisfied to the point in time when a trigger signal reception condition is satisfied and all cooling performance conditions are satisfied.

The temperature of the cooling medium 1110 may slightly change in the 2-1 time period (T2-1) and the 2-2 time period (T2-2). For example, if the cooling performance condition includes a contact condition or a thermal bonding condition between the surface of a target and the cooling tip (2000), the temperature of the cooling medium (1110) may increase as shown in FIG. 15. The cooling device (1000) may determine whether a contact condition or a thermal coupling condition is satisfied through a temperature change of the cooling medium (1110). The process of determining the cooling performance condition by using the temperature change of the cooling medium (1110) is described in detail below.

In the 2-1 time period (T2-1) and the 2-2 time period (T2-2), the cooling system (10) may control a temperature control member (1130) so that the temperature of the cooling medium (1110) becomes the second temperature (C2).

When there is a plurality of cooling performance conditions, the cooling system (10) may provide a notification to the user based on the point in time when each cooling performance condition is satisfied. For example, as shown in FIG. 15, the control module (1800) may provide a second notification (I2') by using the output module (1700) when the cooling performance condition is satisfied in the 2-1 time period (T2-1). Specifically, when the control module (1800) detects that the cooling tip (2000) has contacted the surface of the target in the 2-1 time period (T2-1) as described later, the control module (1800) may provide to the user a visual or audible notification indicating that the cooling tip (2000) has contacted the surface of a target properly. The case in which the cooling performance condition is satisfied in the second time period (T2) may include both cases in which the cooling performance condition is satisfied in the 2-1 time period (T2-1) and the 2-2 (T2-2) time period respectively. In other words, if the cooling performance condition is not satisfied in the second time period (T2), this may include a case in which the cooling performance condition corresponding to the 2-1 time period (T2-1) is not satisfied, and a case in which the cooling performance condition corresponding to the 2-1 time period (T2-1) is satisfied, but the cooling performance condition corresponding to the 2-2 time period (T2-2) is not satisfied.

In some embodiments, the cooling system (10) may provide a notification to the user based on the point in time when each cooling performance condition is not satisfied or failed. For example, the control module (1800) can provide a third notification (I3') by using the output module (1700) when the cooling performance condition is not satisfied or failed in the 2-1 time period (T2-1) or when the device is reset or requires the user to restart the device or operation and/or process due to the failure of meeting the condition. Alternatively and/or additionally, the control module (1800) can provide a notification by using the output module (1700) when the cooling performance condition is not satisfied or failed in any of the 2-1 time period (T2-1) and the 2-2 (T2-2) time period or when the device is reset or requires the user to restart the device or operation and/or process due to the failure of meeting the condition.

If the described cooling performance condition is not satisfied in the second time period (T2), the cooling system (10) may stop cooling the target. For example, when the cooling operation condition is not satisfied within the standby time from the point in time when the temperature of the cooling medium (1110) reaches the second temperature (C2), the control module (1800) uses the temperature control member (1130) so that the temperature of the cooling medium (1110) increases. In some embodiments, the temperature of the cooling medium (1110) increases upon the failure of satisfying the cooling operation condition is at least 5° C., at least 6° C., at least 7° C., at least 8° C., at least 9° C., at least 10° C. higher than C2. In some embodiments, the temperature of the cooling medium (1110) increases upon the failure of satisfying the cooling operation condition is at or above −10° C., at or above −9° C., at or above −8° C., at or above −7° C., at or above −6° C., at or above −5° C., at or above −4° C., at or above −3° C., at or above −2° C., at or above −1° C., at or above −0° C. Alternatively and/or additionally, the temperature of the cooling medium (1110) increases upon the failure of satisfying the cooling operation condition is sufficient or effective to prevent an ice adhesion on the target surface. For another example, when the cooling performance condition is not satisfied in the second time period (T2), the control module (1800) may turn off the power.

In another example, when the cooling performance condition is not satisfied in the second time period (T2), the control module (1800) may not reduce the temperature of the cooling medium (1110).

In some embodiments case, the standby time may be set within a preset safety time range to prevent damage to a target in advance. For example, the standby time may be set within 60 seconds. In other embodiments, the standby time may be set to 5 seconds, 10 seconds, 20 seconds, 30 seconds, 45 seconds or 60 seconds. This may be done to mitigate risk of damage to a target in a state where the user contacts the cooling tip (2000) with a target surface, the cooling performance condition such as trigger signal reception is not satisfied, and the contact between the cooling tip (2000) and the target surface continues.

On the other hand, with a plurality of cooling conditions, the cooling system (10) may stop cooling the target if one or more cooling performance conditions are not satisfied in either the 2-1 time section (T2-1), the 2-2 time period (T2-2) or some other predetermined amount of time. For example, when the contact condition between the cooling tip (2000) and the target surface is not satisfied within the standby time from the point in time when the temperature of the cooling medium (1110) reaches the second temperature (C2), the control module (1800) uses the temperature control member (1130) so that the temperature of the cooling medium (1110) increases or turns off the power. In another example, when the trigger signal reception condition is not satisfied within the standby trigger time from the point in time when the contact condition between the cooling tip (2000) and the target surface is satisfied, the control module (1800) uses the temperature control member (1130) so that the temperature of the cooling medium (1110) increases or turns off the power.

In this case, the standby contact time may be set to an appropriate time for the user to contact the cooling tip (2000) with the surface of a target or thermally bond them. For example, the standby contact time may be set within 60 seconds. More preferably, the standby contact time may be set to 1 second, 2 seconds, 3 seconds, 4 seconds, 5 seconds, 7 seconds, 10 seconds, 15 seconds, 20 seconds, 25 seconds, 30 seconds or 45 seconds. Even when it is determined that the contact condition is not satisfied due to a failure or malfunction of the cooling system (10) despite the cooling tip (2000) having contacted the surface of the target, the target may be prevented from being excessively cooled, as described above, by setting the standby contact time to be short.

In addition, the standby trigger time may be set in an excessive cooling prevention time range to prevent the cooling tip (2000) from contacting the surface of the target for too long or being thermally coupled thereto. For example, the standby trigger time may be set within 30 seconds. More specifically, the standby trigger time may be set to 1 second, 2 seconds, 3 seconds, 4 seconds, 5 seconds, 10 seconds, or 15 seconds. The standby trigger time may be set shorter than the standby contact time. By setting the standby trigger time sufficiently short as described above, the actual time for the target to be cooled by the cooling tip (2000) may be limited, and thus, the target may be prevented from being excessively cooled by the cooling system (10).

The safety time range or the excessive cooling prevention time range is not limited to the description above and may be variously set. For example, the safety time range or the excessive cooling prevention time range may be set within a time after which reversible damage occurs in a target as cooling continues.

As described above, the cooling system (10) may more safely cool a target by determining whether the cooling performance condition is satisfied in the second time period T2, and the cooling performance condition is not limited to the described conditions.

In the third time period (T3), the cooling system (10) may perform main cooling for a target. For example, the cooling system (10) may change and maintain the temperature of the cooling medium (1110) to the third temperature (C3).

In this example, the third temperature (C3) may refer to a target temperature at which the target becomes anesthetized or painless as cooling is performed on the target. For example, the third temperature (C3) may be set from −60° C. to −5° C. In this case, the third temperature (C3) may be set to be less than or equal to the second temperature (C2).

In the third time period (T3), the cooling system (10) may cool a target during the cooling time. In this case, the length of the cooling time may be set within a range in which the cooling anesthesia effect on the target occurs. For example, the length of the cooling time may be set between 5 and 20 seconds. For another example, when the cooling system (10) performs cooling for other purposes such as cooling treatment in addition to cooling anesthesia, the third time period (T3) may be set longer than 20 seconds.

In the third time period (T3), the cooling system (10) may provide a notification to the user. For example, as shown in FIG. 14, the control module (1800) may provide a third notification (I3) indicating that the third time period (T3) has started to the user through the output module (1700). In addition, the control module 1800 may provide a fourth notification (I4) indicating that the user is in the middle of the third time period (T3) through the output module (1700).

The cooling system (10) cools a target by controlling the temperature of the cooling medium (1110) to a target temperature during a cooling time in the third time period (T3), thus, the target may be in an anesthetic state or a painless state.

In the fourth time period (T4), the cooling system (10) may control the temperature of the cooling medium (1110) to detach the cooling device (1000) from the target surface. For example, when detaching the cooling device (1000) from a target surface, the cooling system (10) may change the temperature of the cooling medium (1110) to a fourth temperature (C4) in order to prevent at least a portion of the target from sticking to the cooling tip (2000) due to ice adhesion.

In this case, the fourth temperature (C4) may refer to a safe temperature at which the risk of an ice adhesion phenomenon between the cooling tip (2000) and the target does not occur, is prevented, or reduced. For example, the fourth temperature (C4) may be set between −10° C. and 10° C.

The cooling system (10) may change the temperature of the cooling medium (1110) to the fourth temperature (C4) in the fourth time period (T4) so that the cooling tip (2000) or the cooling device (1000) may be safely detached (e.g., without the ice adhesion phenomenon occurring, etc.) from a target surface after cooling the target. Alternatively and/or additionally, the cooling tip (2000) can be physically removed from the cooling tip by moving one or two latches coupled to the cooling tip (2000) where it urgently requires the detachment of the cooling tip (2000) or the cooling device (1000) from the target surface without occurring the ice adhesion. Alternatively and/or additionally, the cooling device (1000) can be turned off to increase the temperature of the cooling medium (1110) and/or the cooling tip (2000)

and to safely detach the cooling tip (2000) or the cooling device (1000) from the target surface without occurring the ice adhesion.

For example, the cooling system (10) may control the temperature control member (1130) so that the temperature of the cooling medium (1110) becomes the fourth temperature (C4) at a constant or variable speed during a preparation time for separation. At this time, the cooling system (10) may provide a fifth notification (I5) indicating that the temperature of the cooling medium (1110) has reached the fourth temperature (C4) or that the cooling tip (2000) may be safely separated from the surface of the target. In this case, the fifth notification (I5) may be provided even when the cooling system (10) stops cooling according to a specific condition in the cooling process for a target, or when the user manipulates the cooling device (1000) to stop cooling. Specifically, if an emergency occurs while a target is being cooled and the user stops cooling (or stops operation of the cooling device), the cooling system (10) may provide the fifth notification (I5) when the temperature of the cooling medium (1110) reaches the fourth temperature (C4). With the provision of the fifth notification (I5), the user may safely detach the cooling tip (2000) from the surface of the target.

The fourth time period (T4) may be distinguished from the third time period (T3). For example, the cooling device (1000) may drive a plurality of or different timers in the third time period (T3) and the fourth time period (T4) respectively. Specifically, the cooling device (1000) may control the temperature of the cooling medium (1110) to be maintained at a target temperature during the cooling time by driving a timer set to the cooling time in the third time period (T3) and control the temperature of the cooling medium (1110) to change to a safe temperature. In other words, the third time period (T3) may not include a control for changing the cooling device (1000) to a safe temperature by the cooling device (1000), thereby ensuring sufficient time for cooling the target.

In some embodiments, the cooling device (1000) is set to power off or turn off when the cooling tip (2000) is inadvertently displaced from the cooling device (1000) or improperly located relative to the cooling device (1000), or when the cooling tip (2000) is inadvertently or accidentally displaced or detached from the target surface.

So far, it is described that the first to fourth temperatures (C1, C2, C3, C4) indicate a specific temperature selected within a specific range for convenience of description, but the technical idea of the present invention is not limited thereto. For example, the first to fourth temperatures (C1, C2, C3, C4) may indicate within an error range (e.g., ±1° C., ±2° C., ±3° C., ±4° C., ±5° C.) based on a specific temperature selected within each temperature range described above. For another example, the first to fourth temperatures C1, C2, C3, and C4 may indicate a temperature range selected within the respective temperature ranges described above.

The described standby time, standby contact time, standby trigger time, cooling time, and separation preparation time may be set within an appropriate range to prevent damage to a target due to cooling of a target. For example, the cooling system (10) may provide cooling energy to a target during the standby time and the cooling time in the second time period (T2) and the third time period (T3), thus, the sum of the standby time and the cooling time may be set within a set time range. Specifically, the sum of the standby time and the cooling time may be set to be within 60 seconds, more preferably within 15 seconds to 30 seconds.

Similarly, if there is a plurality of cooling conditions, the cooling system (10) may provide cooling energy to a target during the 2-2 time period (T2-2) and the cooling time, thus, the sum of the standby trigger time and the cooling time may be set within a preset time range. Specifically, the sum of the standby trigger time and the cooling time may be set to be within 60 seconds, in some embodiments, within 15 seconds to 30 seconds. Furthermore, the sum of the standby contact time, the standby trigger time, and the cooling time may be set to be less than 60 seconds.

For another example, the sum of standby time which is the time it takes to cool a target, cooling time, and separation preparation time may be set to be less than 60 seconds.

For another example, when the cooling system (10) is used for the purpose of selectively destroying or treating a target in addition to cooling anesthesia, the sum of the standby time and the cooling time may be set to 60 seconds or more.

The cooling system (10) may provide a notification to inform the user of a start point, a progress point, or an end point of the first to fourth time periods (T1, T2, T3, T4). Alternatively, the cooling system (10) may provide a notification to inform the user of a start point, a progress point, or an end point of the 2-1 and 2-2 time periods (T2-1, T2-2). For example, referring to FIG. 14, the cooling device (1000) may provide the first to fifth notifications (I1, I2, I3, I4, I5) to the user using the output module (1700). For another example, as shown in FIG. 15, the cooling device (1000) may further provide a second notification (I2') in addition to the first to fifth notifications (I1, I2, I3, I4, I5) to the user. Notifications provided to the user during a cooling process will be described in detail later.

Figure 16:
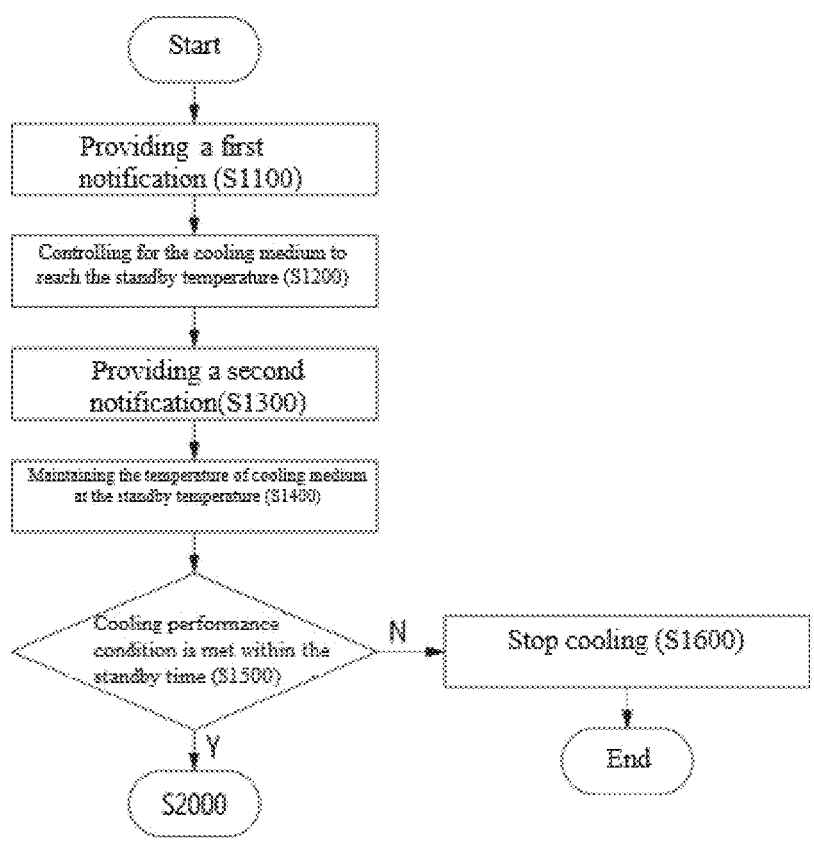
FIGS. 16, 17, and 18 show flowcharts of exemplary cooling control methods according to exemplary embodiments of the present disclosure.
Figure 17:
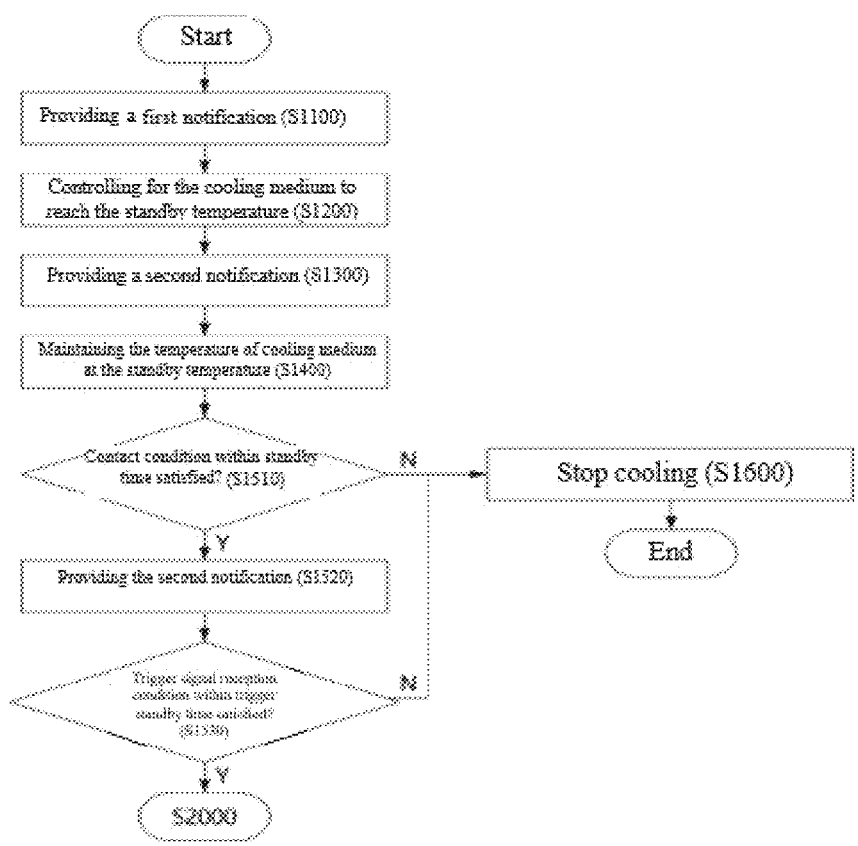

FIGS. 16 and 17 show a cooling control method according to an embodiment of the present disclosure.

Referring to FIGS. 16 and 17, the cooling control method includes the steps of: providing the initial notification (I1) (S1100); controlling the temperature of the cooling medium (1110) to be the standby temperature (S1200); providing the cooling second notification (I2)(S1300), maintaining the temperature of the cooling medium (1110) at the standby temperature during the standby time (S1400), determining whether the cooling performance condition within the standby time is satisfied (S1500); stopping cooling (S1600); and performing main cooling (S2000).

Each step is described in detail below. However, descriptions that overlap content described with reference to FIG. 14 above is omitted.

The cooling system (10) may provide the user with an initial notification (I1)(S1100). In this case, the initial notification (I1) may include a notification that indicates the start of preliminary cooling. For example, when the user drives the cooling device (1000), such as by turning on the power of the cooling device (1000) or pressing a cooling start button, the control module (1800) may output the notification (I1) through the output module (1700). The user may recognize through the first notification (I1) that the cooling module (1100) of the cooling device (1000) operates and the temperature control member (1130) is controlling the temperature of the cooling medium (1110) to be the standby temperature.

The cooling control method may further include a step that involves confirming whether or not the cooling tip (2000) is reused before, after, or when the first notification (I1) is provided to the user.

For example, the cooling system (10) may ask whether the user would like to reuse a cooling tip (2000) before providing the initial notification (I1) to the user. Specifically, the cooling system (10) asks the user whether or not the cooling tip (2000) mounted on the cooling device (1000) is reused through a visual or audible notification, and if it is determined that the cooling tip (2000) is not being reused based on the user's response, the cooling system (10) may perform the steps of providing the initial notification (I1) and the steps to be described later. In this case, the user's response may be made through a cooling start button input, a trigger button input, a voice input, etc. included in the cooling device (1000).

For another example, the cooling system (10) may determine whether it is reused by acquiring information on reuse from a storage or a capsule storing the cooling tip (2000). Specifically, the cooling device (1000) determines whether the cooling tip (2000) is a new product by recognizing a barcode printed or attached to a sealing member sealing the cooling tip (2000) or determines whether or not at least part of the cooling tip (2000) is damaged. When determining that the cooling tip (2000) is not being reused, the cooling device (1000) may provide an initial notification (I1) and perform the steps to be described later.

The cooling system (10) may control the temperature of the cooling medium (1110) to be the standby temperature (S1200). The description of how the temperature of the cooling medium (1110) is changed to the standby temperature matches the descriptions elsewhere in the specifications and thus will be omitted.

The cooling system (10) may provide a second notification (I2) to the user (S1300). In this case, the second notification (I2) may include a notification indicating that the temperature of the cooling medium (1110) has reached the standby temperature. For example, when the temperature information of the cooling medium (1110) obtained from the sensor module (1400) indicates the standby temperature, the control module (1800) may provide a second notification (I2) through the output module (1700). The user may recognize through the second notification (I2) that the cooling device (1000) is in a state to be able to make contact with a target surface and may bring the cooling device (1000) into contact with the target surface.

The cooling system 10 may maintain the temperature of the cooling medium (1110) at the standby temperature (S1400). For example, the control module (1800) may control the temperature control member (1130) to main the temperature of the cooling medium (1110) at the standby temperature for a preset standby time (e.g., 20 seconds) from the point in time when the temperature of the cooling medium (1110) reaches the standby temperature. In this case, as is described later, the control module (1800) may provide an additional notification to the user before the standby time elapses since when the standby time elapses without any action from the user, the cooling may be stopped or stopped.

The cooling system (10) may determine whether the cooling performance condition within the standby time is satisfied (S1500). The description of the cooling performance conditions and the method of the cooling system (10) to determine whether the cooling performance condition is satisfied matches the descriptions elsewhere in the present specifications and thus will be omitted.

The cooling system (10) may stop cooling when the cooling performance condition within the standby time is not satisfied (S1600). For example, the control module (1800) may stop cooling of the target if after the temperature of the cooling medium (1110) reaches the standby temperature, the cooling performance condition is not satisfied within the standby time. Specifically, the control module (1800) may increase the temperature of the cooling medium (1110) or turn off the power of the cooling device (1000) by controlling the temperature control member (1130). If the cooling performance condition is not satisfied within the standby time, the cooling system (10) may stop cooling the target, thereby preventing the target from being damaged.

The cooling system (10) may operate a timer for cooling a target according to the satisfaction of the cooling performance condition. For example, the control module (1800) operates a timer that is set to a specific time when receiving a trigger signal or when the cooling tip (2000) contacts the target surface, and the control module (1800) may stop cooling the target when the timer expires. In this case, the specific time set by the timer may be the cooling time described elsewhere in the specifications or may be set within the safe time range. As the cooling system (10) independently drives the timer according to the satisfaction of the cooling performance condition, damage to the target due to excessive cooling may be prevented.

In this case, when there are a plurality of cooling conditions, one of the cooling conditions may have priority over the other cooling conditions, and the cooling system (10) may operate at least one timer.

For example, if the cooling performance condition includes a trigger signal reception condition and a contact condition between the cooling tip (2000) and the target surface, the contact condition may have priority over the trigger signal reception condition.

For example, only when the contact condition is satisfied and next, the trigger signal reception condition is satisfied within a preset time or standby trigger time, the cooling performance condition may be satisfied. Specifically, when the cooling tip (2000) contacts the target surface within the standby time while the temperature of the cooling medium (1110) reaches the standby temperature, the timer is operated for a preset time (for example, the standby trigger time), and when the control module (1800) receives the trigger signal before the timer ends, the temperature of the cooling medium (1110) is changed to a target temperature and is maintained. If the control module (1800) does not receive the trigger signal before the timer ends, cooling of the target may be stopped.

For another example, if the trigger signal reception condition is satisfied after the contact condition is satisfied and the standby trigger time elapses in order, the control module (1800) may operate a timer when the contact condition is satisfied, and may not newly operate a timer or an additional timer even if a trigger signal reception condition is satisfied. Alternatively, in cases where the contact condition is satisfied after the trigger signal reception condition is satisfied, the control module (1800) operates the timer when the trigger signal reception condition is satisfied and operates the timer again or an additional timer when the contact condition is satisfied. This means that the timer operation according to the contact condition is completed, cooling of the target may be stopped.

For another example, the trigger signal reception condition may partially take priority over the contact condition in the case above. Specifically, in cases where the trigger signal reception condition is satisfied after the contact condition is satisfied, the control module (1800) may operate the timer when the contact condition is satisfied and operate the timer again or an additional timer when the trigger signal reception condition is satisfied. Alternatively, the control module (1800) may stop cooling the target when the contact condition within the standby time is satisfied but the trigger signal reception condition is not satisfied.

When there is a plurality of cooling conditions, the cooling control method may further include a step of determining whether the cooling condition is satisfied or not, and a step of providing additional notification. For example, referring to FIG. 17, the cooling control method may further include the steps of: instead of determining whether the contact condition within the standby contact time is satisfied (S1510), instead of determining whether the cooling performance condition within the standby time described above is satisfied (S1500); providing the second notification (12'); and determining whether the trigger signal reception condition is satisfied within the standby trigger time (S1530). The description mainly features a case in which there is a plurality of cooling conditions and a case in which the trigger signal reception condition is satisfied after the cooling tip (2000) has contacted the target surface for convenience, but the technical idea of the present invention is not limited thereto.

Figure 18:
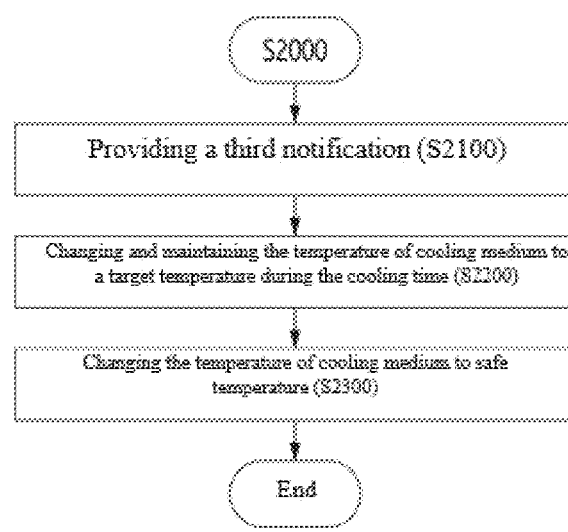

The cooling system (10) may determine whether the contact condition is satisfied within the standby contact time (S1510); provide a second notification 12' (S1520) when the contact condition is satisfied; determine whether the trigger signal reception condition is satisfied within the standby trigger time (S1530); and perform the main cooling of the target when the trigger signal reception condition is satisfied. In this case, if the contact condition is not satisfied within the standby contact time or the trigger signal reception condition is not satisfied within the standby trigger time, the cooling system (10) may stop cooling (S1600). The detailed description of a cooling control method for when there are a plurality of cooling conditions is omitted as it has been described elsewhere in the specifications. The cooling system (10) may perform main cooling for a target when the cooling performance condition is satisfied (S2000). Referring back to FIG. 18, the step that involves performing the main cooling of a target by the cooling system (10) (S2000) may include the steps of: providing the third notification (13) (S2100); changing and maintaining the temperature of the cooling medium (1110) to a target temperature during the cooling time (S2200); and changing the temperature of the cooling medium (1110) to a safe temperature (S2300).

In some embodiments, the cooling system provides additional safety measures or features that prevents inadvertent damage of the target surface due to the failure of proper operation of the cooling device (1000). For example, the cooling device (1000) can be manually turned off if a cooling procedure must be terminated at or during any stage of cooling operation. In some embodiments, the cooling device (1000) can be manually turned off by pressing a button or a switch on the cooling device (1000) (e.g., an on/off button, an emergency button separate from the on/off button, etc.). In some embodiments, the operation of the cooling device (1000) can be interrupted by ejecting or separating the cooling tip (2000) from the cooling medium (1110) (e.g., by pressing the latches on the cooling device (1000), etc.) such that the temperature ejected or separated cooling tip (2000) is increased to prevent further cooling of the target surface. In some embodiments, such interruption of cooling operation can be use when the cooling procedure fails to terminate automatically or manually or the cooling device (1000) fails to turn off automatically or manually. In some embodiments, the cooling tip (2000) (separated or attached to the cooling device (1000)) can be remained on the target surface for a period sufficient to prevent ice adhesion (e.g., at least 3 seconds, at least 5 seconds, at least 10 seconds, at least 15 seconds, etc.).

Hereinafter, each step that involves the main cooling performing step (S2000) is described in detail.

The cooling system (10) may provide a third notification (I3) to the user. In this case, the third notification (I3) may include a notification indicating that the cooling performance condition is satisfied within the standby time or the standby trigger time thereby performing main cooling. For example, the control module (1800) may output a third notification (I3) through the output module (1700) when receiving a trigger signal within the waiting time or the trigger waiting time after the temperature of the cooling medium (1110) reaches the standby temperature, or determining that the cooling tip (2000) has contacted the target surface based on the temperature information or the electrical signal acquired from the sensor module (1400). Through the third notification (I3), the user may recognize that main cooling for the target has started or that the cooling tip (2000) has contacted the target surface.

The cooling system (10) may change and maintain the temperature of the cooling medium (1110) to a target temperature during the cooling time (S2200). For example, the control module (1800) may change and maintain the temperature of the cooling medium (1110) to a target temperature for cooling time from the point in time when the cooling performance condition is satisfied. In this case, the control module (1800) may provide a fourth notification (I4) indicating that the target is being cooled to the user according to the time during which the main cooling is performed. Specifically, the control module (1800) may provide a notification to the user when the cooling time has lapsed in half or when the cooling time has elapsed. Alternatively, the control module (1800) may provide a notification to the user every predetermined time (e.g., 2 seconds, 3 seconds, 4 seconds, 5 seconds, etc.).

The cooling system (10) may change the temperature of the cooling medium (1110) to a safe temperature (S2300). For example, the control module (1800) may control the temperature control member (1130) so that the temperature of the cooling medium (1110) becomes a safe temperature. At this time, when the temperature of the cooling medium (1110) reaches a safe temperature, the control module (1800) may provide a fifth notification (I5) to the user, indicating that the separation of the target and the cooling device (1000) is safe.

The cooling control method may include a step of pausing. For example, the cooling system (10) may stop the cooling control method if a pause condition is satisfied while at least one of the steps that the cooling control method described above is performed. Specifically, the cooling device (1000) may cut off power provided to the temperature control member (1130) or use the temperature of the cooling medium (1110) to increase the temperature of the cooling medium (1110) when the cooling device (1000) receives a control signal corresponding to a cooling start button or trigger button or receives a specific user voice signal while the cooling control method is being performed. In this case, when the temperature of the cooling medium (1110) reaches a safe temperature, the cooling device (1000) may provide a notification to the user indicating that the cooling tip (2000) may be safely detached from the target surface. Through this immediate pause function, the user may quickly separate or remove the cooling device (1000) equipped with the cooling tip (2000) or the cooling tip (2000) from the target surface, and the latch combination of the coupling module (1200) described above may be used.

The first to fifth notifications (I1, I2, I2', I3, I4, I5) may be given through various methods. For example, the first to fifth notifications (I1, I2, I2', I3, I4, I5) may include at least one among visual notifications such as flashing LEDs, audible notifications such as beep or voice output, and tactile notifications such as fine vibration. In addition, the first to fifth notifications (I1, I2, I2', I3, I4, I5) may be the same or may be implemented in different ways. In addition, the first to fifth notifications (I1, I2, I2', I3, I4, I5) may be temporary or may be continuous for at least part of a corresponding time period.

Hereinafter, a method of determining whether or not the cooling tip (2000) contacts the target surface is described with reference to FIG. 19.

Figure 19:
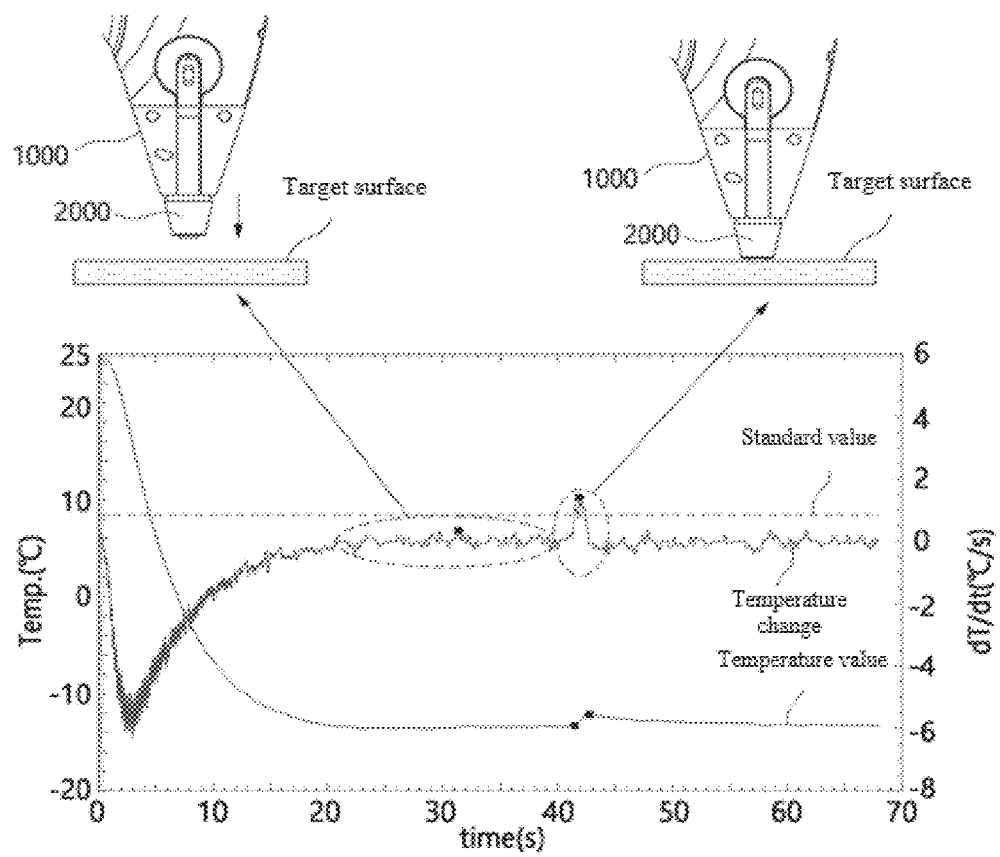
FIG. 19 shows a method of determining whether a target contacts a cooling tip according to an exemplary embodiment of the present disclosure.

FIG. 19 shows a method of determining whether a target surface contacts a cooling tip (2000) according to an embodiment of the present disclosure.

Referring to FIG. 19, the cooling system (10) may determine whether the cooling device (1000) equipped with the cooling tip (2000) has contacted the target surface based on sensing information obtained from the sensor module (1400).

For another example, whether a cooling tip (2000) and the target surface are in contact with each other may be determined based on a change of the temperature of the cooling medium (1110) over time.

For example, when the instantaneous change amount (=dT/dt) of the temperature of the cooling medium (1110) obtained from the sensor module (1400) is greater than or equal to a preset value, the control module (1800) may determine that the cooling tip (2000) has contacted the target surface. Referring to FIG. 19 again, when the cooling tip (2000) has not contacted the target surface, the instantaneous change in temperature of the cooling medium (1110) does not exceed the reference value, and when the cooling tip (2000) contacts the target surface, the temperature value of the cooling medium (1110) increases instantaneously, and the instantaneous change amount of the temperature of the cooling medium (1110) may exceed the reference value.

In this case, the control module (1800) may see an instantaneous change in the temperature of the cooling medium (1110) based on temperature information of the cooling medium (1110) obtained from the sensor module (1400) at different time points. For example, the following equation (1) may be used:

$$\text{grad}(i)=\{\text{data}(i+1)-\text{data}(i)\}/\{\text{time}(i+1)-\text{time}(t)\}$$

In this case, grad(i) may refer to the instantaneous change in temperature of the cooling medium (1110), and data(i) may refer to the temperature value of the cooling medium (1110) at an arbitrary first time point(time (i)), and data(i+1) may refer to a temperature value of the cooling medium (1110) at a second time point (time (i+1)) after the first time point. The control module (1800) may further use the following equation in obtaining an instantaneous change in temperature of the cooling medium (1110):

$$\text{data}(i)=(1-w)*\text{data}(i)+w*\text{data}(i-1)$$

Data(i−1) refers to the temperature value of the cooling medium (1110) at a third time point before the initial time point, and w is a weight and is selected between 0 and 1 to correct the temperature value of the cooling medium (1110).

For another example, a control module (1800) may determine that when a temperature change amount which is a difference in values of the temperature of a cooling medium (1110) at an arbitrary first time point and a second time point after the same is a preset value or greater, a cooling tip (2000) is in contact with the surface of the target.

For another example, a control module (1800) may determine that when the instantaneous change amount or the temperature change amount of the temperature of a cooling medium (1110) in an arbitrary time interval is a preset value or greater, a cooling tip (2000) is in contact with the surface of the target.

For another example, a control module (1800) may determine that when the temperature of a cooling medium (1110) exceeds a preset value, a cooling tip (2000) is in contact with the surface of the target.

For another example, a control module (1800) may determine that the base area of function to a time of a temperature change rate, which is an integral value of grad*time exceeds a preset value, the cooling tip (2000) is in contact with the surface of the target.

For another example, in order to precisely determine a contact, a control that has relatively high temperature precision may be used during a standby time or a standby trigger time as described later. For example, a PID control mentioned above may be used, specially, constant values Cp, Ci, Cd may be differently exhibited from those in the other interval, and more specifically, the Cd value may be set to be relatively great. For another example, a power that has a constant value may be applied to a temperature control member (1130) during a standby time or a standby trigger time. Specifically, the average value of power P(t) applied to a cooling medium (1110) through PID control during a predetermined time may be calculated, and the average value may be applied to a temperature control member (1130) during a standby time or a standby trigger time.

Whether a cooling tip (2000) is in contact with the surface of a target may be determined based on the temperature of each part of a cooling medium (1110). Specifically, as long as a cooling medium (1110) has a predetermined volume, temperatures of a part relatively close to a target surface and a part relatively far therefrom, in a cooling medium (1110), may differently change, and a cooling tip (2000) is in contact with the surface of a target may be determined by using a change in the temperature of each part.

For example, whether contact has been made may be determined based on the temperature of the portion of the cooling medium (1110) close to the cooling tip (2000) and the temperature of the portion of the cooling medium (1110) close to the temperature control member (1130). Specifically, when a difference in the initial temperature value obtained by a sensor disposed in the initial area close to a cooling tip in a cooling medium and a second temperature value obtained by a sensor disposed in a second area close to a temperature control member (1130) satisfies a preset range, in a case where a difference of the initial instantaneous change amount of the first temperature value and a second instantaneous change amount of the second temperature value satisfies a preset range or the base area value of a difference of the change rate of the first temperature value and the change rate of the second temperature value according to time satisfies a preset range, it is determined to be in contact with a cooling tip (2000) and a target surface, wherein the calculation process mentioned above may be used in deriving the temperature value of each part of the cooling medium (1110) or the instantaneous change amount of the temperature value.

As described above, in order to determine whether contact has been made with a cooling tip (2000) and a target surface by using the temperature of each part of a cooling medium (1110), a cooling device (1000) may be comprising a plurality of temperature sensors measuring temperature at each different part of the cooling medium (1110). For example, a cooling device (1000) may comprise the first temperature sensor disposed from one end of a cooling medium (1110) at a preset distance and a second temperature sensor disposed from the first temperature sensor at a preset distance along the central axis of the cooling medium (1110). For another example, a cooling device (1000) may be comprised a third temperature sensor disposed to be adjacent to a temperature control member (1130) and measuring the temperature of at least a part of a cooling medium (1110) and a fourth temperature sensor disposed to be farther from the temperature control member (1130) than the third temperature sensor and measuring the temperature of at least a part of the cooling medium (1110).

In some embodiments, a cooling device (1000) comprises two temperature sensors measuring a temperature change of one end of the cooling medium (1110) (e.g., temperature change due to the contact of the cooling tip (2000) to the target surface) and a temperature change of another end of the cooling medium (1110) (e.g., temperature change due to the feedback control for maintenance of cooling medium temperature). For example, the first temperature sensor is disposed at one end of a cooling medium (1110) that is proximal to the cooling tip (2000), and the second temperature sensor is disposed at another end of the cooling medium (1110) that is distal to the cooling tip (2000). In such embodiments, the first temperature sensor detects an instantaneous rate of temperature change of the cooling medium (1110) proximal the cooling tip (2000) resulting from the contact of the cooling tip (2000) to the target surface. When the temperature change occurs at one end of the cooling medium (1110), the control module (1800) may use feedback control to control the power applied to a temperature control member (1130) to maintain the temperature of the cooling medium (1110) as a preset temperature. The feedback mechanism results in the temperature change of the cooling medium (1110) distal to the cooling tip (2000), and the second temperature sensor detects such instantaneous rate of temperature change of the cooling medium (1110) distal to the cooling tip (2000). In some embodiments, the contact between the cooling tip (2000) and the target surface can be determined by one of the temperature change (e.g., instantaneous rate of temperature change) detected by the first or second sensors, or both of the temperature changes (e.g., instantaneous rate of temperature change) detected by the first and second sensors, respectively. In a detail, the contact between the cooling tip (2000) and the target surface can be determined when an instantaneous rate of temperature change detected by the first sensor is positive and the instantaneous rate of temperature change detected by the second sensor is negative.

As mentioned above, whether the cooling tip (2000) and a target surface are in contact with each other is determined based on the temperature of a cooling medium (1110), but the technical idea of the present invention is not limited thereto, and a determination regarding whether the target surface and the cooling tip (2000) are in contact may be made based on the temperature of the cooling tip (2000) or the temperature of the target surface.

For another example, whether a cooling tip (2000) and the surface of a target are in contact with each other may be determined based on a change in the electrical properties of a cooling medium (1110). Specifically, a control module (1800) or a sensor module (1400) may be comprising a circuit electrically connected with a cooling medium (1110), and the control module (1800) may acquire information such as the current, voltage or current value of the cooling medium (1110) from the cooling medium (1110) or the sensor module (1400) at an arbitrary time point and a time point before or after the same and determine that a cooling tip (2000) is in contact with the surface of a target when a change amount of the current, voltage, or current value of the cooling medium (1110) is a predetermined value or greater.

For another example, in order to determine whether a cooling tip (2000) and the surface of a target are in contact with each other, and the control module (1800) may determine, by using the touch sensor, whether the cooling tip (2000) and the surface of a target are in contact with each other. In this case, a capacitive touch sensor sensing capacitance changes, or a resistive touch sensor can be used.

For another example, whether a cooling tip (2000) and the surface of a target are in contact with each other may be determined based on a pressure applied to a cooling device (1000). Specifically, a sensor module (1400) may comprise a pressure sensor, and a control module (1800) may acquire pressure information instructing with a pressure value applied to a cooling module (1100) from the sensor module (1400) and determine that the cooling tip (2000) is in contact with the surface of a target when the pressure value exceeds a preset value. Furthermore, the cooling device (1000) may provide a safety notification or a danger notification to the user, respectively, when the pressure value obtained from the pressure sensor is in a safe range in which the target is not damaged or exceeds the pressure value causing damage to the target.

A cooling system (10) may provide a notification to the user when the cooling tip (2000) and the surface of a target are in contact with each other, and operate a timer set to a cooling time, or in a case where a trigger signal is received within a standby trigger time when a cooling tip (2000) and the surface of a target are in contact with each other, the cooling device (1000) may provide a notification to the user and operate the timer to a cooling time.

The description above mainly features cases in which the cooling tip (2000) contacts the target surface, but the technical idea of the invention is not limited thereto. For example, the above description may be similarly applied when the cooling medium (1110) contacts a target surface or the cooling medium (1110) is thermally coupled to a target surface.

In order to quickly and accurately determine whether a cooling tip (2000) and the surface of a target are in contact with each other, sensing information of a sensor module (1400) should be accurately and quickly acquired. Hereinafter, the arrangement position of the sensor module (1400) for obtaining sensing information quickly and accurately is described.

Figure 20:
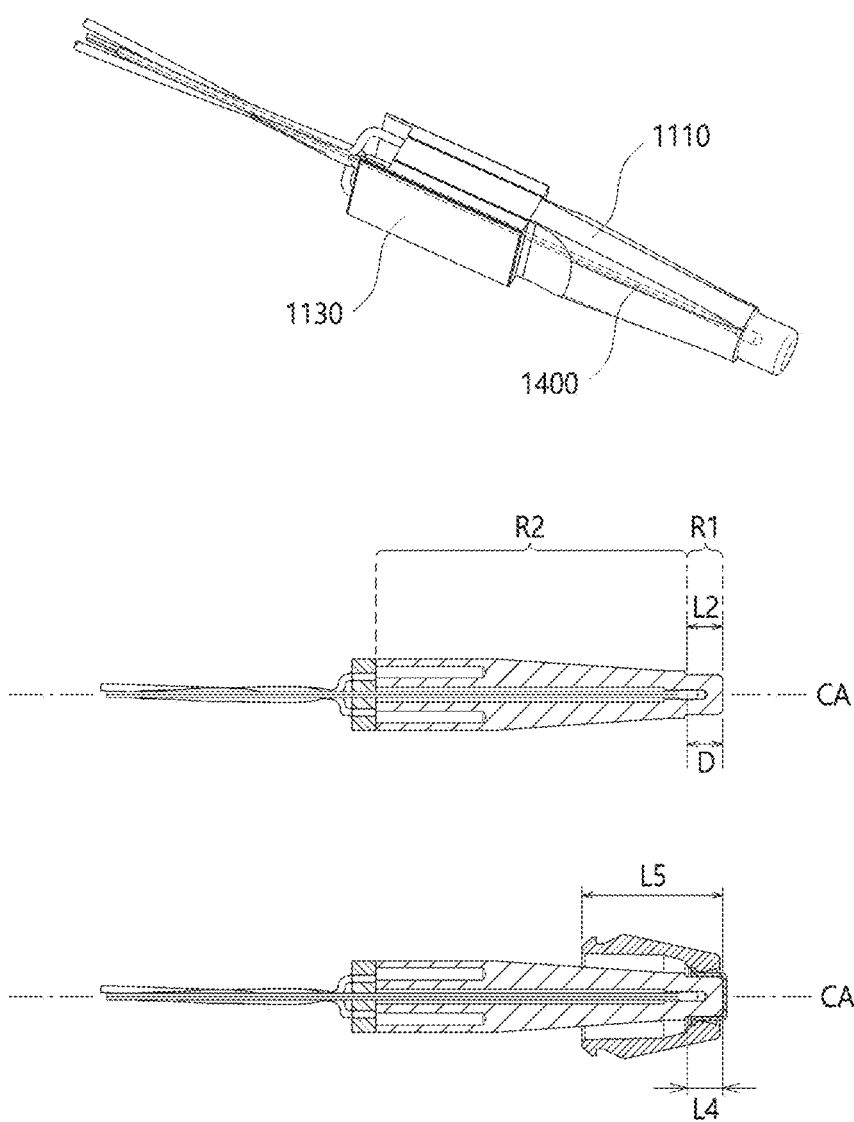
FIG. 20 shows a method of placing a sensor in a cooling device according to an exemplary embodiment of the present disclosure.

FIG. 20 shows a method for placing a sensor module (1400) in a cooling device (1000) according to an embodiment of the present disclosure. Hereinafter, the descriptions feature a case where a temperature sensor of which a sensor module (1400) is inserted into the cooling medium (1110), but the technical idea of the present invention is not limited thereto.

Referring to FIG. 20, a sensor module (1400) may be inserted into the inside of a cooling medium (1110) and provide a control module (1800) with temperature information acquired by sensing the temperature of the cooling medium (1110). For example, a sensor module (1400) may be disposed in a cooling medium (1110) so that a distance between a sensing part for sensing a temperature in the sensor module (1400) and one end of the cooling medium is a preset separation distance (D).

In this case, the sensing part may refer to at least a single part that is in contact or is not in contact with the cooling medium (1110) to acquire temperature information of the cooling medium (1110).

In addition, the separation distance (D) may refer to a distance from one end of the cooling medium (1110) to the center of a sensing part of the sensor module (1400) or one end of the sensing part.

The separation distance (D) may be set so that the sensing part of a sensor module (1400) is closes enough to the surface of a target. For example, referring to FIG. 20, a separation distance (D) may be set to be equal to or shorter than a second length (L2) of the protrusion part of a cooling medium (1110). For another example, a separation distance (D) may be set to be shorter than a fourth length (L4) of a contact member (2100) of the cooling tip (2000) or set to be equal to or longer than the fourth length (L4) and equal to or shorter than a fifth length (L5) of a tip body (2200) of the cooling tip (2000). More specifically, the separation distance (D) may be set within 10 mm. In this case, in order to minimize the distance between the center of a sensing part and the surface of a target, the thickness of a contact member (2100) in a separation distance (D) direction may be 1 mm or shorter.

A separation distance (D) may be set in consideration of the partial heat capacity of the cooling medium (1110). For example, referring to FIG. 20, when a cooling medium (1110) is divided to the initial part (R1) and a second part (R2) at the sensing part of a sensor module (1400), a separation distance (D) may be set so that the heat capacity of the initial part (R1) is less than the heat capacity of a second part. Specifically, the separation distance (D) may be set so that the mass of the first part (R1) is less than the mass of the second part (R2), or the specific heat of the first part (R1) is less than the specific heat of the second part (R2). In this case, it may be interpreted that a part close to the surface of a target is the initial part (R1) and a part far from the surface of a target is a second part (R2) in a cooling medium (1110) during surgery, based on the plane perpendicular to the central axis (CA) and includes the center of the sensing part, but the technical idea of the present disclosure is not limited thereto. The heat capacity of the contact member (2100) of the cooling tip (2000) may be set to be less than the heat capacity of the first part (R1), or the mass of the contact member (2100) of the cooling tip (2000) may be set to be less than 1 g, more specifically, less than 0.5 g.

As described above, as a separation distance (D) is set, the temperature of the cooling medium (1110), which is one of main elements for cooling a target in the cooling system (10), may be precisely controlled, and the contact of a cooling tip (2000) and the surface of the target may be accurately and quickly determined by quickly sensing a temperature change of the cooling medium (1110), thereby increasing cooling efficiency and safety of the cooling system.

In order to safely cool a target in the cooling system (10), a cooling tip (2000) may be disposable, and thus may be changed every surgery or treatment. In this case, required is a tip storage (4000) in which a plurality of cooling tips (2000) are safely stored so that the user may easily mount the cooling tips (2000) in a cooling device (1000) when the user uses a cooling system (10) for surgery or treatment.

Hereinafter, referring to FIG. 21 and FIG. 22, tip storage (4000) for storing the above cooling tips (2000) is described.

Figure 21:
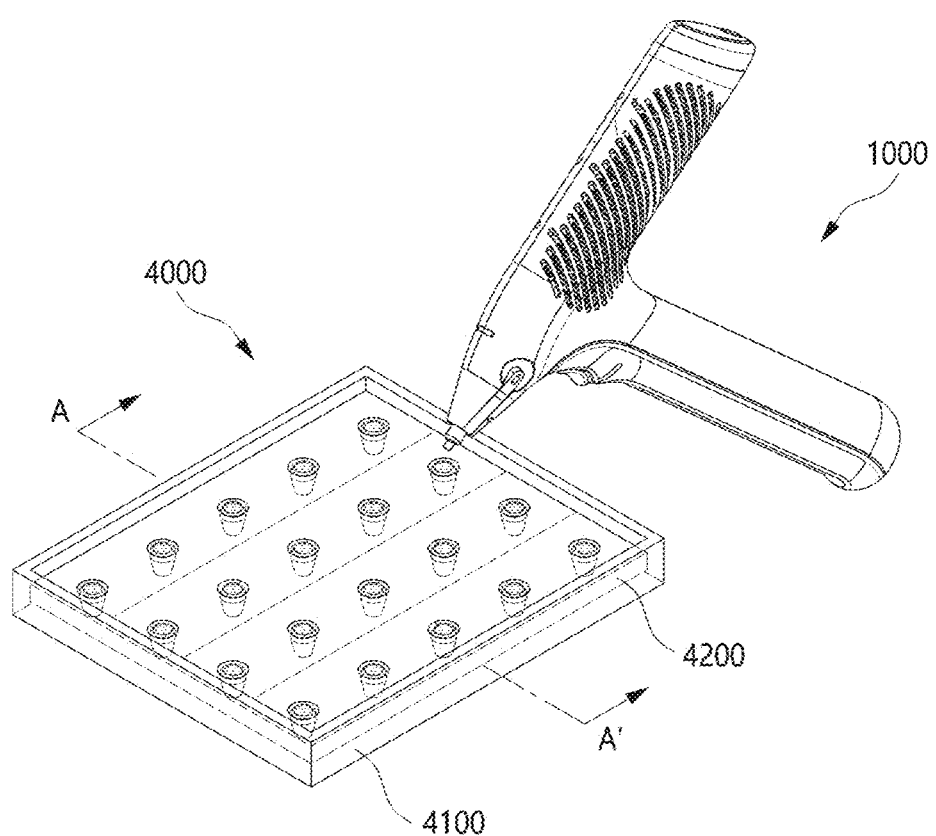
FIG. 21 shows an exemplary tip storage unit according to an exemplary embodiment of the present disclosure.

FIG. 21 shows a tip storage according to an embodiment of the present disclosure. Referring to FIG. 21, the tip storage (4000) may comprise a case (4100) and a storage member (4200).

A storage member (4200) may be disposed in a case (4100).

A case (4100) may be implemented to be portable, including a cover, and it is preferable to have a rectangular parallelepiped shape, but the technical idea of the present invention is not limited thereto, and various shapes can be implemented.

A storage member (4200) may accommodate a plurality of cooling tips (2000). For example, a storage member (4200) may have a plurality of storage holes (4210) for storing cooling tips (2000), wherein the plurality of storage holes (4210) may be each divided or separated. For example, a cutting guide such as a dotted line is marked or thin material is formed between each different storage holes (4210) so that the user may easily separate the storage holes (4210) individually.

A case (4100) and a storage member (4200) may be physically separated or integrally implemented.

Figure 22:
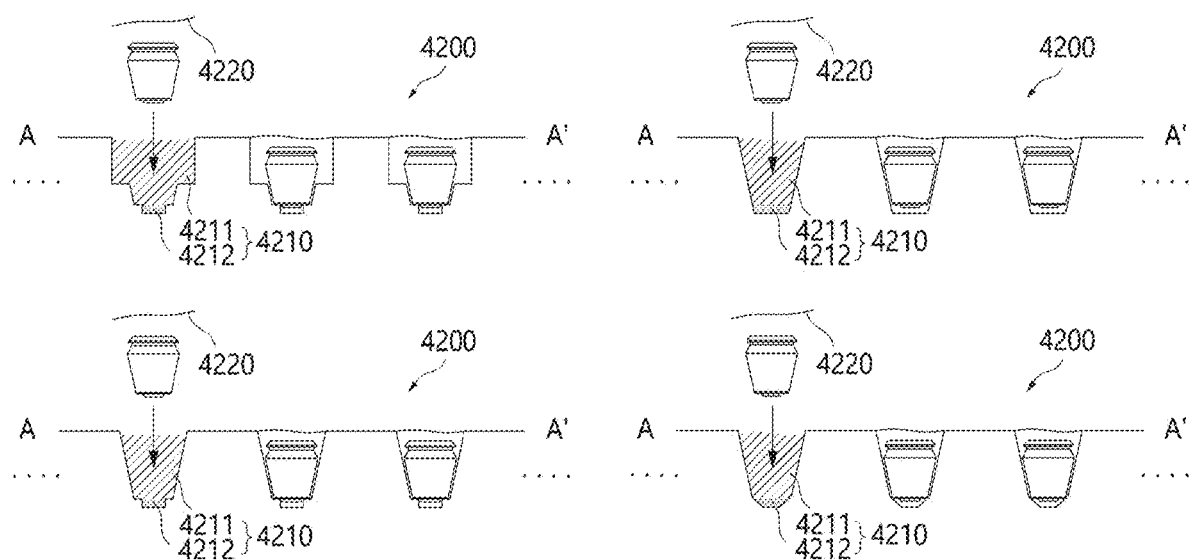
FIG. 22 shows a cross sectional view of an exemplary tip storage according to an exemplary embodiment of the present disclosure.

FIG. 22 shows a cross sectional view of a tip storage (4000) according to an embodiment of the present invention. Referring to FIG. 22, the tip storage (4000) may comprise storage hole (4210) to which cooling tip (2000) is inserted and a sealing member (4220) for packing. The sealing member may be prepared with a material softer than that of the storage hole (4210).

A storage hole (4210) may accommodate a cooling tip (2000). For example, a cooling tip (2000) may be inserted into a storage hole (4210) so that the contact member (2100) thereof faces the end of the storage hole (4210).

A storage hole (4210) may be implemented in a shape corresponding to a cooling tip (2000). For example, a storage hole (4210) may be implemented in a tapered shape that gets narrower toward the end of the storage hole (4210). In addition, the storage hole (4210) may comprise at least one step part as described later.

A storage hole (4210) may comprise a storage space (4211) for storing a cooling tip (2000) and a protection space (4212) for protecting the cooling tip (2000), wherein the storage space (4211) and the protection space (4212) may be defined by the inner wall of the storage hole (4210).

A storage space (4211) and a protection space (4212) may be divided according to a state in which a cooling tip (2000) is inserted into a storage hole (4210). For example, the storage space (4211) and the protection space (4212) may be divided by any one surface of the storage hole (4210) which is perpendicular to the insertion direction of the cooling tip (2000). For example, the storage space (4211) and the protection space (4212) may be divided by the surface, among the surfaces of the storage hole (4210), that has a diameter corresponding to the outer diameter of one end of a tip body (2200). For another example, a storage space (4211) may refer to an area of the inner space of the storage hole (4210), where the cooling tip is positioned, and the protection space (4212) may refer to an area, of the inner space of the storage hole (4210), between the contact member (2100) of the cooling tip (2000) and the end of the storage hole (4210) or an area expanding from the storage space (4211) to the end of the storage hole (4210).

The tip body (2200) of a cooling tip (2000) may be supported in a storage space (4211). For example, referring to FIG. 22, the storage space (4211) may be implemented in a shape corresponding to the tip body (2200) and fixed in a force fitting way by being inserted into a tip storage (4000), thereby supporting the tip body (2200) in the storage space (4211).

Specifically, the inner wall defining at least a portion of the storage space (4211) may have a gradient equal to or more gradual than the gradient of the lateral surface of the tip body (2200). For another example, the tip body (2200) of the cooling tip (2000) may by supported by a step part formed in the storage space (4211).

A storage space (4212) may be formed in a preset depth to prevent a cooling tip (2000) from being in contact with a storage hole (4210). For example, the depth of a protection space (4212) may be set to be longer than the protruding length of the contact member (2100) of the cooling tip (2000) from a tip body (2200). Since a protection space (4121) exists, the contact member (2100) of a cooling tip (2000) may not be in contact with the storage hole (4210), and thus may be maintained in a sterilized state.

A protection space (4212) may have various shapes. For example, referring to FIG. 22, the protection space (4212) may have the shapes of a cylinder, a truncated cone, rectangular parallelepiped or the like, wherein the storage hole (4210) may include a step part for supporting a cooling tip (2000), or the cross section of the protection space (4212) perpendicular to the direction of insertion of the cooling tip (2000) may be smaller than the cross section of a storage space (4211) in order to store the cooling tip (2000) by force fitting.

The inner wall of a protection space (4212) may have a gradient different from the gradient of the inner wall of a storage space (4211) in order to support the tip body (2200) of a cooling tip (2000). For example, an angle formed by the inner wall of the protection space (4212) and the central axis of a storage hole (4210) may be larger than an angle formed by the inner wall of the storage space (4211) and the central axis of the storage hole (4210).

A sealing member (4220) may maintain the sterilized state of a cooling tip (2000) by sealing a storage hole (4210) stored in the cooling tip (2000).

The descriptions feature a case where a tip storage (4000) that has a form of comprising a plurality of storage holes (4000) may be provided as a container for storing a cooling tip (2000), but the technical idea of the present invention is not limited thereto, and a tip storage (4000) that has a capsule form for storing one cooling tip (2000) may be provided as a container for storing the cooling tip (2000). Specifically, the cooling system (10) may include at least one capsule in which one cooling tip (2000) is stored, and each capsule may be comprising a storage hole (4210) comprising said storage space (4211) and a protection space (4212) and a sealing member (4220).

As the user uses a cooling device (1000), the user may place the cooling device (1000) in any place before, during, or after cooling a target. To this end, the cooling system (10) may include a holder (3000), and the user may place the cooling device (1000) on the holder (3000) wherein the holder (3000) may be implemented in a specific shape in order to prevent the generation of damage to the cooling device (1000) or a cooling tip (2000).

Hereinafter, referring to FIG. 23 and FIG. 24, a support that has the structure and shape for preventing damage to the cooling device (1000) or the cooling tip (2000) is described.

Figure 23:
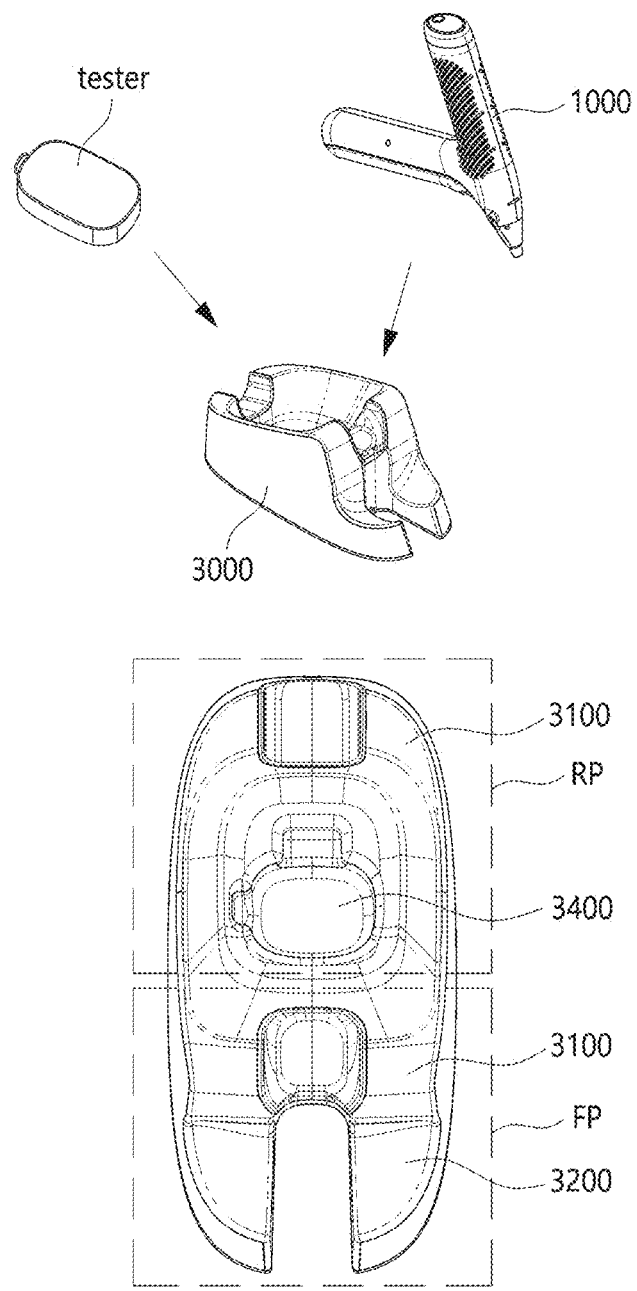
FIG. 23 shows the structure and shape of a support according to an exemplary embodiment of the present disclosure.

FIG. 23 shows the structure and shape of a holder (3000) according to an embodiment of the present disclosure. A cooling device (1000) may be placed on the support while a cooling tip (2000) is mounted or separated.

Referring to FIG. 23, a cooling device (1000) may be put on a holder (3000). For example, the body part and one end of a grip part of a cooling device (1000) may be placed on the front portion (FP) of the holder (3000), and the other end of the grip part of the cooling device (1000) may be put on the rear portion (RP) of the support.

Referring to FIG. 23, the front portion (FP) of the holder (3000) may comprise the initial placement part (3100) on which one end of the grip part of a cooling device (1000) is placed and blade part (3200) extended from the first placement part (3100) and protecting a cooling medium (1110) or a cooling tip (2000) of the cooling device (1000).

In this case, the first placement part (3100) may include the initial supporting groove on which one end of the grip part of a cooling device (1000) is placed. For example, when the grip part of the cooling device (1000) has a cylinder shape, the first placement part (3100) may have a groove recessed in a U shape and may further include a groove to which an input module (1700) disposed in the grip part of the cooling device (1000) is inserted.

In addition, the blade part (3200) may comprise the initial blade part (3210) and a second blade part (3220) protruding from the initial placement part (3100), and a space for the body part of the cooling device (1000) may be formed between the first blade part (3210) and the second blade part (3220). The shape of the blade part will be specifically described below.

Referring to FIG. 23, the rear portion (RP) of a holder (3000) may comprise a second placement part (3300) on which the other end of the grip part of a cooling device (1000) is placed, and a tester reception part (3400) in which a tester is received.

In this embodiment, the second placement part (3300) may include a second supporting groove in order to place the other end of the grip part of a cooling part (1000). For example, when the grip part of the cooling device (1000) has a cylindrical shape, the second placement part (3300) may have a groove recessed in a U shape and a grip space so that the user may easily grip the placed cooling device (1000). The cooling device (1000) may be settled on said first placement part (3100) and second placement part (3300) and placed on a holder (3000), and the user may place the cooling device (1000) on the holder (3000) or separate the cooling device (1000) from the holder (3000) by gripping the cooling device (1000) in the grip space disposed between the first placement part (3100) and the second placement part (3300).

In this embodiment, a tester reception part (3400) may receive a tester. For example, the tester reception part (3400) may include a reception space corresponding to the shape of the tester, and the tester may be inserted into a reception space of the tester reception part (3400).

A tester may make a test on the operation or performance of a cooling device (100) before the performance of cooling a target. To this end, the tester may comprise an insertion part to which a part of the cooling device (1000) that has a cooling medium (1110) or a cooling tip (2000) mounted therein is inserted, a sensor part for measuring the temperature of the cooling medium (1110) or the cooling tip (2000) of the cooling device (1000), and a control part for checking, by using sensing information acquired from the sensor part, whether the cooling device (1000) is normally operated. The tester may test whether the cooling device (1000) is operated according to said cooling control method, or whether the cooling device (1000) reach a specific temperature, or reach the specific temperature within a preset time. In addition, the tester may provide the user with a test result on the cooling device (1000) through a visual, auditory, and tactile notification. A separate cooling tip for test may be used when a tester is used.

Figure 24:
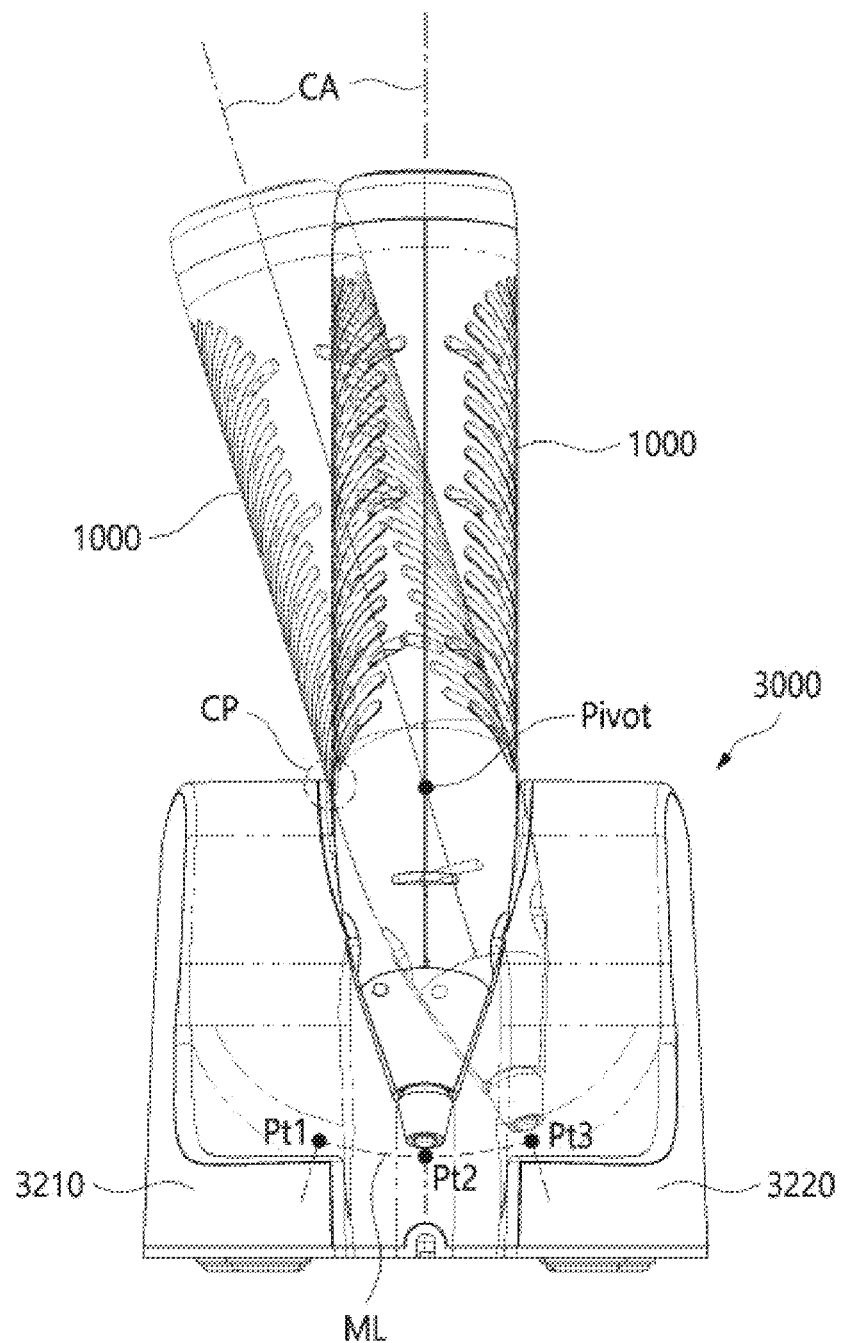
FIG. 24 shows a process of a cooling device being supported by a support according to an exemplary embodiment of the present disclosure.

FIG. 24 shows a process in which a cooling device may be placed on a holder (3000) according to an embodiment of the present invention. Referring to FIG. 24, in a process of being placed on a holder (3000), the cooling device (1000) may vertically enter the holder (3000) or may enter the holder (3000) in a state of being inclined in a predetermined angle. When the cooling device (1000) enters the holder (3000) in an inclined state, a cooling medium (1110) or a cooling tip (2000) may be damaged by being crashed into or scratched by the holder (3000).

In order to prevent the damage to said cooling device (1000) or cooling tip (2000), a holder (3000) may comprise a blade part (3200) that has a specific height. Referring to FIG. 24, the cooling device (1000) or the cooling tip (2000) mounted in the cooling device (1000) may move along a moving line (MV) formed by the inclination of the cooling device (1000), and a blade part (3200) protruding from the placement part (3100) may have a height lower than the moving line (MV). Specifically, when the end or the cooling device (1000) or a cooling tip (2000) moves to a third point (Pt3) from the initial point (Pt1) through a second point (Pt2) with respect to a pivot, the height of the first blade part (3210) may be set lower than the first point (Pt1), and the height of the second blade part (3220) may be set lower than the third point (Pt3). In this case, the moving line (MV) may be set by a contact point (CP) of the cooling device (1000) and a placement part (3100).

The blade part (3200) may be implemented in various shapes without a damage to a cooling device (1000) or a cooling tip (2000). For example, the blade part (3200) may include a curved surface, and thus the height of the blade part (3200) may not be constant. In this case, the shape of the blade part (3200) may be implemented so that the height of a part, of the blade part (3200), positioned in a preset range from a moving line (ML) of the end of the cooling device (1000) or the cooling tip (2000) is lower than the moving line (ML). For another example, the blade part (3200) may be implemented in a shape of not overlapping with a preset range from the moving line (ML) of the end of the cooling device (1000) or the cooling tip (2000).

As described above, the holder (3000) may be implemented in a specific shape so that a cooling medium (1110) or a cooling tip (2000) does not touch the support (300) even though a cooling device (1000) is inserted in any direction, and thus the cooling device (1000) may be placed on the holder (3000) more safely without damage.

The features, structures, effects and the like described in the embodiments above may be included in at least one embodiment of the present invention, and may necessarily not be limited to one embodiment. Furthermore, another embodiment may be practiced by a person skilled in the art through a combination or a change in the field to which the features, structures, effects, and the like exemplified in each embodiment belong. Therefore, the description related to such combinations and modifications should be interpreted as being included in the scope of the present invention.

In addition, although the embodiments have been described above, these are only examples and do not limit the present invention, and a person skilled in the art to which the present invention belongs will appreciate that various modifications and applications not illustrated above are possible within the range of the essential characteristics of the present embodiment. That is, each constituent element specifically shown in the embodiment may be modified and implemented. Also, the differences related to these modifications and applications should be construed as being included in the scope of the present invention defined in the scope of the claims.

Example 1—Use of Ocular Cooling Device for Anesthesia of Bob's Eye During Intravitreal Injection Procedure A medical practitioner, Dr. Johnson, starts an intravitreal injection procedure for Patient Bob's eye. Dr. Johnson intends to use a handheld ocular cooling device to cool the local temperature of the eye surface such that Patient Bob's eye feels numb during the injection procedure. It is important for Dr. Johnson that the procedure goes smoothly. Specifically, Dr. Johnson wants to ensure that the procedure properly achieves the proper anesthetic effect of Patient Bob's eye within a rapid time while minimizing risk of ice adhesion and other safety concerns such as endophthalmitis, which is mitigated by using a new sterile cooling tip. In this case, this is achieved through the device's built-in safety and temperature control features.

Dr. Johnson turns on the device and works on setting the desired temperatures and times. Specifically, Dr. Johnson, sets −13° C. for the standby temperature, 20 seconds for the standby contact time, 5 seconds for the standby trigger time, −15° C. for the target temperature, 10 seconds for the cooling time, and −3° C. for the safety temperature.

When Dr. Johnson activates the cooling activation input, the cooling device shows a message on its screen "New tip inserted?". If Dr. Johnson has inserted a new sterile cooling tip, Dr. Johnson again activates the cooling activation input, then the cooling medium of the cooling device is first cooled to the standby temperature of −13° C. Once the standby temperature is reached, the cooling device generates a beep sound, notifying Dr. Johnson of the cooled state and the device's readiness to be contacted with Patient Bob's eye. In addition to generating the audio notification, the cooling device starts a timer counting down the preset 20 seconds standby contact time. This timer is displayed through a screen on the device, visible for Dr. Johnson to see.

While the timer for the standby contact time is running, Dr. Johnson holds the cooling device and contacts the cooling tip of the device to Patient Bob's eye. Dr. Johnson contacts Patient Bob's eye 15 seconds after the standby temperature was reached. Moreover, when the cooling tip touches the patient's eye, the temperature of the cooling medium raises 1.5° C./sec due to the higher temperature of the eye surface. This change of the cooling medium temperature is detected by a sensor of the ocular cooling device. Because this change exceeded the predetermined threshold and this change was detected before the expiration of the 20 second standby contact time, the device generates a blinking light and beep sounds at tone1—this visual notification tells Dr. Johnson that the device has properly contacted the target surface. Here, the contact condition has been satisfied. Accordingly, the device continues to cool the cooling medium, which is thermally coupled to the cooling tip, to maintain the standby temperature.

After the satisfaction of the contact condition, the timer changes to display the preset 5 second standby trigger time and begins counting down this new time. 3 seconds into this new countdown, Dr. Johnson presses the anesthesia trigger on the ocular device. Dr. Johnson does so after confirming that the ocular device cooling tip is properly contacting the proper ocular region (e.g., the conjunctiva is approximately 3.5 mm away from the corneal limbus, and the cooling tip is not directly contacting the corneal limbus itself). This anesthesia trigger press is detected by another sensor of the ocular cooling device. Because this anesthesia trigger press was detected within the 5 second standby trigger time, the trigger condition is satisfied, and the device generates beeps indicating the start of cooling anesthesia. As both contact and trigger conditions were satisfied and the respective notifications were sent to Dr. Johnson, Dr. Johnson has confidence that the device is properly functioning and that proper contact was made. After the satisfaction of the trigger condition, the device proceeds to further cool the cooling medium to the preset −15° C. target temperature. Because the device was already at or near the standby temperature, it does not take long for this −15° C. target temperature to be reached. Moreover, the timer changes to display the preset 10 seconds cooling time and begins counting down this new time. During this 10 second cooling time, Dr. Johnson continues to maintain contact of the device with Patient's Bob eye. In addition, during this 10 second cooling time, the cooling device generates a beep sound every 2 seconds to indicate the countdown timer. The countdown time interval of 2 seconds could also have been changed beforehand. The device sends out another notification once the target temperature is reached. Once the cooling time is complete, a desired temporary anesthetic effect of Patient Bob's eye is achieved and the cooling of the cooling medium automatically ceases, raising the temperature of the cooling medium to the preset −3° C. such that Dr. Johnson can safely remove the device from the patient's eye surface without concern of ice adhesion while preserving the anesthetic effect that resulted from the device contact with Patient Bob's eye. The cooling device generates the ending beeps notifying that the cooling anesthesia procedure is completed. Dr. Johnson may perform an intravitreal injection within 30 seconds as Bob's eye temperature recovers and therefore anesthetic effect is diminished with time.

Example 2—Use of Ocular Cooling Device for Anesthesia of Jane's Eye During Intravitreal Injection Procedure Dr. Jones wants to starts an intravitreal injection procedure for Patient Jane's eye using a similar handheld device. Dr. Jones turns on the device and first checks the ambient temperature detected by the temperature sensor of the device and notices that it ranges from 22-24° C., which to Dr. Jones represents an acceptable error range. Dr. Jones also checks to see what preset values for the standby temperature, standby contact time, standby trigger time, target temperature, and safety temperature the device is set to. A separate computer operably coupled to the device displays −13° C. for the standby temperature, 20 seconds for the standby contact time, 5 seconds for the standby trigger time, −15° C. for the target temperature, 10 seconds for the cooling time, and −3° C. for the safety temperature—all desired parameters. Dr. Jones decides no updates to the preset values need to be made. A new sterile tip has a unique serial number, the device reads the serial number of the new sterile tip, verifies the tip is unused, and allows Dr. Jones to activate the cooling function of the device.

The cooling medium of the device reaches the preset −13° C. for the standby temperature. Once the standby temperature is reached, the cooling device vibrates, notifying Dr. Jones of the cooled state and the device's readiness to be contacted with Patient Jane's eye. In addition to generating the mechanical notification, a timer that is operably coupled to the device starts counting down from the preset 30 seconds standby contact time. This timer is displayed through a screen on the separate computer, visible for Dr. Jones to see.

While the timer for the standby contact time is running, Dr. Jones holds the cooling device. But before Dr. Jones has a chance to contact the cooling medium of the device to Patient Jane's eye, Dr. Jones is distracted and fails to contact Patient Bob's eye within the preset 20 seconds standby contact time. When the device fails to receive confirmation that contact has been made, cooling of the cooling medium automatically stops and the temperature automatically rises from the −13° C. standby temperature. Dr. Jones now has to start the process all over again. The device recognizes the failure of producing a proper contact, and does not require a new serial number of another new sterile tip.

This time, the procedure starts again. The device again reaches the preset −13° C. for the standby temperature, the device again vibrates notifying Dr. Jones of the cooled state, and the timer again starts counting down from 20 seconds. This time, however, Dr. Jones contacts Patient Jane's eye just 10 seconds after the timer started and a target surface contact detection element within the device registers the device's contact with Patient Jane's eye. A touch sensor of the device, which electrically coupled with the cooling medium and cooling tip, detects the cooling tip contacting the Jane's eye. The contact condition has been satisfied and the device continues to cool the cooling medium to maintain the standby temperature. A notification alerts Dr. Jones that the contact condition has been satisfied.

After the satisfaction of the contact condition, the timer changes to display the preset 10 second standby trigger time and begins counting down this time. However, Dr. Jones is again distracted and forgets to press a trigger on the device within the 5 second trigger time. Because this trigger press was not detected within the 5 second standby trigger time, the trigger condition is not satisfied and the device again automatically stops cooling the cooling medium. The cooling module of the device is powered off, causing the cooling tip temperature to rise.

Even though Dr. Jones was not fully engaged through the procedure, the safety features made available through the contact condition and the trigger condition mitigates any concerns around unnecessary cooling of the target surface.

This time, Dr. Jones successfully made the contact condition, the trigger condition, and was holding the cooling on Jane's eye. However, Dr. Jones inadequately held the device, and accidentally removed the cooling tip before the completion beep sound notifying the safety temperature of −3° C. However, the cooling tip of the device has a coating that has a weaker adhesion force to the cooling tip compared with the adhesion force at the target surface, so that this accidental removal of the cooling tip did not cause the damage to Jane's eye. Nevertheless, Dr. Jones could remove the cooling tip from the device simply clicking a button if emergent removal is necessary.

Example 3—Exemplary Instruction to Use Ocular Cooling Device

A user is given instructions on how to set up her ocular cooling device prior to treatment. Before installing a cooling tip to the ocular cooling device, the user is instructed to ensures that the ocular cooling device is clean and a cooling tip is disinfected and/or properly covered with a sterile cover or barrier. The user is instructed to turn on the power of the of the ocular cooling device by pressing the power button. The user is also instructed to refer the device LCD display or LED indicator to check if the device is at normal status to use. Then, the user is instructed to open up a sterile cover of a tip storage and install a cooling tip to the ocular cooling device by applying pressure to the cooling tip within the tip storage without touching the cooling tip until the latches on the ocular cooling device are fully engaged with the cooling tip. The desired cooling temperature and cooling time and desired safety temperature may also be set up by pressing the control button.

The user is then instructed to sanitize the ocular surface of the patient with an antiseptic solution, such as povidone iodine. Then the user is instructed to confirm that the ocular cooling device is ready to start cooling by confirming the power status light is on or its LCD screen says "Power on", to press the cooling activation button and to wait for a message on the screen of the ocular cooling device "New tip inserted?". The user may press the cooling activation button again to confirm. If the new tip has not been inserted, the user is instructed to insert a new cooling tip to the ocular cooling device and then press the cooling activation button to proceed. Then, the user is instructed to hold the ocular cooling device so that the cooling tip points toward the ocular surface of the patient. Then, the user is instructed to wait for a single beep sound notification indicating that the cooling tip temperature reaches the standby temperature. The user will see the screen of the ocular cooling device displaying a timer for the standby contact time with its "Ready" status, and timer will start to run. Then the user is instructed to place the cooling tip on the ocular surface of the patient before the standby contact time is expired. The user is warned that care should be taken when selecting an area of the ocular surface to target as once the cooling tip touches an area of the ocular surface, the cooling tip may have ice adhesion to the eye surface and cannot be repositioned to another area of the ocular surface without turning the power off or starting over the process. It can be informed to the user that if the cooling tip fails to properly contact the ocular surface within the standby contact time, the cooling device is automatically reset with "Resetting" on its LCD screen such that the cooling tip temperature rises to room temperature. The user is then instructed to wait for a blinking light and beep sounds at tone1 every 1 second indicating that the cooling tip is properly placed on the ocular surface then to press cooling activation button to proceed. The user will see the screen of the ocular cooling device displaying a timer for the standby trigger time with the status "Contacted" and timer will start to run. The user is instructed to press the trigger button on the ocular cooling device before the standby trigger time is expired. The user will see the screen of the ocular cooling device will display a timer for the cooling time with the status "In Process" when the cooling trigger is pressed, and the timer will start to run. The user is also informed that the ocular cooling anesthesia device produces the two tones beep at tone1→tone2 when the trigger button is pressed. The tone2 may have a higher pitch than tone1. If the user does not press trigger button within the standby contact time, the cooling device is automatically reset with "Resetting" on its screen such that the cooling tip temperature rises to room temperature. The user is instructed to maintain the contact of the cooling tip to the ocular surface of the patient during the entire cooling time. The user is instructed to wait for a beep sound indicating the completion of cooling procedure. Once the cooling procedure is completed, the cooling tip temperature will be raised to a safety temperature. The user is then instructed to wait for the next two tones beep sound at tone2→tone1 indicating that the cooling tip temperature reaches the safety temperature before carefully removing the cooling tip from the ocular surface of the patient. The ocular cooling device LCD displays says "Done" or "Resetting".

One the cooling procedure is completed, the user is to instructed to apply an antiseptic agent to the ocular surface. Then, the user is instructed to administrate an intravitreal injection within a certain time window before the cooling anesthetic effect wears off. If the user fails to perform IVT within the time window, the user is instructed to perform another anesthetic procedure.

Once the procedure is finished, the user is instructed to hold the ocular cooling device so that the cooling tip points toward the ground and press the latches on the ocular cooling device to separate the cooling tip from the ocular cooling device. Then, the user is instructed to discard the removed cooling tip following the local requirements and protocol.

In an event that a cooling procedure must be terminated before the pre-programmed cycle is complete, a user can be instructed to stop the cooling procedure anytime by pressing power button or by holding the trigger button for 1 second of the ocular cooling device. If the cooling tip is already placed on the ocular surface, wait at least 10 seconds before removing the cooling tip from the ocular surface of the patient. The ocular cooling anesthesia device may produce two tones beep at tone2→tone1 to indicate the tip temperature is at the safety temperature. In an event that the cooling procedure fails to terminate, a user can separate the cooling tip from the ocular cooling device by pressing the latches to stop the procedure. If the cooling tip is already placed on the ocular surface, wait at least 10 seconds before remove the cooling tip from the ocular surface of the patient.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of controlling temperature of a handheld cooling device to safely cool a target surface, the method comprising:
   i) providing the handheld cooling device, wherein the handheld cooling device comprises (a) a cooling medium; (b) a target surface contact element; (c) a target surface contact detection module configured to detect contact of the target surface contact element with the target surface; (d) an input element; (e) an input element detection module configured to detect actuation of the input element; and (f) a control module configured to receive a standby temperature, a standby contact time, a standby trigger time; and a target temperature;
   ii) receiving, by the control module, the standby temperature, the standby contact time, the standby trigger time; and the target temperature;
   iii) cooling the cooling medium to reach the standby temperature;
   iv) detecting, by the target surface contact detection module, a contact of the target surface contact element with the target surface within the standby contact time;

v) detecting, by the input element detection module, an actuation of the input element within the standby trigger time, wherein the detection of the contact is detected before the detection of the actuation of the input element; and vi) cooling the cooling medium to the target temperature when the contact is detected within the standby contact time and the actuation is detected within the standby trigger time, wherein the target temperature is lower than the standby temperature.

2. The method of claim 1, wherein the standby trigger time begins when the contact of the target surface contact element is detected.

3. The method of claim 1, wherein the standby contact time begins when the cooling medium reaches the standby temperature.

4. The method of claim 1, wherein the target surface contact detection module comprises a temperature sensor, a pressure sensor, or a capacitive sensor.

5. The method of claim 4, wherein the target surface contact detection module comprises the temperature sensor, and the detection of the contact comprises detecting, by the temperature sensor, an instantaneous rate of change of temperature (dT/dt) of the cooling medium being more than or equal to a predetermined threshold.

6. The method of claim 5, wherein the device further comprises a second temperature sensor, and the detection of the contact further comprises detecting, by the second temperature sensor, an instantaneous rate of change of temperature (dT/dt) of the cooling medium.

7. The method of claim 6, wherein the temperature sensor is disposed proximal to the target surface contact element, and the second temperature sensor is disposed distal to the target surface contact element.

8. The method of claim 5, wherein the predetermined threshold comprises at least 1° C./sec.

9. The method of claim 1, wherein the actuation of the input element comprises pressing a button, turning a knob, or flipping a switch.

10. The method of claim 1, wherein the target surface contact element comprises a tip member.

11. The method of claim 1, wherein the standby contact time comprises less than or equal to 60 seconds.

12. The method of claim 1, wherein the standby trigger time comprises less than or equal to 20 seconds.

13. The method of claim 1, wherein the handheld cooling device further comprises a notification module, and the method further comprises sending a notification, by the notification module, when the contact is detected within the standby contact time or when the actuation is detected within the standby trigger time.

14. The method of claim 13, wherein the notification comprises an audio alert, a visual alert, or any combination thereof.

15. The method of claim 1, wherein the control module is further configured to receive a target temperature time, the method further comprising maintaining the cooling medium at the target temperature for the target temperature time.

16. The method of claim 15, wherein the target temperature time is 60 seconds or less.

17. The method of claim 15, further comprising stopping the cooling of the cooling medium when the target temperature time is reached.

18. The method of claim 1, wherein the target surface is an ocular region.

19. The method of claim 1, wherein the standby temperature is selected from 0° C. to −20° C.

20. The method of claim 1, wherein the target temperature is selected from −5° C. to −60° C.

* * * * *

UNITED STATES PATENT AND TRADEMARK OFFICE
CERTIFICATE OF CORRECTION

| | | |
|---|---|---|
| PATENT NO. | : 11,278,341 B2 | Page 1 of 1 |
| APPLICATION NO. | : 17/373237 | |
| DATED | : March 22, 2022 | |
| INVENTOR(S) | : Gun-Ho Kim et al. | |

It is certified that error appears in the above-identified patent and that said Letters Patent is hereby corrected as shown below:

On the Title Page

Column 1, below "(65) Prior Publication Data" insert the following as a new field entry:
-- (30) Foreign Application Priority Data
Jul. 14, 2020 (KR) ........ 10-2020-0087100
Oct. 8, 2020 (KR) ........ 10-2020-0130588 --.

Signed and Sealed this
Twenty-third Day of April, 2024

Katherine Kelly Vidal
*Director of the United States Patent and Trademark Office*